(12) United States Patent
Ghods et al.

(10) Patent No.: US 11,454,606 B2
(45) Date of Patent: Sep. 27, 2022

(54) METHOD AND SYSTEMS RELATING TO CONSTRUCTION MATERIAL ASSESSMENT

(71) Applicant: GIATEC SCIENTIFIC INC., Nepean (CA)

(72) Inventors: Pouria Ghods, Gloucester (CA); Rouhollah Alizadeh, Nepean (CA); Mustafa Salehi, Nepean (CA)

(73) Assignee: GIATEC SCIENTIFIC, Ottawa (CA)

( * ) Notice: Subject to any disclaimer, the term of this patent is extended or adjusted under 35 U.S.C. 154(b) by 118 days.

(21) Appl. No.: 17/012,677

(22) Filed: Sep. 4, 2020

(65) Prior Publication Data

US 2021/0033553 A1 Feb. 4, 2021

Related U.S. Application Data

(63) Continuation of application No. 15/958,481, filed on Apr. 20, 2018, now Pat. No. 10,768,130, which is a
(Continued)

(51) Int. Cl.
*G01R 27/08* (2006.01)
*G01N 27/02* (2006.01)
(Continued)

(52) U.S. Cl.
CPC ........ *G01N 27/026* (2013.01); *G01M 5/0008* (2013.01); *G01M 5/0083* (2013.01);
(Continued)

(58) Field of Classification Search
CPC ...... G01N 17/00; G01N 17/006; G01N 17/02; G01N 17/04
(Continued)

(56) References Cited

U.S. PATENT DOCUMENTS 3,468,001 A 9/1969 Bodine, Jr.
5,672,968 A 9/1997 Miller et al.
(Continued)

FOREIGN PATENT DOCUMENTS

CN 102495108 A 6/2012
EP 1832870 A1 9/2007
(Continued)

OTHER PUBLICATIONS

Brameshuber et al. "Non-Destructive Determination of the Water-Content in the Concrete Cover using the Multiring Electrode." Int. Symp. Non-Destructive Testing in Civil Eng. (NDT-CE) (Sep. 2003) vol. 8, No. 10. https://www.ndt.net/article/ndtce03/papers/p041/p041.htm (last accessed Feb. 2, 2022).
(Continued)

*Primary Examiner* — Raul J Rios Russo
(74) *Attorney, Agent, or Firm* — Rosenberg, Klein & Lee

(57) ABSTRACT

Hundreds of thousands of concrete bridges, buildings etc. and hundreds of billions of tons of concrete require characterization throughout the process from manufacture to pouring and curing and on throughout service life. The characterization may relate to initial concrete properties, projected concrete properties, framework removal, corrosion, failure etc. Accordingly, a variety of measurements such as water content, electrical resistivity, and half-cell corrosion potential for example would be beneficially implemented as easy to use field test equipment or embedded sensors allowing lifetime monitoring to be performed rather than discrete assessments when issues become evident.

21 Claims, 42 Drawing Sheets

Related U.S. Application Data continuation-in-part of application No. 15/496,298, filed on Apr. 25, 2017, now Pat. No. 10,571,418, and a continuation-in-part of application No. 15/474,175, filed on Mar. 30, 2017, now Pat. No. 10,324,078, and a continuation-in-part of application No. 15/311,055, filed as application No. PCT/CA2015/000314 on May 13, 2015, now Pat. No. 10,775,332, said application No. 15/496,298 is a continuation of application No. 14/168,254, filed on Jan. 30, 2014, now Pat. No. 9,638,652.

(60) Provisional application No. 62/315,202, filed on Mar. 30, 2016, provisional application No. 61/992,364, filed on May 13, 2014, provisional application No. 61/758,309, filed on Jan. 30, 2013.

(51) Int. Cl.
  *G01N 17/02* (2006.01)
  *G01N 33/38* (2006.01)
  *G01M 5/00* (2006.01)
  *G01N 27/04* (2006.01)
  G01N 17/00 (2006.01)
  G01L 1/20 (2006.01)
  G01L 1/22 (2006.01)
  G01L 1/10 (2006.01)
  G01R 27/00 (2006.01)

(52) U.S. Cl.
  CPC ............ *G01N 17/02* (2013.01); *G01N 27/02* (2013.01); *G01N 27/04* (2013.01); *G01N 33/383* (2013.01); *G01L 1/10* (2013.01); *G01L 1/20* (2013.01); *G01L 1/22* (2013.01); *G01N 17/00* (2013.01); *G01N 17/006* (2013.01); *G01R 27/00* (2013.01)

(58) Field of Classification Search
  USPC ........ 324/71.2, 76, 439, 459, 549, 600, 635, 324/639, 644, 649, 662, 671, 691, 693, 324/700, 716
  See application file for complete search history.

(56) References Cited

U.S. PATENT DOCUMENTS

| | | | |
|---|---|---|---|
| 5,720,354 | A | 2/1998 | Stump et al. |
| 6,396,265 | B1 | 5/2002 | Shtakelberg et al. |
| 6,826,117 | B2 | 11/2004 | Haase et al. |
| 7,034,660 | B2 | 4/2006 | Watters et al. |
| 7,181,978 | B2 | 2/2007 | Shtakelberg et al. |
| 7,225,682 | B2 | 6/2007 | Shtakelberg et al. |
| 8,610,444 | B2 | 12/2013 | Shtakelberg et al. |
| 8,805,423 | B2 | 8/2014 | Sridhara et al. |
| 8,868,133 | B1 | 10/2014 | Rosenbaum et al. |
| 9,790,688 | B2 | 10/2017 | Mustapha et al. |
| 9,816,978 | B2 | 11/2017 | Bartholomew et al. |
| 2002/0057097 | A1 | 5/2002 | Kelly et al. |
| 2002/0154029 | A1 | 10/2002 | Watters et al. |
| 2003/0156495 | A1 | 8/2003 | Haase et al. |
| 2004/0004554 | A1 | 1/2004 | Srinivasan et al. |
| 2004/0153270 | A1 | 8/2004 | Yamashita et al. |
| 2005/0103119 | A1 | 5/2005 | Shtakelberg et al. |
| 2005/0192765 | A1 | 9/2005 | Slothers et al. |
| 2005/0199424 | A1 | 9/2005 | Stump et al. |
| 2005/0210995 | A1 | 9/2005 | Drnevich et al. |
| 2007/0090945 | A1 | 4/2007 | Hoogenboom |
| 2007/0210814 | A1 | 9/2007 | Albadri et al. |
| 2008/0042901 | A1 | 2/2008 | Smith et al. |
| 2008/0067228 | A1 | 3/2008 | Kaga et al. |
| 2008/0272131 | A1* | 11/2008 | Roberts .................. G01K 1/14 220/592.25 |
| 2010/0225341 | A1 | 9/2010 | Burrows et al. |
| 2012/0012470 | A1 | 1/2012 | Bartholomew et al. |
| 2012/0078278 | A1* | 3/2012 | Bales, Jr. ....... A61B 17/320092 606/169 |
| 2012/0176103 | A1 | 7/2012 | Lizarazo et al. |
| 2014/0062489 | A1 | 3/2014 | Pindiprolu et al. |
| 2015/0057030 | A1 | 2/2015 | Rosenbaum |
| 2016/0018383 | A1 | 1/2016 | Radjy |
| 2016/0061751 | A1 | 3/2016 | Carr |
| 2016/0228914 | A1* | 8/2016 | Bales, Jr. .............. B06B 1/0223 |
| 2016/0291060 | A1 | 10/2016 | Wood et al. |
| 2019/0242840 | A1 | 8/2019 | Ghods et al. |

FOREIGN PATENT DOCUMENTS

| | | |
|---|---|---|
| EP | 3441775 A2 | 2/2019 |
| IL | 117443 A | 6/2000 |
| IL | 134799 A | 7/2003 |
| JP | 5811792 B2 | 11/2015 |
| WO | 2005062066 A2 | 7/2005 |
| WO | 2011130637 A2 | 10/2011 |
| WO | 2013041885 A1 | 3/2013 |
| WO | 2015172231 A1 | 11/2015 |

OTHER PUBLICATIONS

McCarter et al. "Dependence of Electrical Impedance of Cement-Based Materials on their Moisture Condition." J. Physics D: Appl Phys., vol. 22, No. 11 (Nov. 1989), pp. 1773-1776. doi:10.1088/0022-3727/22/11/033.

Stackelberg et al. "Physical Nature of Linear Correlations 'Strength-Resistivity' by Control Hardening Cement-Concrete Compositions." Building Materials, vol. 3 (2010), pp. 118-122. Translated from Russian.

Stackelberg et al. "Principles of Monitoring Hardening and Strengthening of Shotcrete." J. Chinese Ceramic Society, vol. 42, No. 5 (May 2014), pp. 568-573. doi: 10.7521/j.issn.0454-5648.2014.05.02.

Tikalsky et al. "Maturity Method Demonstration: Final Report." Technical Report No. FHWA-OR-DF-04-01 (Jul. 2003), sponsored by Oregon Department of Transportation Research Unit and Federal Highway Administration.

\* cited by examiner

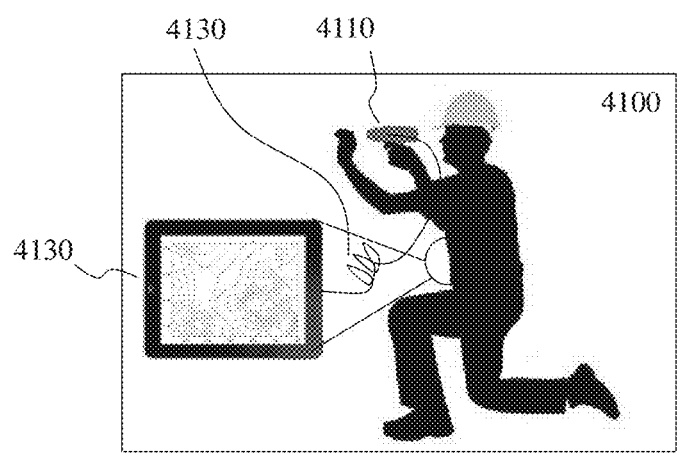
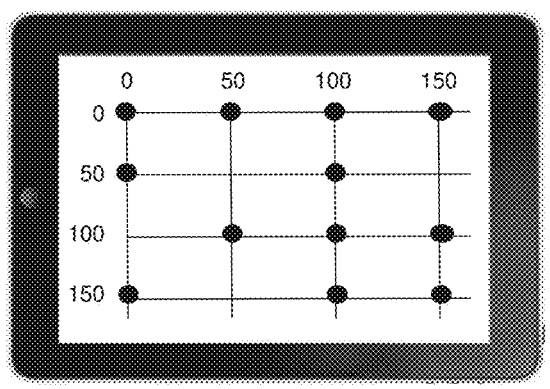
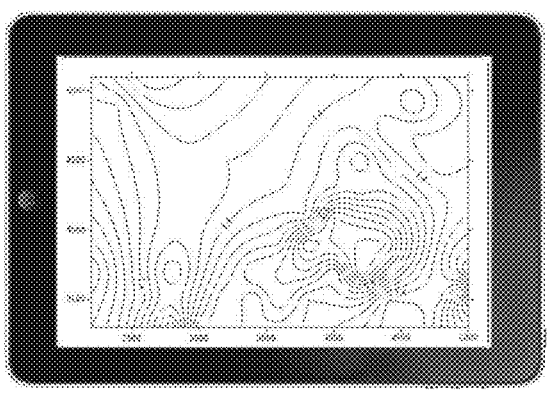
Figure 4C

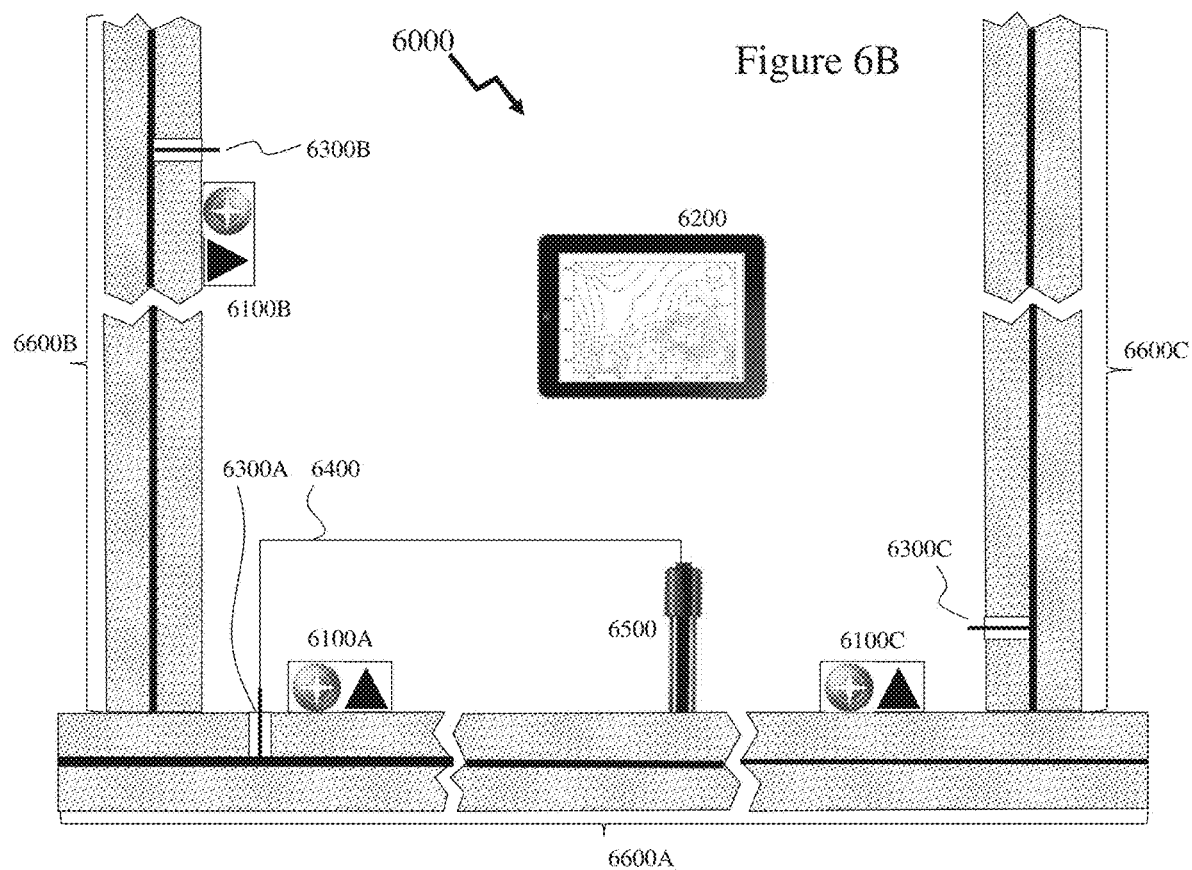

$t_i$ = initial setting time, $t_f$ = final setting time

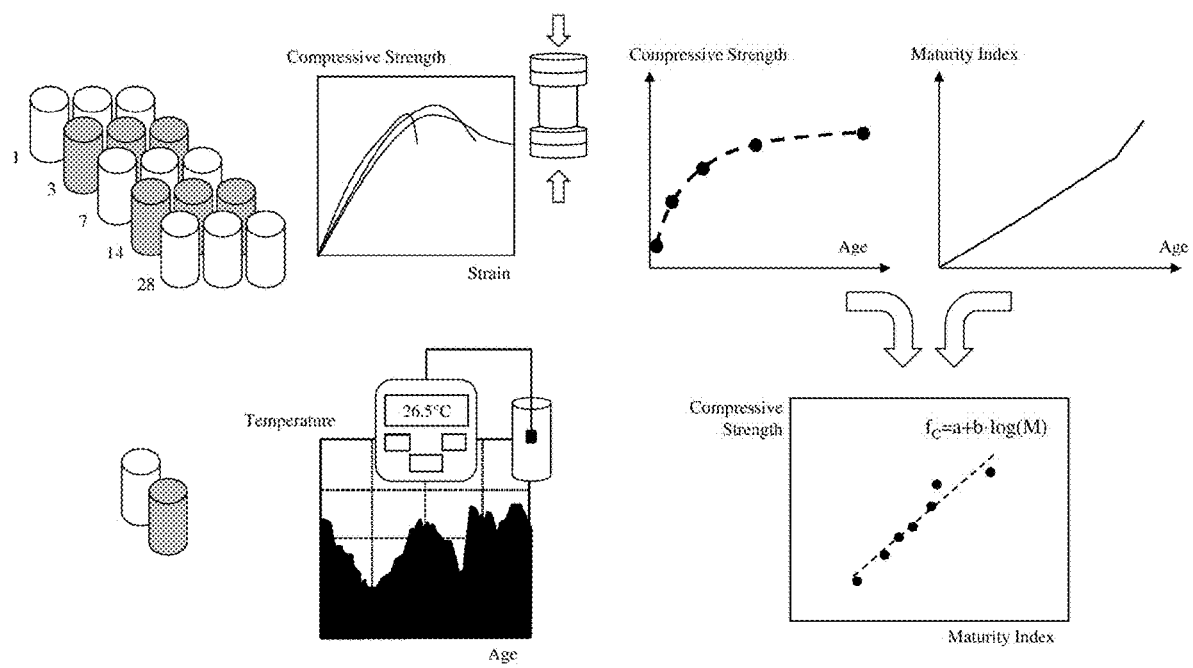
Figure 28                    Figure 29

METHOD AND SYSTEMS RELATING TO CONSTRUCTION MATERIAL ASSESSMENT

CROSS-REFERENCE TO RELATED APPLICATIONS

This patent application claims the benefit of priority as a continuation of U.S. patent application Ser. No. 15/958,481 filed Apr. 20, 2018 entitled "Methods and Systems relating to Construction Material Assessment", the entire contents of which are incorporated herein by reference.

This patent application claims the benefit of priority as a continuation-in-part of U.S. patent application Ser. No. 15/496,298 filed Apr. 25, 2017 entitled "Electrical Methods and Systems for Concrete Testing", which itself claims the benefit of priority as a continuation of U.S. patent Ser. No. 14/168,254 filed on Jan. 30, 2014 entitled "Electrical Methods and Systems for Concrete Testing", which itself claims the benefit of priority from U.S. Provisional Patent Application 61/758,309 filed on Jan. 30, 2013 entitled "Electrical Methods and Systems for Concrete Testing", the entire contents of each being included by reference.

This patent application claims the benefit of priority as a continuation-in-part of U.S. patent application Ser. No. 15/311,055 filed Nov. 14, 2016 entitled "Electrical Methods and Systems for Concrete Testing", which itself claims the benefit of priority from Patent Cooperation Treaty Application PCT/CA2015/000,314 entitled "Electrical Methods and Systems for Concrete Testing" filed May 13, 2015, which itself claims the benefit of priority from U.S. Provisional Patent Application 61/992,364 filed May 13, 2014 entitled "Electrical Methods and Systems for Concrete Testing", the entire contents of each being included by reference.

This patent application claims the benefit of priority as a continuation-in-part of U.S. patent application Ser. No. 15/474,175 filed Mar. 30, 2017 entitled "Embedded Wireless Monitoring Sensors", which itself claims the benefit of priority from U.S. Provisional Patent Application 62/315,202 filed Mar. 30, 2016 entitled "Embedded Wireless Monitoring Sensors", the entire contents of each being included by reference.

FIELD OF THE INVENTION

The present inventions relate to concrete testing and concrete structure characterization, more particularly to electrical methods and systems for establishing cured concrete performance from measurements of wet concrete, automated methods and systems for periodic and/or continuous characterization of concrete structures, electrical methods and systems for corrosion measurement of rebar in reinforced concrete structures, construction material process monitoring and compact self-contained electrical sensors with wireless interfaces.

BACKGROUND OF THE INVENTION

Concrete can be one of the most durable building materials and structures made of concrete can have a long service life. Concrete is a composite construction material composed primarily of aggregate, cement, and water. It provides superior fire resistance, compared with wooden construction and can gain strength over time. Further, as it is used as liquid that subsequently hardens it can be formed into complex geometries and may poured either directly into formworks at the construction sites (so called ready mix concrete) or employed remotely to pre-build concrete elements and structures. Overall concrete is the most widely used construction material in the world with an annual consumption estimated at approximately 30 billion tons in 2006, compared to 2 billion in 1950. During the next 5 years concrete consumption is estimated to grow with a Compound Annual Growth Rate (CAGR) between 6% and 9% according to market forecasts of cement and concrete admixtures globally over the period 2012 to 2017 such that the 30 billion ton consumption will increase to approximately 40 billion tons.

There are many types of concrete available, created by varying the proportions of the main ingredients of cement, aggregate, and water as well as reinforcement means, chemical admixtures, and mineral admixtures. In this way or by substitution for the cemetitious and aggregate phases, the finished product can be tailored to its application with varying strength, density, or chemical and thermal resistance properties. Examples of chemical admixtures include accelerators to speed up the hardening of concrete, retarders to slow the hardening of concrete for large or difficult pours, air entrainments to capture air bubbles, plasticizers to increase workability, pigments for colour, corrosion inhibitors, bonding agents and pumping aids. Recently the use of recycled materials as concrete ingredients has been gaining popularity because of increasingly stringent environmental legislation. The most conspicuous of these is fly ash, a by-product of coal-fired power plants. This use reduces the amount of quarrying and landfill space required as the ash acts as a cement replacement thus reducing the amount of cement required.

Concrete is strong in compression, as the aggregate efficiently carries the compression load. However, it is weak in tension as the cement holding the aggregate in place can crack, allowing the structure to fail. Reinforced concrete solves these problems by adding steel reinforcing bars, steel fibers, glass fiber, or plastic fiber to carry tensile loads. Thereafter the concrete is reinforced to withstand the tensile loads upon it. Due to their low cost and wide availability steel reinforcing bar (commonly referred to as rebar) has been the dominant reinforcing material for the past 50 years. However, these steel rebars may corrode whereby the oxidation products (rust) expand and tend to flake, thereby cracking the concrete and reducing the bonding between the rebar and the concrete. Such corrosion may arise from several sources including carbonation when the surface of concrete is exposed to high concentration of carbon dioxide or chlorides, such as when the concrete structure is in contact with a chloride-contaminated environment such as arises with de-icing salts and marine environment.

Chlorides, including sodium chloride, contribute to the initiation of corrosion in embedded steel rebar if present in sufficiently high concentration. Chloride anions induce both localized corrosion (pitting corrosion) and generalized corrosion of steel reinforcements. Accordingly, the quality of water used for mixing concrete becomes important, as does ensuring that the coarse and fine aggregates do not contain chlorides, and nor do any admixtures contain chlorides. However, it was once common for calcium chloride to be used as an admixture to promote rapid setting of the concrete as it was also mistakenly believed to prevent freezing. However, this practice has fallen into disfavor once the deleterious effects of chlorides became known, but a significant portion of existing concrete infrastructure employed calcium chloride. Additionally, the use of de-icing salts on roadways, used to reduce the freezing point of water, probably to date has been one of the primary causes of premature failure of reinforced or pre-stressed concrete bridge decks, roadways, and parking garages.

Corrosion is an electro-chemical process. Accordingly, the flow rate of the ions between the anode and cathode areas, and therefore the rate at which corrosion can occur, is affected by the resistivity of the concrete. Empirical tests comparing electrical resistivity ($\rho$) measurements with other physical and chemical analysis have generated threshold values with the prior art for determining the wherein if $\rho > 120$ $\Omega \cdot m$ corrosion is deemed unlikely, if $\rho < 80$ $\Omega \cdot m$ then corrosion is fairly certain, and where $80$ $\Omega \cdot m \leq \rho \leq 120$ $\Omega \cdot m$ corrosion is possible. However, these values have to be used cautiously as there is strong evidence that chloride diffusion and surface electrical resistivity are dependent on other factors such as mix composition and age. Further, the electrical resistivity of the concrete cover layer decreases due to increasing concrete water content, increasing concrete porosity, increasing temperature, increasing chloride content, and decreasing carbonation depth. However, as an overall industry rule when the electrical resistivity of the concrete is low, the rate of corrosion increases. When the electrical resistivity is high, e.g. in case of dry and carbonated concrete, the rate of corrosion decreases.

Laboratory based measurements of electrical resistivity may exploit two electrode methods wherein the concrete electrical resistance is measured by applying a current using two electrodes attached to the ends of a uniform cross-section specimen and electrical resistivity calculated. This method suffers from the disadvantage that contact resistance can significantly add to the measured resistance causing inaccuracy. Accordingly, on-site electrical resistivity of concrete is commonly measured using four probes in what is known as a Wenner array which is used for the same reason as in the laboratory methods, namely to overcome contact errors. In this method four equally spaced probes are applied to the specimen in a line. The two outer probes induce the current to the specimen and the two inner electrodes measure the resulting potential drop. The probes are all applied to the same surface of the specimen and the method is consequently suitable for measuring the resistivity of bulk concrete in situ. Less commonly employed is a transformer to measure resistivity without any direct contact with the specimen. The transformer consists of a primary coil which energises the circuit with an AC voltage and a secondary which is formed by a toroid of the concrete sample.

However, it would be evident that for the US alone with over 600,000 concrete bridges and their associated support piers together with 55,000 miles of concrete road surface and billions of tons of concrete in buildings represent a significant measurement hurdle in terms of establishing protocols for rapid testing as well as associating the measurements specifically to particular elements of the physical infrastructure being evaluated. This is without considering all of the other elements of infrastructure built using concrete such as aqueducts, viaducts, railway bridges, pedestrian bridges, underground railways, subways, and buildings for example.

Accordingly, it would be beneficial for a field characterization system to automatically triangulate the location of the electrical resistivity device so that mapping of a structure can be performed without requiring an initial mapping of the structure to define measurement locations. It would be evident that erroneous association of electrical resistivity measurements to the wrong section of a structure may result in substantial disruption, such as closing the wrong side of a bridge to perform repairs where it then becomes evident the other side was actually corroding as the repairs having destroyed the road surface to get to the rebars find them non-corroded. Further, such erroneous activities substantially increase the overall costs of performing repairs straining already limited Federal and State budgets for example.

In other circumstances the concrete may have been covered with asphalt as a result of road resurfacing, repairs, etc. Accordingly, there is the problem of making quick and reproducible contact to the concrete through these overlying materials. It would therefore be beneficial to provide a means of improving this contact in such a manner. Likewise, it is the low frequency impedance of rebar in concrete that is correlated to the corrosion state of the steel reinforcement rods within the concrete. Accordingly, the direct measurement of the low frequency impedance of the rebar is a very time consuming measurement and one that is vulnerable to noise. As such, this low frequency technique is not easy to use in the field which is why commercial prior art electrical resistivity meters employ AC measurements of electrical resistivity at certain high enough frequencies. Hence, it would be beneficial to provide a means of making the electrical resistivity measurements that allows the low frequency resistivity to be derived from the measurements thereby improving determination of corrosion whilst reducing measurement times.

Likewise, prior art techniques for measuring the electrical resistivity of rebar, such as half-cell potential measurements, require that electrical connection is made to the rebar in contrast to concrete electrical resistivity measurements that determine the properties of the concrete surrounding the rebar. Accordingly, this requirement increases the complexity of making the measurements and requiring additional disruption/repair/cost even when no corrosion is identified. However, in many instances this is not feasible such as with epoxy coated steel rebar which is intended to reduce the occurrences of corrosion but as the rebars are electrically isolated from each other half-cell potential measurements are infeasible. As such it would be beneficial to provide a method of determining the state of rebar without requiring an electrical contact to the rebar with in the concrete infrastructure.

Just as the exploitation of concrete increased over the past 50 years then so have the requirements on it as engineering structures continue to push new boundaries of higher buildings, longer bridges, larger dams, artificial islands etc. Further disasters with poor concrete etc. have led to stricter regulation and compliance requirements. Accordingly, today the concrete industry faces competing demands for faster construction, shorter durations of formwork use, cost reductions whilst ensuring safety and quality are met or exceeded. As such testing techniques for concrete have evolved and will continue to evolve to meet these requirements. However, many of these techniques require samples be taken, full extended curing of the concrete performed, or simple mechanical tests be performed on site with the concrete being delivered.

However, it would be beneficial to provide concrete suppliers, construction companies, regulators, architects, and others requiring data regarding the cure, performance, corrosion of concrete at different points in its life cycle with a series of simple electrical tests that removed subjectivity, allowed for rapid assessment, were integrable to the construction process, and provided full life cycle assessment.

For large construction projects contractors order pre-mixed concrete, known as ready mix concrete, and this dominates sales with approximately 70% of the U.S cement use in 2014. However, approximately 4% of the U.S. cement sales in 2014 were through building materials dealers such as national chains such as Home Depot™, Lowes™, Payless Cashway™ etc. to local and regional building material suppliers. With a total U.S. cement market in 2014 of approximately 90 million metric tons this represents 3.6 million metric tons of cement sold in a range of bag sizes from 20 kg to just over 40 kg. Assuming 33.3 kg average bag weight this represents the equivalent of 30 bags per ton or approximately 110 million bags of cement. In addition to these cement sales there were also additional sales of bagged concrete and mortar on top of these figures.

These are used in a wide range of projects including residential and commercial structures subject to planning permission and other municipal/state/national requirements. However, whilst quality controls are applied by the manufacturers and constructors with ready mix concrete no such controls are generally applied when bag cement is used. This arises as, whilst testing techniques for concrete have evolved and will continue to evolve to meet requirements for faster construction, shorter durations of formwork use, and cost reductions, many of these techniques require samples be taken, fully extended curing of the concrete achieved, and laboratory measurements/testing performed. Typically, even the simple mechanical tests such as the slump test are not performed on site.

Accordingly, it would be beneficial to provide building owners, insurers, contractors, regulatory authorities, architects, and others with data regarding the cure and performance of concrete made on site with bagged cement or bagged concrete mixes. It would be further beneficial for the necessary measurements and calculations to be automatically performed with a self-contained data acquisition/logging module added to the concrete which wirelessly communicates to a portable electronic device during installation and/or during lifetime of the concrete structure formed.

It would be further beneficial for such automated testing/characterization using self-contained data acquisition/logging modules to be employed/compatible with other products during their manufacturing, deployment and lifetime.

Other aspects and features of the present invention will become apparent to those ordinarily skilled in the art upon review of the following description of specific embodiments of the invention in conjunction with the accompanying figures.

SUMMARY OF THE INVENTION

It is an object of the present invention to address limitations within the prior art relating concrete testing and concrete structure characterization, more particularly to electrical methods and systems for establishing cured concrete performance from measurements of wet concrete, automated methods and systems for periodic and/or continuous characterization of concrete structures, electrical methods and systems for corrosion measurement of rebar in reinforced concrete structures, construction material process monitoring and compact self-contained electrical sensors with wireless interfaces.

In accordance with an embodiment of the invention there is provided a method comprising:
providing an electrical measurement system for measuring an electrical characteristic of a concrete structure;
providing at least one beacon of a plurality of beacons, each beacon including a predetermined portion of a transceiver providing pulses of a predetermined format;
providing a global positioning system to provide a global position;
performing an electrical measurement of the electrical characteristic of a concrete structure;
determining at least a relative location of a plurality of relative locations, each relative location being that of the electrical measurement system relative to a predetermined subset of the plurality of beacons; and
storing the electrical measurement together with the plurality of relative locations and the global position.

In accordance with an embodiment of the invention there is provided a method comprising:
drilling a hole through the thickness of a covering to a layer of concrete forming a predetermined portion of a concrete structure;
filling the hole with a fluid which is electrically conductive;
connecting one end of an electrical measurement system for measuring an electrical characteristic of a concrete structure to the fluid and the other end to another part of the concrete structure; and
performing the electrical measurement.

In accordance with an embodiment of the invention there is provided a method comprising:
providing an electrical measurement system for measuring an electrical characteristic of a concrete structure;
generating with the electrical measurement system an electrical pulse which is applied to a first part of the concrete structure;
measuring with the electrical measurement system an output electrical signal with a probe applied to a second part of the concrete structure, the output electrical signal being the result of application of the electrical pulse to the first part of the concrete structure;
applying a predetermined signal processing algorithm to the output electrical signal to generate a low frequency electrical characteristic of the concrete structure.

In accordance with an embodiment of the invention there is provided a method comprising:
providing an electrical measurement system for measuring an electrical characteristic of a predetermined portion of concrete structure, the electrical measurement system comprising at least four probes, the inner pair of probes having a first predetermined spacing and the outer pair of probes having a second predetermined spacing;
generating with the electrical measurement system a plurality of applied electrical currents which are applied to a first part of the concrete structure via the outer pair of probes, the plurality of applied electrical currents being at a series of predetermined frequencies from a predetermined lower frequency limit to a predetermined upper frequency limit;
measuring with the electrical measurement system a plurality of output electrical voltages with the inner pair of probes, each of the plurality of output electrical voltages being at one of the predetermined frequencies;
applying a predetermined signal processing algorithm to the plurality of output electrical voltages to generate a frequency dependent electrical characteristic of the predetermined portion of concrete structure; and
determining an indication of corrosion for the predetermined portion of concrete structure in dependence upon at least the frequency dependent electrical characteristic.

In accordance with an embodiment of the invention there is provided a method comprising performing an electrical impedance measurement upon concrete and determining based upon at least the electrical impedance measurement a characteristic of the concrete.

In accordance with an embodiment of the invention there is provided a method comprising:

performing an electrical impedance measurement upon concrete;

determining based upon at least the electrical impedance measurement a characteristic of the concrete; wherein the electrical impedance measurement is adjusted in dependence upon the temperature at the time of the electrical impedance measurement with the adjustment comprising an activation energy established in dependence upon which characteristic of the concrete is being determined; and the characteristic of the concrete being at least one of:
determination of the water to cement ratio of the concrete;
estimation of in-situ compressive strength of the concrete after pouring;
prediction of at least one of 7-day, 28-day and 56-day compressive strength of the concrete;
detection of at least one of the initial and final setting time of the concrete;
assessment of a transport properties of the concrete selected from the group comprising permeability, diffusivity and porosity;
is the presence of a crack within the concrete; and
a change in the pore solution.

In accordance with an embodiment of the invention there is provided a method comprising:
performing an electrical impedance measurement upon wet concrete;
determining based upon at least the electrical impedance measurement a characteristic of the wet concrete; and
communicating either the characteristic of the wet concrete or a change to be made to the wet concrete.

In accordance with an embodiment of the invention there is provided a method comprising:
performing an electrical impedance measurement upon wet concrete within a framework;
determining based upon at least the electrical impedance measurement a characteristic of the wet concrete; and
adjusting the characteristics of a heating system at least one of attached to, in contact with, and forming part of the framework.

In accordance with an embodiment of the invention there is provided a method comprising:
performing electrical impedance measurements upon wet concrete as it is poured and/or dispensed;
transmitting the electrical impedance measurements to a remote server;
processing upon the remote server the electrical impedance measurements to determine a value for a characteristic of a plurality of characteristics of the wet concrete; and
communicating the characteristic of the wet concrete to a predetermined enterprise based upon at least one of the characteristic of a plurality of characteristics of the wet concrete and the determined value.

In accordance with an embodiment of the invention there is provided a method comprising method of determining a location of damage within a structure through mathematical processing of accelerometer data.

In accordance with an embodiment of the invention there is provided a method comprising:
providing at least one accelerometer of a plurality of accelerometers attached to a structure; exciting the structure in a predetermined manner;
receiving from the at least one accelerometer of the plurality of accelerometers data relating to acceleration of the structure during at least the excitation of the structure;
receiving excitation data relating to the excitation of the structure;

performing with a microprocessor a wavelet transformation process on the received data from the at least one accelerometer of the plurality of accelerometers in dependence upon at least the excitation data;
automatically with the microprocessor generating and storing in a non-volatile non-transitory memory at least one of a three-dimensional coefficient plot and a two-dimensional wavelet coefficient plot in dependence upon the output from the wavelet transformation process.

In accordance with an embodiment of the invention there is provided a method of determining at least one of a corrosion state and a depth of a rebar within reinforced concrete comprising providing four probes inline in contact with the reinforced concrete, applying a DC voltage to the outer pair of probes, measuring the time evolving potential difference across the inner pair of probes, and determining the at least one of the corrosion state and the depth of the rebar within the reinforced concrete in dependence upon at least the measured time evolved potential difference.

In accordance with an embodiment of the invention there is provided a device comprising:
a shell comprising an outer surface, a hollow interior, and a pair of outer electrical contacts disposed on the outer surface and coupled to a pair of inner electrical contacts on the interior of the shell;
an electrical circuit disposed within the shell and comprising a battery, a wireless transceiver, a memory, and a microprocessor;
a measurement circuit coupled to the microprocessor disposed within the shell coupled to the pair of inner electrical contacts and providing a predetermined electrical measurement of a characteristic of the environment adjacent to the pair of outer electrical contacts.

In accordance with an embodiment of the invention there is provided a method comprising:
storing data relating to properties of a first material within which a self-contained sensor device is to be disposed within the self-contained sensor device;
shipping the self-contained sensor device in association with either a second material for use in forming a mixture of the first material or the mixture of the first material;
deploying the self-contained sensor device in association with the mixture of the first material;
performing at least a measurement of a plurality of measurements upon the mixture of the first material with the self-contained sensor; and
determining based upon at least the measurement obtained with the self-contained sensor device a characteristic of the first material.

In accordance with the embodiment of the invention for the method the self-contained sensor device comprises:
a first predetermined portion of the construction material system comprising a first predetermined portion of a first material; and
a second predetermined portion of the construction material system comprising at least one self-contained sensor device of a plurality of self-contained sensor devices, each self-contained sensor device for performing at least one measurement of a plurality of measurements upon the first material; wherein
the first predetermined portion of the construction material system and the second predetermined portion of the construction material system are intended to be shipped to a predetermined location for deployment as part of a construction project.

In accordance with an embodiment of the invention there is method of establishing maturity data relating to a material being cured comprising:

establishing the electrical resistivity ($\rho_t$) of the material at a plurality of specific times (t); establishing the in-situ compressive strength ($S_t$) of the material at the plurality of specific times;

deriving c and d using $S_t = c + d \cdot \log(\rho_t)$;

substituting c and d into $$\frac{(a-c)}{d} = X_1 \text{ and } \frac{b}{d} = X_2$$

wherein $X_1$ and $X_2$ are coefficients obtained from regression analysis; and substituting into $S = a + b \cdot \log(M)$ to derive a prediction of the mature compressive strength M.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures, wherein:

FIGS. 4A to 4C depict system configurations for automatic location mapping of electrical measurements according to an embodiment of the invention;

FIGS. 6A and 6B depict system configurations for automatic location mapping of electrical measurements according to an embodiment of the invention addressing the issue of asphalt or tarmac covered concrete;

FIG. 28 depicts the prior art process of establishing maturity for concrete under ASTM C1074;

FIG. 29 depicts the periodic monitoring under ASTM C1074 wherein the maturity index is calculated at different strength testing times and the best curve fitted for the strength data versus maturity index data to obtain the maturity curve;

DETAILED DESCRIPTION

The present invention is directed to concrete testing and more particularly to electrical methods and systems for measuring rebar corrosion in reinforced concrete structures The ensuing description provides exemplary embodiment(s) only, and is not intended to limit the scope, applicability or configuration of the disclosure. Rather, the ensuing description of the exemplary embodiment(s) will provide those skilled in the art with an enabling description for implementing an exemplary embodiment. It being understood that various changes may be made in the function and arrangement of elements without departing from the spirit and scope as set forth in the appended claims.

A "portable electronic device" (PED) as used herein and throughout this disclosure, refers to a wireless device that requires a battery or other independent form of energy for power. This includes devices including, but not limited to, cellular telephone, smartphone, personal digital assistant (PDA), portable computer, pager, portable multimedia player, portable gaming console, laptop computer, tablet computer, and an electronic reader.

A "fixed electronic device" (FED) as used herein and throughout this disclosure, refers to a wired and/or wireless device used which is dependent upon a form of energy for power provided through a fixed network, e.g. an electrical mains outlet coupled to an electrical utilities network. This includes devices including, but not limited to, portable computer, desktop computer, computer server, Internet enabled display, mainframe, and server cluster. Such PEDs and FEDs supporting one or more functions and/or applications including, but not limited to, data acquisition, data storage, data analysis, communications, and Internet/Web interface.

Prior Art Concrete Testing

Figure 1:
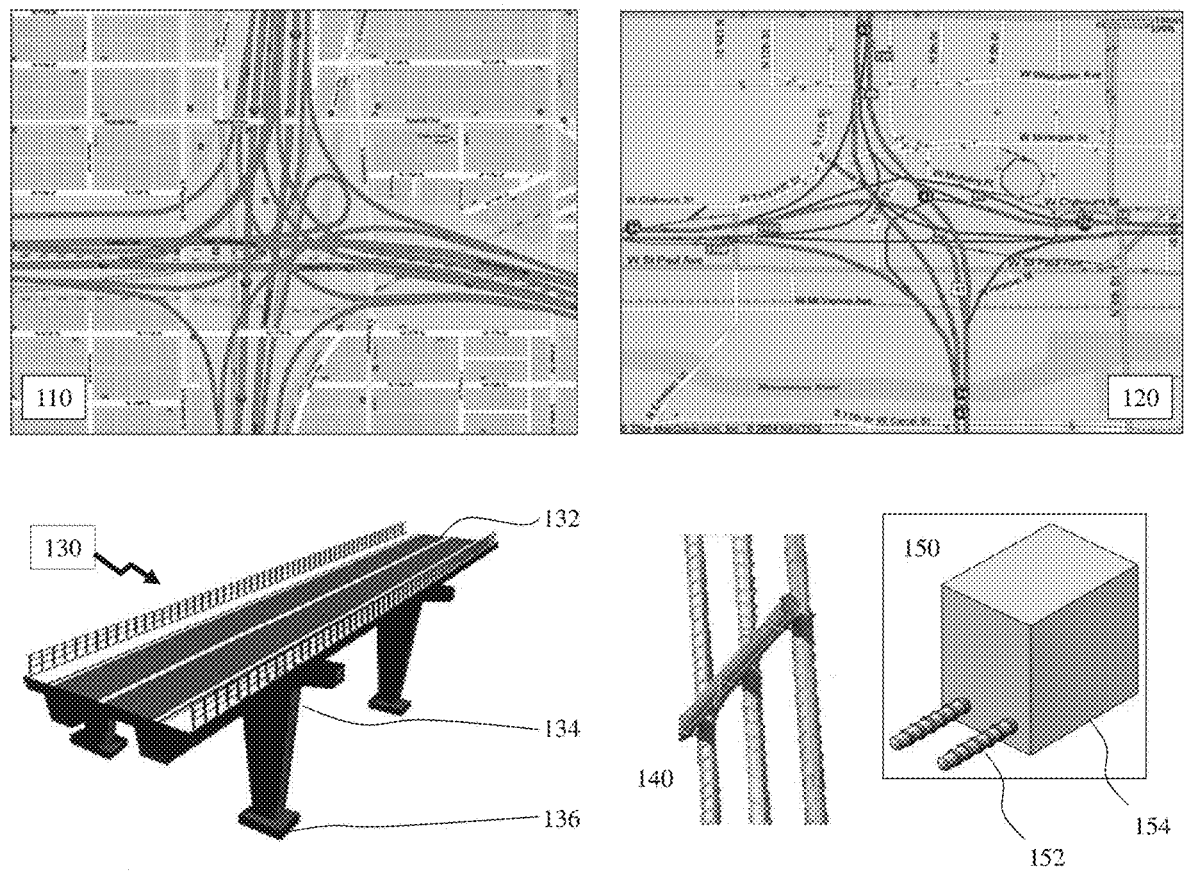
FIG. 1 depicts examples of concrete infrastructure that require characterization as well as rebar reinforced concrete.

Referring to FIG. 1 there are depicted first and second concrete infrastructures 110 and 120 which are the "Highway #1 Intersection 105 & 110" in Los Angeles, USA and "Marquette" Interchange in Milwaukee, USA respectively. Whilst perhaps overly dramatic these are just two of the 600,000 bridges and millions of buildings in the US requiring characterization for corrosion. These numbers represent just a fraction of those globally which require measurements to determine the corrosion levels of these infrastructure elements on a periodic basis.

Bridge structure 130 is a schematic of a bridge showing the road surface 132 together with supports 134 and foundation 132. All of these elements require characterization during the lifetime of the bridge structure 130 but typically the road surface 132 will be tested more frequently in areas where salt and other chemicals are used to address snow and ice on the surface during winter. Rebar schematic 140 shows a typical rebar configuration for reinforcing concrete wherein long rebar rods are employed along the axis experiencing tensile loading where their positions relative to each other prior to the concrete pour are maintained through tying other rods periodically along them as well as supporting these within the frame work into which the concrete will be poured to surround the rebars and form the concrete infrastructure. A schematic of such a structure is depicted in schematic 150 wherein the rebars 152 are embedded in the concrete 154.

Figure 2:
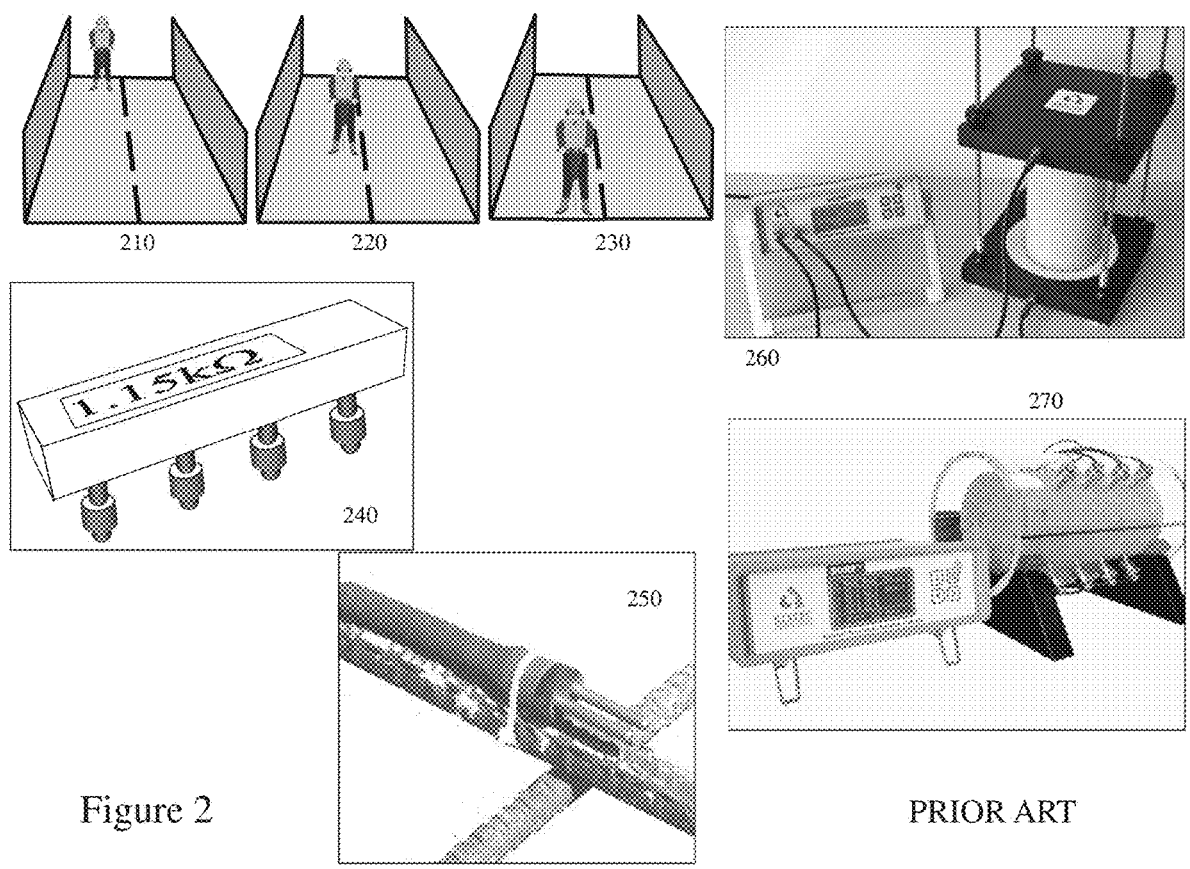
FIG. 2 depicts surface electrical resistivity measurements and embedded resistance probes according to the prior art.

Now referring to FIG. 2 there are depicted first to third images 210 through 230 respectively of surface electrical resistivity measurements according to the prior art. First to third images 210 through 230 respectively show a worker walking across a road surface performing measurements wherein they walk one pace, stop, make a measurement, walk another pace, stop, make a measurement. There is no reference to their position along the road surface and their position across the road whilst defined by the eroded white line at this point will be lost when the road surface is resurfaced, repainted, etc. Accordingly, these measurements are isolated, discrete measurements that cannot be correlated to any subsequent measurements taken in 1, 2, 3, or 5 years' time for example to determine structure changes. Equally, the data when taken away and analysed identifies an area of corrosion requiring correction through physical intervention. A work crew returning may be addressing a small area but without alignment to the physical structure the measurements provide no additional benefit and accordingly it is likely that the physical intervention will involve a substantial portion of the road surface. Likewise, a simple error in denoting which side of the road the measurements were made on results in the wrong side of the road surface being ripped up.

Fourth image 240 depicts a four-point Wenner probe as employed in surface electrical resistivity measurements such as those made by the worker in first to third images 210 through 230 respectively. It applies a 40 Hz AC electrical current from the outer pair of electrodes and measures the voltage between the inner pair of electrodes which is then converted to an electrical resistivity displayed on the screen and in the instance of first to third images 210 through 230 manually entered into a portable device by the work. Alternatively, rather than onsite measurements through such Wenner probes as depicted in fourth image 240 another approach is to exploit embedded sensors such as the one depicted in fifth image 250 may be employed. The probe depicted is a CORRATER Model 800 probe from Rohrback Cosasco Systems that measures the instantaneous corrosion rate of reinforcing steel in concrete by the method of linear polarization resistance (LPR). Each reading gives the instantaneous corrosion rate of the electrodes in the concrete environment, and the probes are monitored frequently or continuously to track changes in corrosion rate. However, these embedded sensors are expensive individually and deploying a matrix of them across say even a 100 m×10 m bridge prohibitive even without considering the additional complexities of interface cabling, measurement electronics etc. Accordingly, such embedded sensors tend to be used infrequently.

Also depicted are sixth and seventh images 260 and 270 respectively for electrical resistance measurements systems. Sixth image 260 depicts the Giatec RCON™ which is a non-destructive device for measuring the electrical resistivity of concrete specimens in the laboratory without any additional sample preparation requirements and allows measurements to be made on the same concrete samples that are currently used for the compressive strength testing of concrete. Seventh image 270 depicts Giatec Surf™ which is a laboratory test device for rapid, easy and accurate measurement of the surface electrical resistivity of concrete based on the four-probe (Wenner Array) technique.

Figure 3:
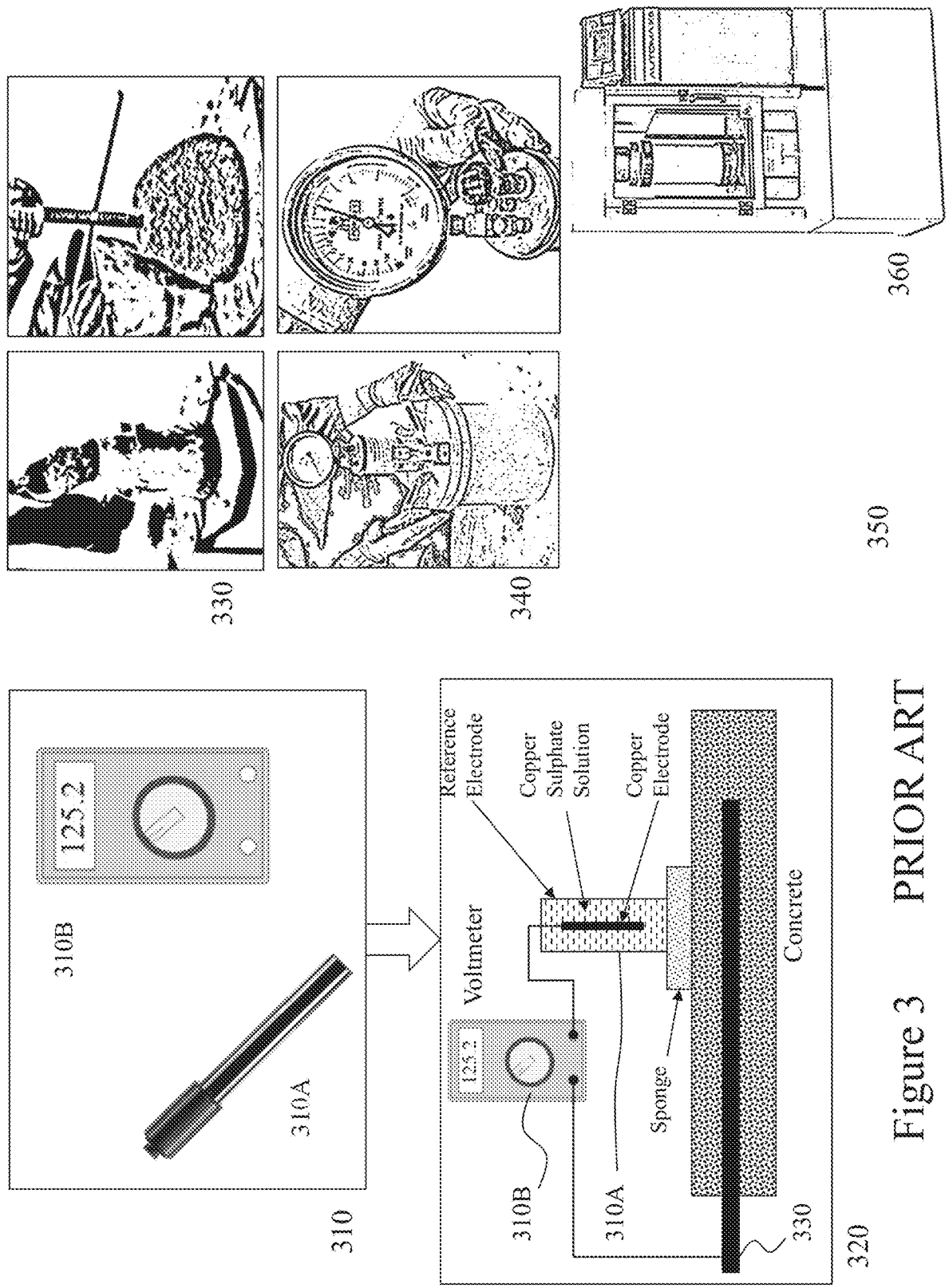
FIG. 3 depicts half-cell potential and surface resistivity measurements according to the prior art.

Referring to FIG. 3 there is depicted a half-cell potential meter 310 comprising a half-cell 310A and multimeter 310B which are depicted in deployment 320 are connected to each other via an interconnection cable. The other side of the multimeter 310A is electrically connected to the rebar 330 such that the electrical circuit for the multimeter 310A is completed via the rebar 330, the concrete and the half-cell 310A. Electrical contact of the half-cell 310A to the concrete is facilitated typically by the use of a wet sponge. As corrosion of reinforcing steel is an electro-chemical process then the behaviour of the steel can be characterized by measuring its half-cell potential where the greater the potential the higher the risk that corrosion is taking place. An electrode forms one half of the cell and the reinforcing steel in the concrete forms the other. A common reference electrode for site use is silver/silver chloride in potassium chloride solution although the copper/copper sulphate electrode is still widely used. It should be noted that the measured potential should be corrected relatively based on the type of electrode employed, concentration of electro-chemical half-cell 310A, pressure, and the temperature of the measurement. The survey procedure is firstly to locate the steel and determine the bar spacing using a cover meter, then the cover concrete is removed locally over a suitable bar and an electrical connection made to the steel. It is necessary to check that the steel is electrically continuous by measuring the resistance between two widely separated points. The reinforcing bar is connected to the half-cell via the multimeter 310B. Accordingly, this is a time-consuming process and mapping subject to the same issues as discussed supra in respect of FIG. 2 for the Wenner probe such as depicted in FIG. 2 with fourth image 240.

As noted supra these prior art electrical resistance measurements whilst easier to perform than the wet concrete tests are performed upon cured installed concrete infrastructure. Also noted supra standard wet concrete tests include slump test, air retention test, set time, and compressive strength. Examples of these test are depicted in FIG. 3 as:

slump test 330, with the cone filling and slump measurement stages depicted;
air retention test 340, with securing of the lid to the concrete filled bucket and measurement stages depicted;
set time 350, with a measurement depicted; and
compressive strength 360, with a measurement system depicted.

Electrical Measurements of Construction Material Properties

Figure 4A:
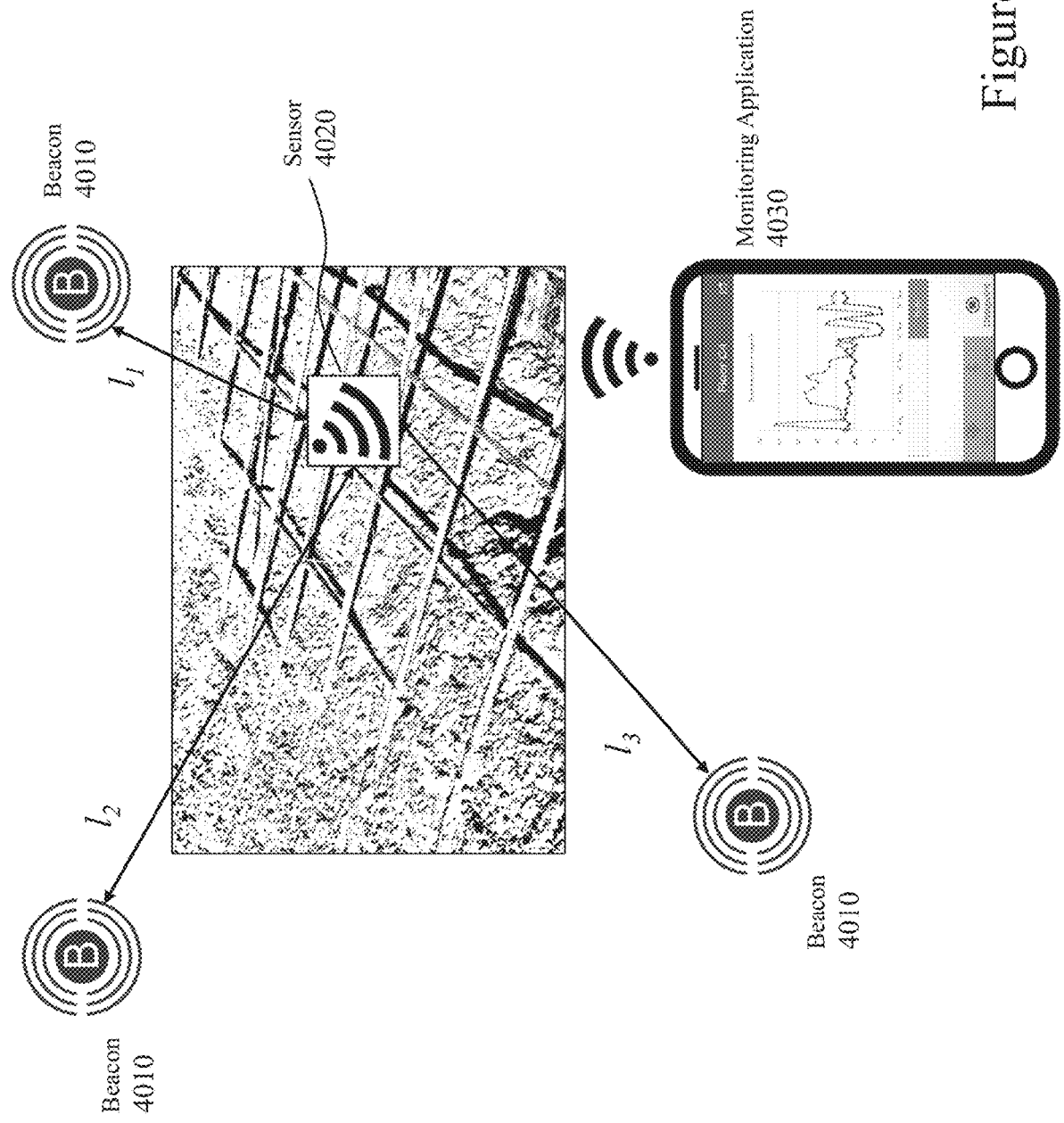

Now referring to FIG. 4A there is depicted a system configuration for automatic location mapping of electrical measurements according to an embodiment of the invention wherein a sensing device such as electrical test equipment (not depicted) or a sensor 4020 for example receives signals from a plurality of beacons 4010. As depicted the sensor 4020 is in wireless communication with a PED executing a monitoring application 4030 to extract data from the sensor 4020. In addition to the electrical measurements etc. performed by the sensor 4020 and data relating to the sensor 4020 itself the raw location data and/or processed location data with respect to the plurality of beacons 4010 may be transferred. In this manner the extracted data is geotagged to a specific location as well as a specific sensor. As described and depicted in respect of FIGS. 4B and 4C a variety of signaling and/or location techniques may be employed to establish the relative location of the sensor 4020 relative to the plurality of beacons 4010. One or more of the beacons 4020 may further incorporate a method to establish its location such as accessing global navigation satellite system (GNSS) signals or wireless triangulation to wireless base stations etc. which themselves establish their location via GNSS signals etc.

Figure 4B:
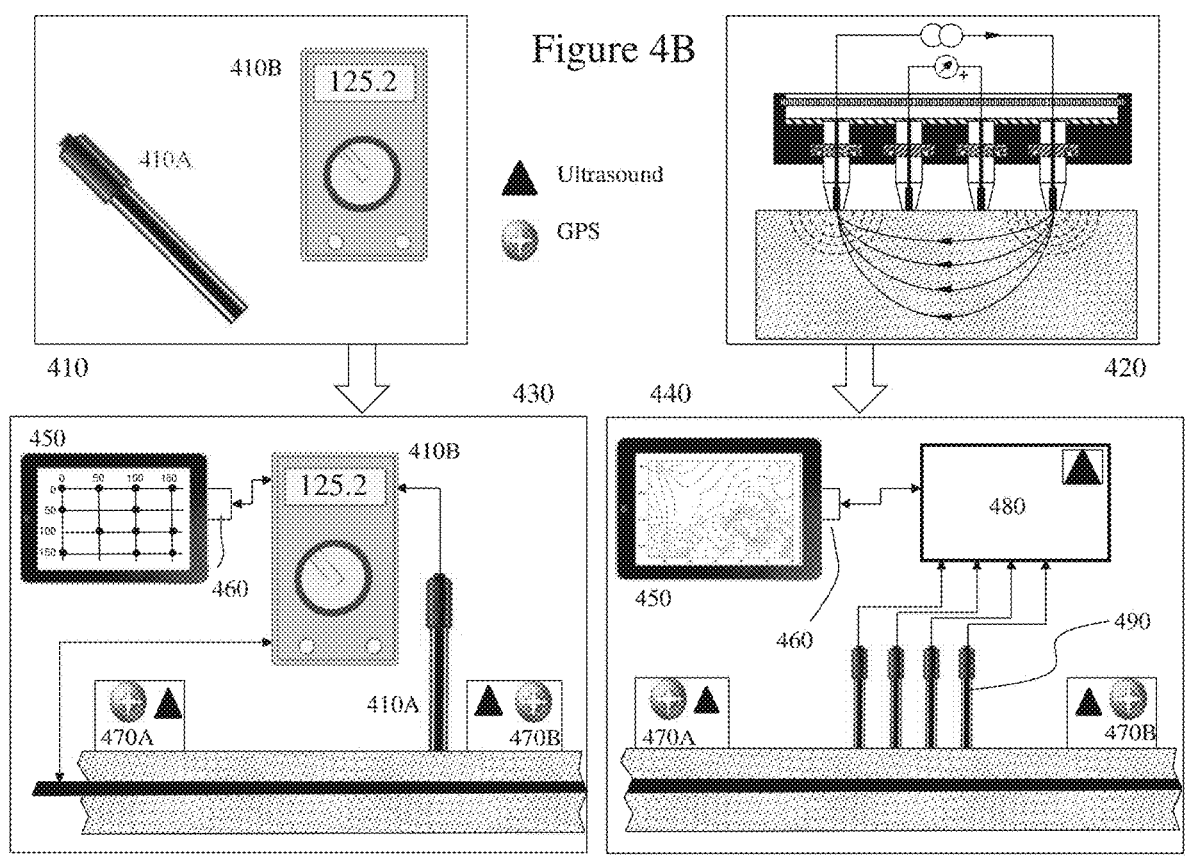

Referring to FIG. 4B there is depicted a system configuration for automatic location mapping of electrical measurements according to an embodiment of the invention. Whilst the embodiments of the invention are described primarily from the viewpoint of electrical measurements it would evident that the techniques may be applied to other test measurements, concrete test measurements, and other non-destructive tests (NDTs). Depicted are half-cell potential system (HCPS) 410 and surface electrical resistivity system (SERS) 420 as discrete devices and as first and second systems 430 and 440 respectively. In first system 430 the half-cell 410A and multimeter 410B are connected as previously described in respect of FIG. 3 and the electrical circuit is completed with the connection to the rebar. However, multimeter 410B is now in communication with a tablet PC 450 via an interface 460. The tablet PC 450 is also in communication with first and second beacons 470A and 470B which contain a GPS receiver and ultrasonic/radio frequency transmitter together with a wireless interface, not shown for clarity. Accordingly, the tablet PC 450 receives GPS data from each of the first and second beacons 470A and 470B as well as synchronizing the ultrasonic transducers. An ultrasonic receiver within multimeter 410B receives the ultrasonic signals from the ultrasonic transmitters allowing it to determine its distance from each of the first and second beacons 470A and 470B respectively. These distances are communicated to the tablet PC 450 allowing the location of each measurement to be automatically logged.

Likewise, in second system 440 the SERS 420 is depicted as meter 480 and probes 490. The meter 480 is again in communication with the tablet PC 450 via an interface 460 whilst the tablet PC 450 similarly receives GPS data from the first and second beacons 470A and 470B respectively. Similarly, the meter 480 contains an ultrasonic receiver such that the relative position of the meter relative to the first and second beacons 470A and 470B respectively can be determined. The addition of ultrasonic ranging, or another ranging technique, to augment the GPS location arises as the standard quoted accuracy of a low cost GPS receiver is approximately 15 meters (49 feet) and that even for high quality receivers according to the GPS Standard Positioning Service (SPS) it is currently approximately 3 meters (10 feet) (http://www.gps.gov/systems/gps/performance/accuracy/). However, with ranging the accuracy of location setting achieved by the inventors is less than 10 cm representing approximately two orders of magnitude improvement over GPS and other local positioning systems (LPS) based upon wireless signal triangulation, radio broadcast tower triangulation, and imaging with accuracies of the order of a meter.

It would be evident that in operation first and second systems 430 and 440 respectively would typically employ 3 beacons to remove ambiguities over position whilst they are described as having 2 beacons. Optionally, ultrasonic range determination may be replaced by other techniques including, but not limited to, visible optical, infrared optical, visible or infrared laser based optical, microwave, and radio frequency distance measurements. Optionally, other variants may include performing the distance determination within the beacons, obtaining GPS location from a GPS receiver within the meter, and that the connection between meter and tablet PC may be wireless as are the connections from the beacons to the tablet PC. Alternatively, the data logging, wireless interface etc. may be integrated within the meter eliminating the requirement for the separate tablet PC. Optionally, only one beacon may contain a GPS circuit.

Optionally, the GPS location, which may be considered a reference in some circumstances from which the secondary locations of the measurements points are determined may be replaced by another method of establishing a reference on the structure, including but not limited to architectural structures, foundations, brick/block walls, pavements, bridges/overpasses, and motorways/roads. Alternative methods may include, local positioning systems (LPSs) employing wireless techniques in conjunction with cellular base stations, Wi-Fi access points, and radio broadcast towers for example, establishing a predetermined point such as established by techniques such as surveying etc., or a predetermined distinctive point such as marker embedded into the structure. Accordingly, measurements may be established according to embodiments of the invention with references which are intrinsically linked (i.e. forming part of) or extrinsically linked (i.e. not forming part of) the structure and/or area being characterised and analysed. As such techniques may include a global positioning system, wireless triangulation, wireless multilateration, surveying from a survey reference point, and surveying from a predetermined point on the concrete structure. In some embodiments of the invention an initial reference point may be established and physically identified for subsequent periodic inspections. With location accuracies below 10 cm exploiting ranging techniques by the inventors it would be evident that periodic inspections are now feasible with overlaying subsequent corrosion maps to the original measurements.

Now referring to FIG. 4C there are depicted or configuration 4100 for automatic location mapping of electrical measurements according to an embodiment of the invention. As depicted in first configuration 4100 a user has a tablet 4120, upon a GoPad™ halter/holder, and a Giatec Cell™ 4110 which is a maintenance-free half-cell sensor that measures the corrosion potential and transmits this to the tablet for generating half-cell contour plots, i.e. corrosion maps 4400 in real-time. The user when making measurements can enter into the tablet 4120 which measurement they are making as depicted with entry grid 4300 wherein each measurement indicated as completed is denoted by a circle on the grid. Based upon the grid measurements made the corrosion map 4400 may be generated in real-time and shared in real-time with a remote engineering office through wireless communications of the tablet 4120 to a wireless network. Hence it would be evident that the Giatec Cell™ 4110 significantly reduces the labor cost associated with the data collection as well as simplifying and de-skilling it whilst automating the subsequent contour plot generation and reporting using software installed upon the tablet 4110. Giatec Cell™ 4110 includes a Bluetooth™ transceiver allowing the data to be sent to the tablet 4110 wirelessly. The cable 4130 represents the electrical connection to a rebar within the infrastructure such as described supra in respect of FIGS. 3 and 4B.

Figure 5:
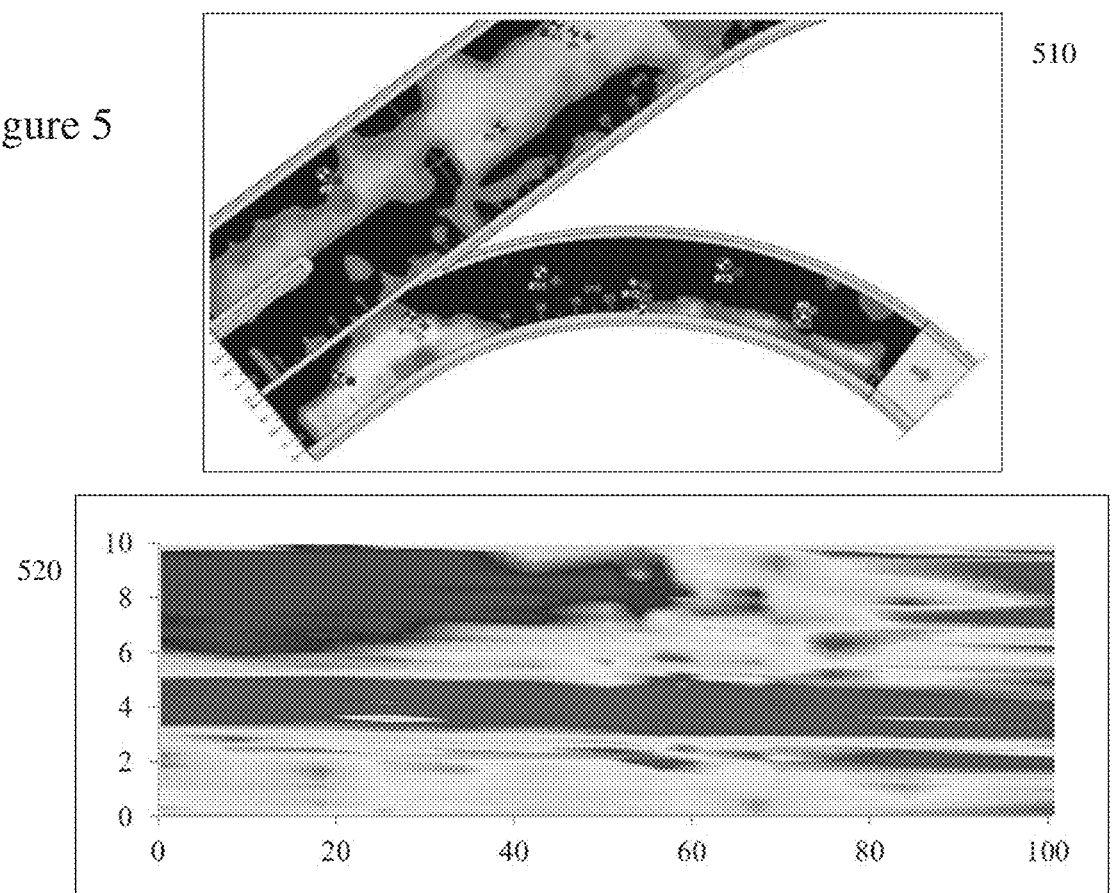
FIG. 5 depicts examples of concrete infrastructure mapping established according to embodiments of the invention.

Accordingly, using a test system, such as one of first and second systems 430 and 440 respectively in FIG. 4B or configuration 4100 in FIG. 4C, an operator may establish a plurality of measurements across a concrete surface wherein the location of the test system is automatically determined relative to the beacons and a GPS location such that these results can then be processed to generate first and second contour maps 510 and 520 as depicted in FIG. 5. Accordingly, during testing an operator may perform measurements using a system such as described supra in respect of first and second systems 430 and 440 respectively in FIG. 4B or configuration 4100 in FIG. 4C in combination with the software upon the tablet 4110 which contains in addition to the software for managing the data acquisition and plotting data relating to the region or regions of an element of concrete infrastructure which is to be tested and present these sequentially to the user. Alternatively, the results from multiple test systems with multiple operators may be combined based upon the location data of the measurements. These multiple systems may operate with a single set of beacons or multiple test systems may be associated with multiple sets of beacons.

Figure 6A:
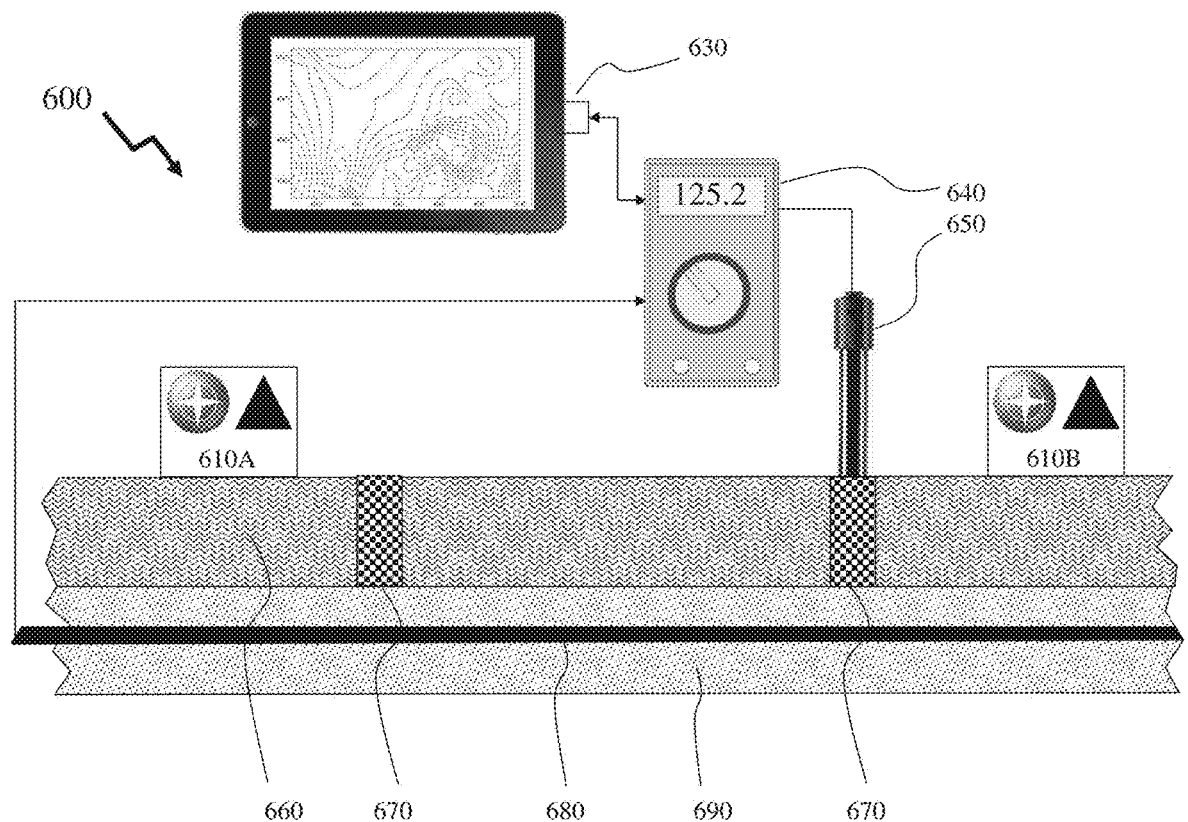

Now referring to FIG. 6A there is depicted a system configuration 600 for automatic location mapping of electrical measurements according to an embodiment of the invention addressing the issue of asphalt or tarmac covered concrete. The measurement of steel corrosion potential inside concrete directly below the surface0020 of an insulating material such as asphalt or tarmac is not possible. However, as evident in system configuration 600 the tablet PC 620 and interface 630 are coupled to the meter 640 and half-cell 650. Also depicted are first and second beacons 610A and 610B respectively. Also depicted are concrete 690, rebar 680, and asphalt 660. The technique comprises drilling holes 670 that drilled into the asphalt layer 660 to reach the surface of the concrete 690. These holes are then filled with a conductive gel or liquid to create an electrically conductive pathway from the half-cell 650 to the surface of the concrete allowing the corrosion potential of the rebar 680 to be measured. Accordingly, drilling multiple holes 670 allow for the mapping and/or discrete measurements on a concrete structure such as described supra in respect of FIGS. 4A to 5 respectively.

In contrast considering FIG. 6B there is depicted a system configuration 6000 for automatic location mapping of electrical measurements according to an embodiment of the invention. As depicted first to third infrastructure elements 6600A to 6600C with concrete and rebar construction are depicted within which first to third contacts 6300A to 6300C have been made to the rebars within. In respect of the rebar in the first infrastructure element 6600A the first contact 6300A is connected via cable 6400 to wireless half-cell 6500 wherein the resulting measurement is wirelessly transmitted to computer 6200. The position of wireless half-cell 6500 is established in dependence upon beacons 6100A to 6100C respectively which include both GPS and ultrasound elements although a combination of other optical, wireless, and microwave location and/or ranging techniques may be employed. Subsequently, prior to, or concurrent with measurements made with wireless half-cell 6500 its location is established in dependence upon at least first to third beacons 6100A to 6100C, and others potentially, such that the location of wireless half-cell 6500 is established in three-dimensions (3D) although as time is also established it may be considered as established in four-dimensions (4D) potentially. Accordingly, the wireless half-cell 6500 may depending upon which of first to third contacts 6300A to 6300C it is contacted to perform measurements upon first to third infrastructure elements 6600A to 6600C wherein based upon first to third beacons 6100A to 6100C and others, not shown for clarity, the 3D position of the wireless half-cell 6500 may be determined and its measurements communicated to computer 6200 for storage and/or communication via a network to a remote storage and/or analysis location. Through repeated measurements the first to third infrastructure elements 6600A to 6600C may be characterised with 3D mapping with the accuracy of 10 cm or less based upon the combination, for example, of ultrasound ranging with GPS location.

Figure 7:
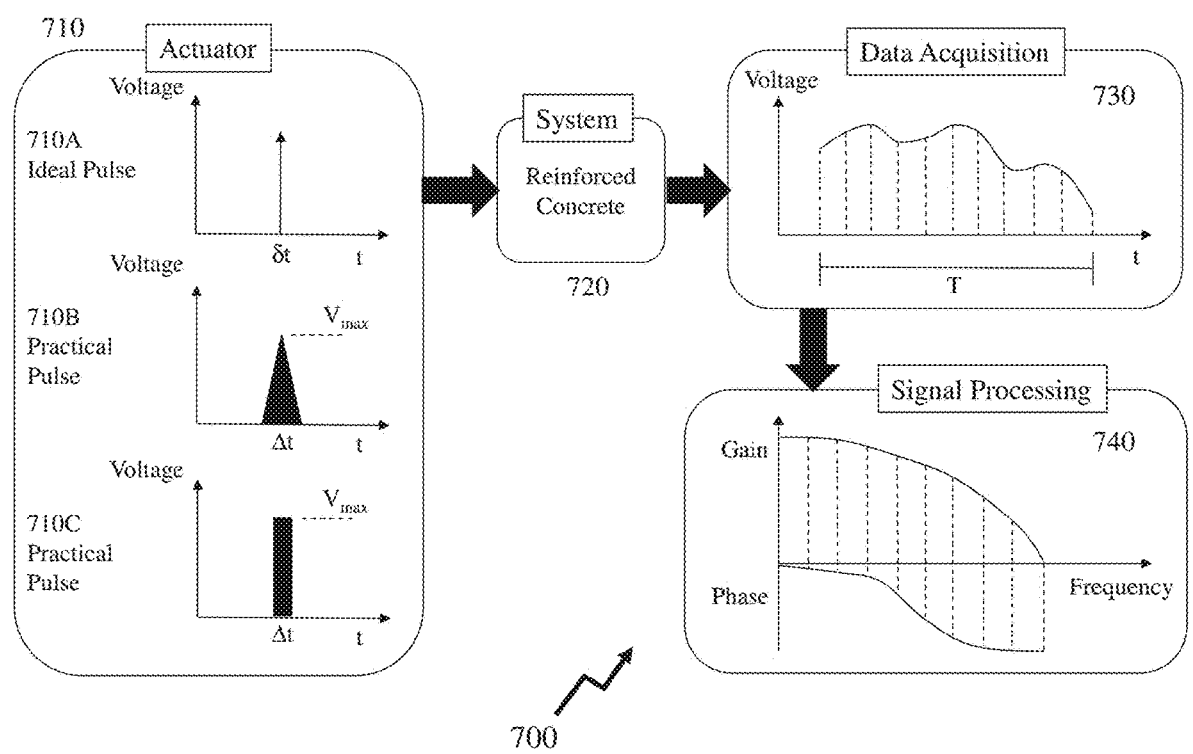
FIG. 7 depicts a schematic of pulsed electrical measurements according to an embodiment of the invention.

The low-frequency impedance of rebar in concrete can be correlated to the corrosion state of reinforcement in concrete. However, direct measurement of the low-frequency impedance of rebar in concrete is very time-consuming and vulnerable to noise interruption as discussed supra; hence it is not practical to use this technique in the field to measure the corrosion rate of rebar inside the concrete. Accordingly, within this innovative technique, the low-frequency behaviour of the steel rebar contact surface is determined by applying a narrow DC current pulse, or a DC step voltage, for a short period of time and recording the voltage of the system with a very high sampling rate. The highly sampled recorded voltage change is then processed to determine the low-frequency impedance of the rebar in concrete, which can be used to determine the state of corrosion in reinforced concrete structures. This process is schematically shown in FIG. 7 wherein a first step, the actuator 710, is depicted as ideal pulse 710 together with first and second practical pulses 710B and 710C respectively, which is then applied to the reinforced concrete. The resulting output voltage profile is depicted in data acquisition step 730 together with the subsequent signal processing step 740 wherein plots of gain and phase versus frequency, for example, are derived as a function of frequency allowing the low frequency characteristics of the rebar in concrete to be determined.

According to other embodiments of the invention a single pulse may be applied to multiple rebar elements simultaneously and received with multiple detectors disposed across the concrete structure being characterized. Optionally, the current pulse may be induced into the rebar without electrical contact through electromagnetic induction for example.

Figure 8:
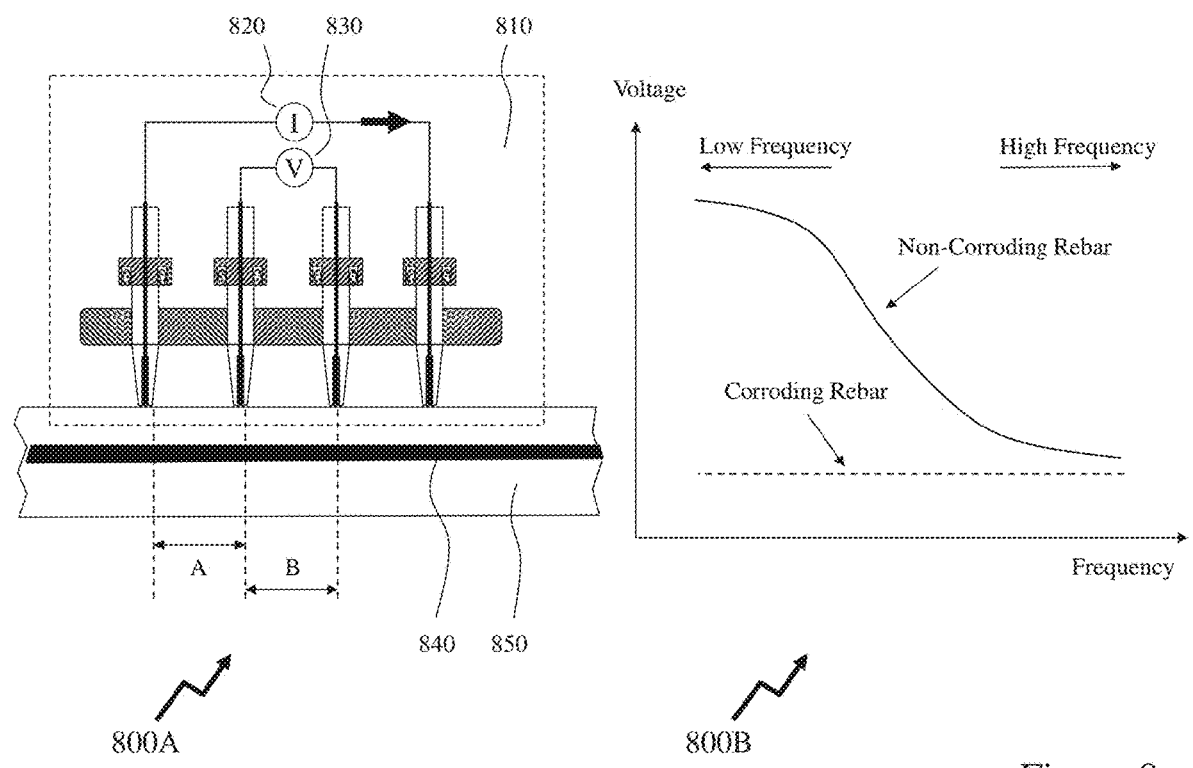
FIG. 8 depicts electrical characterization of a rebar within concrete without electrical connection to the rebar according to an embodiment of the invention.

FIG. 8 depicts electrical characterization of a rebar within concrete without electrical connection to the rebar according to an embodiment of the invention wherein the electrical response of rebar inside the concrete is determined from the surface of the concrete with four probes as shown in first image 800A of FIG. 8. A constant AC current is applied between the outer probes and the voltage between the inner probes is measured, such as discussed supra in respect of prior art 4-point Wenner probes for surface electrical resistivity measurements which operate at a single frequency, for example 40 Hz. However, the inventors have found that by sweeping the frequency of the AC current from high frequency to low frequency and recording the voltage of the measurement system, as illustrated schematically in second image 800B in FIG. 8, that the voltage response of the corroding rebar is different from that of a non-corroding rebar.

As depicted the voltage for a non-corroding rebar varies decreasing from the low frequency zone of the plot towards the high frequency zone, but it is almost invariable for the corroding rebar. Accordingly, using a swept frequency AC source and a fast voltage measurement system it is possible to detect the corroding areas of the reinforced concrete structures from the surface of the concrete with no requirement to provide have an electrical connection to the rebar inside the concrete, unlike other prior art non-destructive test techniques.

Figure 9:
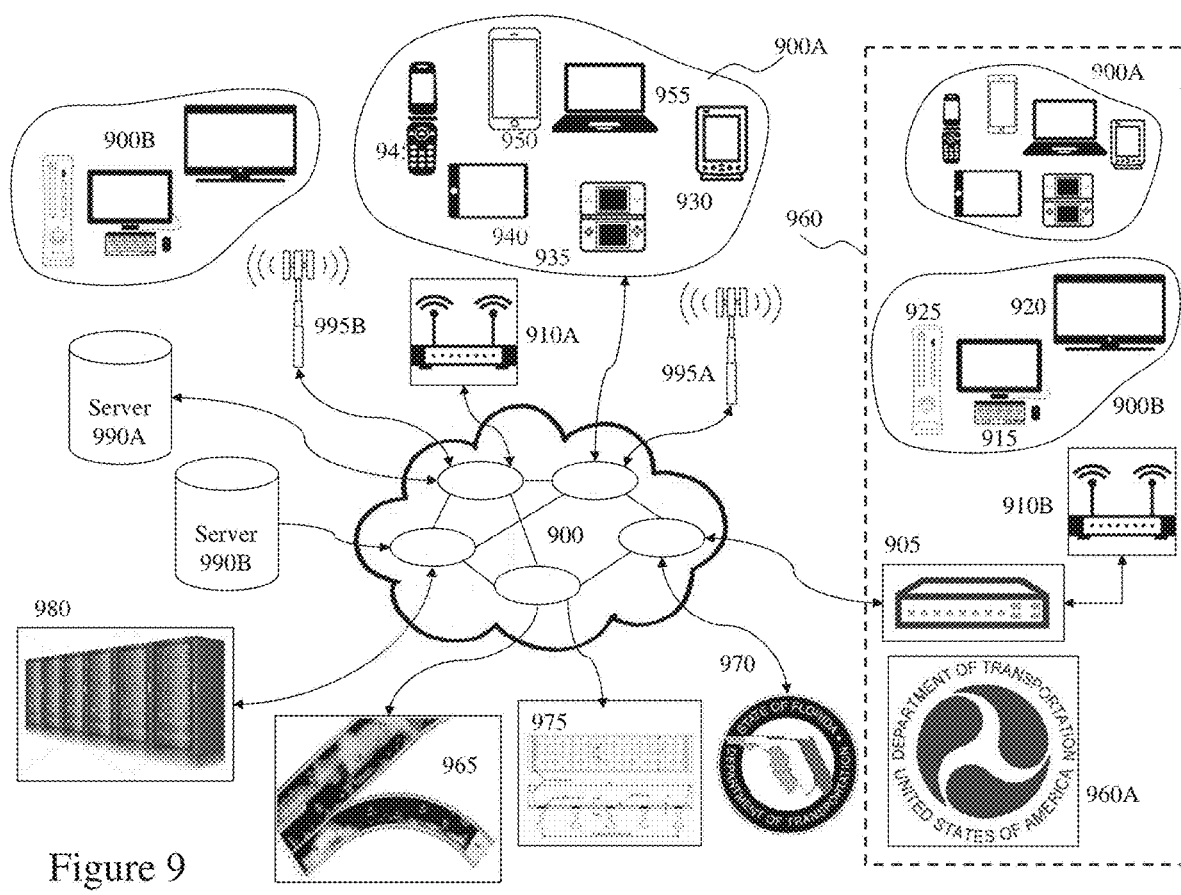
FIG. 9 depicts a network supporting communications to and from electronic devices implementing contextual based UIs according to embodiments of the invention.

Exemplary Network and Device Configurations for Construction Material Characterisation Now referring to FIG. 9 there is depicted network 900 supporting communications to and from electronic devices implementing contextual based UIs according to embodiments of the invention. As shown first and second user groups 900A and 900B respectively interface to a telecommunications network 900. Within the representative telecommunication architecture, a remote central exchange 980 communicates with the remainder of a telecommunication service providers network via the network 900 which may include for example long-haul OC-48/OC-192 backbone elements, an OC-48 wide area network (WAN), a Passive Optical Network, and a Wireless Link. The central exchange 980 is connected via the network 900 to local, regional, and international exchanges (not shown for clarity) and therein through network 900 to first and second wireless access points (AP) 995A and 995B respectively which provide Wi-Fi cells for first and second user groups 900A and 900B respectively. Also connected to the network 900 are first and second Wi-Fi nodes 910A and 910B, the latter of which being coupled to network 900 via router 905. Second Wi-Fi node 910B is associated with Government Body 960A and environment 960 within which are first and second user groups 900A and 900B. Second user group 900B may also be connected to the network 900 via wired interfaces including, but not limited to, DSL, Dial-Up, DOCSIS, Ethernet, G.hn, ISDN, MoCA, PON, and Power line communication (PLC) which may or may not be routed through a router such as router 905.

Within the cell associated with first AP 910A the first group of users 900A may employ a variety of portable electronic devices including for example, laptop computer 955, portable gaming console 935, tablet computer 940, smartphone 950, cellular telephone 945 as well as portable multimedia player 930. Within the cell associated with second AP 910B are the second group of users 900B which may employ a variety of fixed electronic devices including for example gaming console 925, personal computer 915 and wireless/Internet enabled television 920 as well as cable modem 905.

Also connected to the network 900 are first and second APs which provide, for example, cellular GSM (Global System for Mobile Communications) telephony services as well as 3G and 4G evolved services with enhanced data transport support. Second AP 995B provides coverage in the exemplary embodiment to first and second user groups 900A and 900B. Alternatively the first and second user groups 900A and 900B may be geographically disparate and access the network 900 through multiple APs, not shown for clarity, distributed geographically by the network operator or operators. First AP 995A as show provides coverage to first user group 900A and environment 960, which comprises second user group 900B as well as first user group 900A. Accordingly, the first and second user groups 900A and 900B may according to their particular communications interfaces communicate to the network 900 through one or more wireless communications standards such as, for example, IEEE 802.11, IEEE 802.15, IEEE 802.16, IEEE 802.20, UMTS, GSM 850, GSM 900, GSM 1800, GSM 1900, GPRS, ITU-R 5.138, ITU-R 5.150, ITU-R 5.280, and IMT-2000. It would be evident to one skilled in the art that many portable and fixed electronic devices may support multiple wireless protocols simultaneously, such that for example a user may employ GSM services such as telephony and SMS and Wi-Fi/WiMAX data transmission, VOIP and Internet access. Accordingly, portable electronic devices within first user group 900A may form associations either through standards such as IEEE 802.15 and Bluetooth as well in an ad-hoc manner.

Also connected to the network 900 are concrete mapping environment 965, State Body 970, and Bridge Structure environment 975 as well as first and second servers 990A and 990B which together with others not shown for clarity, may host according to embodiments of the inventions multiple services associated with one or more organizations, including but not limited to, a provider of the software operating system(s) and/or software application(s) associated with the electronic device(s), a provider of the electronic device, provider of one or more aspects of wired and/or wireless communications, provider of the electrical measurement devices, provider of mapping analysis software, provider of electrical measurement analysis software, global position system software, materials databases, building databases, regulatory databases, license databases, construction organizations, websites, and software applications for download to or access by FEDs, PEDs, and electrical measurement systems. First and second servers 990A and 990B may also host for example other Internet services such as a search engine, financial services, third party applications and other Internet based services.

Accordingly, it would be evident to one skilled in the art that electrical measurement systems and/or concrete corrosion analysis according to embodiments of the invention described supra in respect of FIGS. 4 through 8 may be connected to a communications network such as network 900 either continuously or intermittently. It would be further evident that the electrical resistivity measurements of concrete and/or rebar together with the analysis of the measurements and their mapping may be triggered as a result of activities triggered by, for example, the Government Body 960A and/or State Body 970 in order to address regulatory requirements, safety concerns etc.

Accordingly, the engineers, workers and/or technicians who will be performing the measurements may be able to access Bridge Structure Environment 975 to obtain architect drawings, engineering data, design data, etc. relating to the concrete structure being assessed. It would be evident that other databases addressing other environments such as for example, shopping malls, road surfaces, public walkways, residential housing, and commercial buildings may be accessed where the requirements for assessment relate to these structures and the regulatory bodies may be similarly transportation or include others such as Department of Housing, Federal Highway Department, and Bureau of Industry and Security. Where all or part of the structure being assessed has been previously assessed then data may be retrieved from the Concrete Mapping Environment for example. It would be evident that with coordinated based measurement acquisition that an engineer may view in real time a contour map of the structure being assessed as the data is acquired and accordingly may ask for additional measurements or repeated measurements to be performed. Additionally, previous contour mapping and electrical measurements may allow for targeted re-assessment of areas of concern at a different frequency to that of the overall structure.

Figure 10:
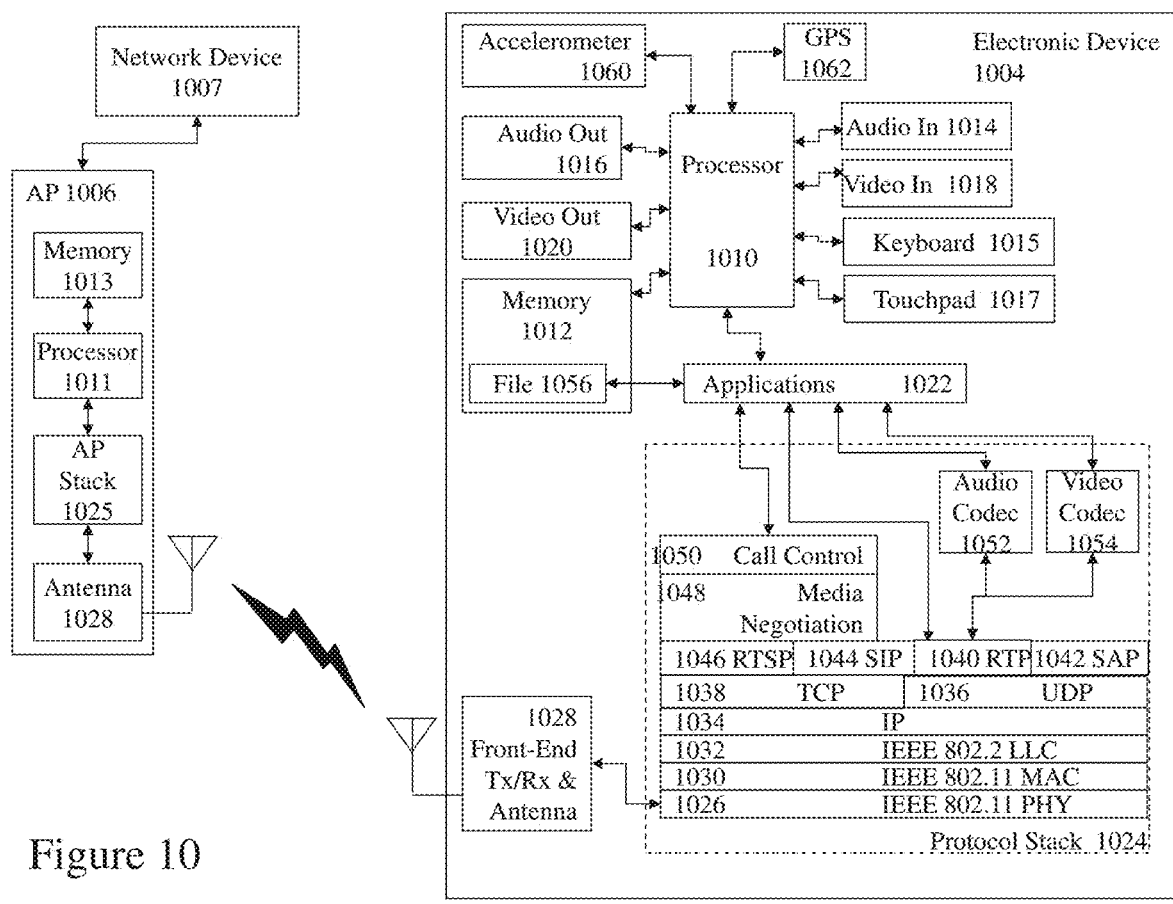
FIG. 10 depicts an electronic device and network access point supporting contextual based UIs according to embodiments of the invention.

FIG. 10 there is depicted an electronic device 1004 and network access point 1007 supporting contextual based UIs according to embodiments of the invention. Electronic device 1004 may for example be a portable electronic device or a fixed electronic device and may include additional elements above and beyond those described and depicted. Also depicted within the electronic device 1004 is the protocol architecture as part of a simplified functional diagram of a system 1000 that includes an electronic device 1004, such as a smartphone 955, an access point (AP) 1006, such as first AP 910, and one or more network devices 1007, such as communication servers, streaming media servers, and routers for example such as first and second servers 990A and 990B respectively. Network devices 1007 may be coupled to AP 1006 via any combination of networks, wired, wireless and/or optical communication links such as discussed above in respect of FIG. 9. The electronic device 1004 includes one or more processors 1010 and a memory 1012 coupled to processor(s) 1010. AP 1006 also includes one or more processors 1011 and a memory 1013 coupled to processor(s) 1011. A non-exhaustive list of examples for any of processors 1010 and 1011 includes a central processing unit (CPU), a digital signal processor (DSP), a reduced instruction set computer (RISC), a complex instruction set computer (CISC) and the like. Furthermore, any of processors 1010 and 1011 may be part of application specific integrated circuits (ASICs) or may be a part of application specific standard products (ASSPs). A non-exhaustive list of examples for memories 1012 and 1013 includes any combination of the following semiconductor devices such as registers, latches, ROM, EEPROM, flash memory devices, non-volatile random access memory devices (NVRAM), SDRAM, DRAM, double data rate (DDR) memory devices, SRAM, universal serial bus (USB) removable memory, and the like.

Electronic device 1004 may include an audio input element 1014, for example a microphone, and an audio output element 1016, for example, a speaker, coupled to any of processors 1010. Electronic device 1004 may include a video input element 1018, for example, a video camera, and a video output element 1020, for example an LCD display, coupled to any of processors 1010. Electronic device 1004 also includes a keyboard 1015 and touchpad 1017 which may for example be a physical keyboard and touchpad allowing the user to enter content or select functions within one of more applications 1022. Alternatively, the keyboard 1015 and touchpad 1017 may be predetermined regions of a touch sensitive element forming part of the display within the electronic device 1004. The one or more applications 1022 that are typically stored in memory 1012 and are executable by any combination of processors 1010. Electronic device 1004 also includes accelerometer 1060 providing three-dimensional motion input to the process 1010 and GPS 1062 which provides geographical location information to processor 1010.

Electronic device 1004 includes a protocol stack 1024 and AP 1006 includes a communication stack 1025. Within system 1000 protocol stack 1024 is shown as IEEE 802.11 protocol stack but alternatively may exploit other protocol stacks such as an Internet Engineering Task Force (IETF) multimedia protocol stack for example. Likewise, AP stack 1025 exploits a protocol stack but is not expanded for clarity. Elements of protocol stack 1024 and AP stack 1025 may be implemented in any combination of software, firmware and/or hardware. Protocol stack 1024 includes an IEEE 802.11-compatible PHY module 1026 that is coupled to one or more Front-End Tx/Rx & Antenna 1028, an IEEE 802.11-compatible MAC module 1030 coupled to an IEEE 802.2-compatible LLC module 1032. Protocol stack 1024 includes a network layer IP module 1034, a transport layer User Datagram Protocol (UDP) module 1036 and a transport layer Transmission Control Protocol (TCP) module 1038.

Protocol stack 1024 also includes a session layer Real Time Transport Protocol (RTP) module 1040, a Session Announcement Protocol (SAP) module 1042, a Session Initiation Protocol (SIP) module 1044 and a Real Time Streaming Protocol (RTSP) module 1046. Protocol stack 1024 includes a presentation layer media negotiation module 1048, a call control module 1050, one or more audio codecs 1052 and one or more video codecs 1054. Applications 1022 may be able to create maintain and/or terminate communication sessions with any of devices 1007 by way of AP 1006. Typically, applications 1022 may activate any of the SAP, SIP, RTSP, media negotiation and call control modules for that purpose. Typically, information may propagate from the SAP, SIP, RTSP, media negotiation and call control modules to PHY module 1026 through TCP module 1038, IP module 1034, LLC module 1032 and MAC module 1030.

It would be apparent to one skilled in the art that elements of the electronic device 1004 may also be implemented within the AP 1006 including but not limited to one or more elements of the protocol stack 1024, including for example an IEEE 802.11-compatible PHY module, an IEEE 802.11-compatible MAC module, and an IEEE 802.2-compatible LLC module 1032. The AP 1006 may additionally include a network layer IP module, a transport layer User Datagram Protocol (UDP) module and a transport layer Transmission Control Protocol (TCP) module as well as a session layer Real Time Transport Protocol (RTP) module, a Session Announcement Protocol (SAP) module, a Session Initiation Protocol (SIP) module and a Real Time Streaming Protocol (RTSP) module, media negotiation module, and a call control module.

Portable and fixed electronic devices represented by electronic device 1004 may include one or more additional wireless or wired interfaces in addition to the depicted IEEE 802.11 interface which may be selected from the group comprising IEEE 802.15, IEEE 802.16, IEEE 802.20, UMTS, GSM 850, GSM 900, GSM 1800, GSM 1900, GPRS, ITU-R 5.138, ITU-R 5.150, ITU-R 5.280, IMT-2000, DSL, Dial-Up, DOCSIS, Ethernet, G.hn, ISDN, MoCA, PON, and Power line communication (PLC).

Accordingly, it would be evident to one skilled in the art that the electronic device 1004 may be, for example, the tablet PC 450 in FIG. 4 or the multimeter 410B and/or meter 480 in FIG. 4 wherein the wireless network access, GPS, etc. form part of these electrical measurements systems rather than a separate PED. Alternatively, electronic device 1004 may be a PED wirelessly interconnected to the electrical measurement system allowing an on-site engineer for example to view the contour mapping and/or electrical data in real time as well as accessing the other information resources such as described above in respect of FIG. 9. Accordingly, an on-site engineer can decide on taking more measurements from a particular location and make immediate suggestions about the safety of the reinforced concrete structure.

In-Situ Electrical Measurements of Construction Material Properties

Electrical impedance method for in-situ measuring and monitoring of concrete properties would be beneficial in order to simplify testing procedures, reduce the time taken to perform tests, allow for increased sampling rates, reduce errors, and reduce time before issues are identified with concrete delivered that is out of specification.

As the electrical impedance of concrete can be simply related to the pore network characteristics of concrete such as pore size and their connectivity, moisture content in the pores and pore solution chemistry and in general the microstructure of concrete. The electrical impedance of concrete at certain ranges of frequency therefore, according to embodiments of the invention, has been well correlated with important early-stage properties of concrete such that a variety of properties may be established including:

Determination of water to cement ratio of concrete;
Estimation of in-situ compressive strength of concrete after pouring;
Prediction of 7-day, 28-day and 56-day compressive strength of concrete (ASTM C39)
Detection of initial and final setting of concrete (ASTM C403);
Assessment of transport properties of concrete such as permeability, diffusivity and porosity (ASTM C1202, ASTM C1543);
Crack detection; and
Detection of changes in the pore solution.

Determination of Water to Cement Ratio of Concrete: The measurement of water to cement ratio of concrete before or during pouring the concrete is critically important in the construction industry to ensure the appropriate quality of the concrete delivered by concrete trucks to the construction site. The water/cement ratio is a parameter that is specified for a concrete mixture. Higher water content increases the porosity of the hardened concrete and thus decreases its strength and durability but low water content, in contrast, decreases the workability of concrete. So, it is important to have just enough water in the concrete mixture. Whilst the amount of water within the concrete truck may be known when it leaves the concrete supplier's facility what it is by the time it is poured depends upon a variety of factors, including but not limited to, ambient temperature, time period between mixing and pouring, and additional water added by the truck driver/contractor etc. during transit and at the construction site. Accordingly, monitoring the water/cement ratio in real-time beneficially provides concrete suppliers, builders, owners, regulators, etc. with enhanced data which can be archived, accessed, analysed, etc. subsequently as well as avoiding pouring low-quality concrete, the replacement of which will be very costly and, in some cases, impossible.

Figure 11:
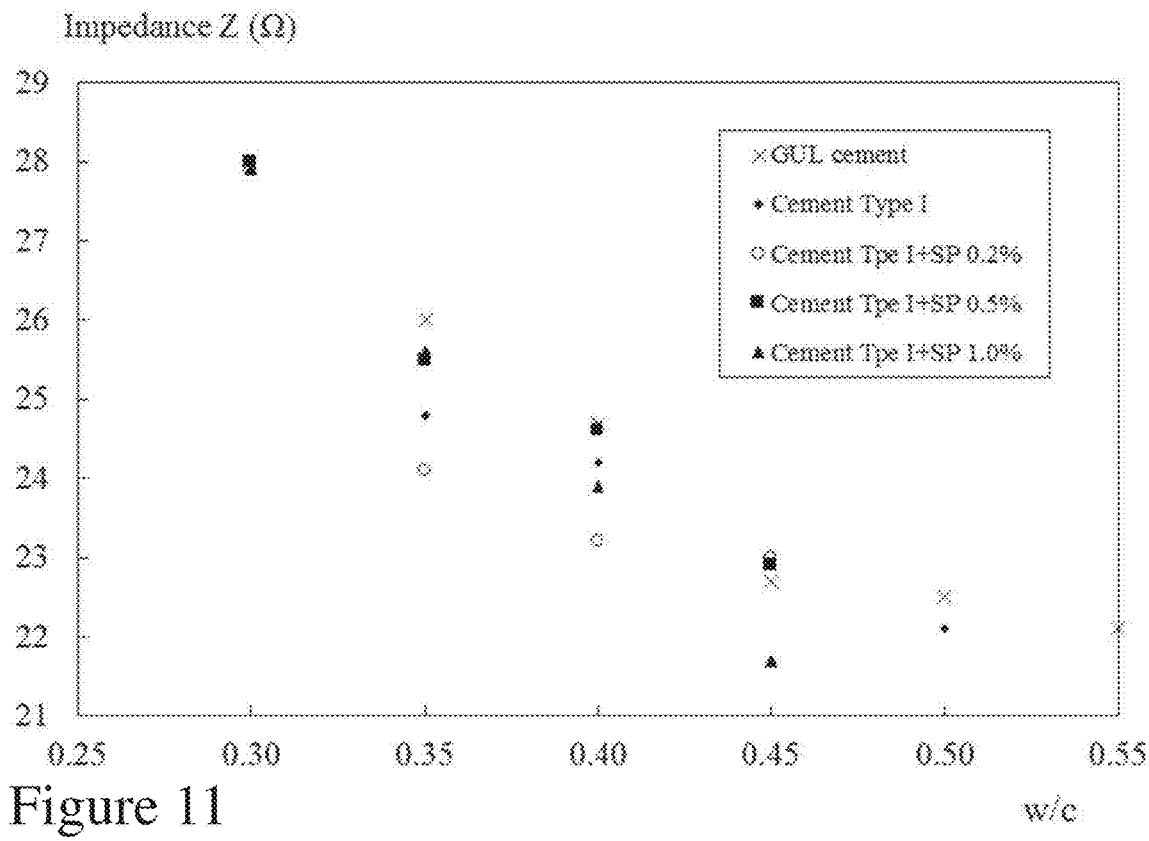
FIG. 11 depicts the estimation of water to cement ratio using electrical impedance data according to an embodiment of the invention.

Accordingly, referring to FIG. 11 there is depicted the estimated water content from electrical impedance data by the inventors according to an embodiment of the invention exploiting electrical impedance data on wet concrete. Accordingly, based upon no information of the concrete type a first water content range may be specified based upon a simple electrical measurement and this water content range may be specified with improved accuracy based upon specification of the concrete type. Optionally, depending upon the sampling time, integration time, number of measurements, number of measurement frequencies etc. required for the measurement continuous or pseudo-continuous monitoring may be performed on the concrete at the construction site, at the pouring location, at the delivery location, and/or during transport.

Estimation of In-Situ Compressive Strength of Concrete after Pouring: Monitoring the compressive strength of concrete during the first few days from pouring up to 7 days after pouring is important for the optimization of formwork removal, especially in the winter time. Aside from the type of concrete mixture, the rate of strength development in concrete also significantly depends on other factors, such as the concrete temperature fluctuation which becomes important in different geographic regions at different times of the year, e.g. winter in north-eastern US, summer in south-west US, etc. The electrical resistivity of concrete can be used to estimate the compressive strength of concrete.

Figure 12:
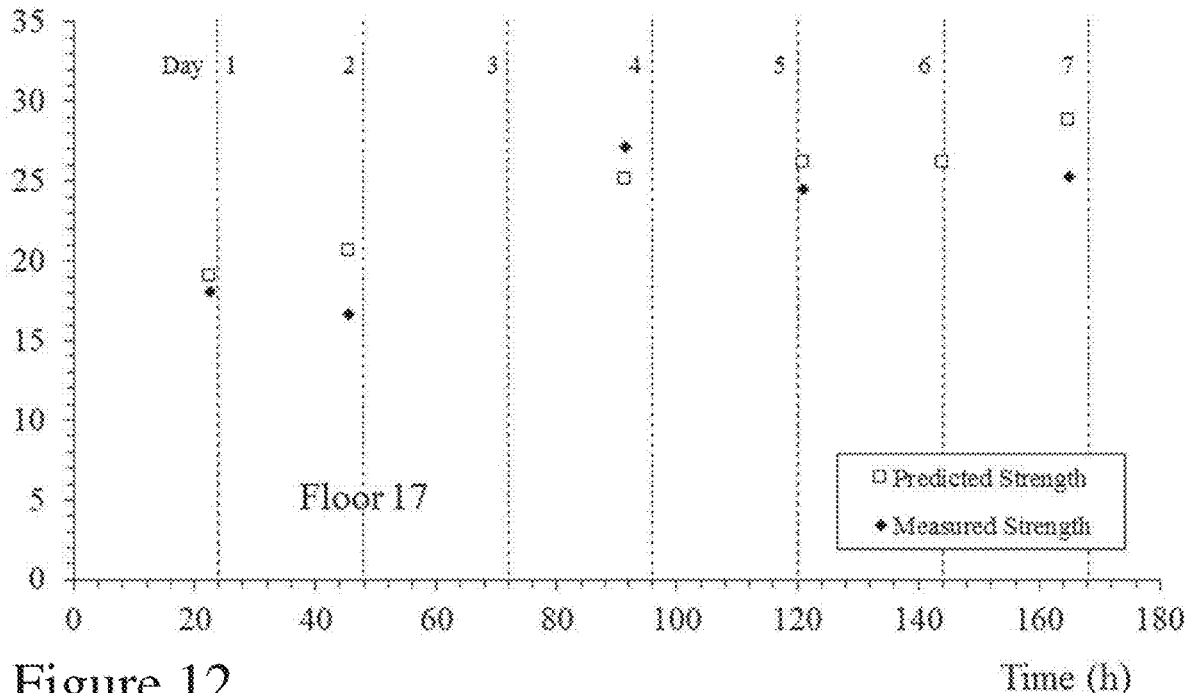
FIG. 12 depicts the estimation of real-time in-situ strength of concrete using electrical resistivity data according to an embodiment of the invention for floor 17 of a building.
Figure 13:
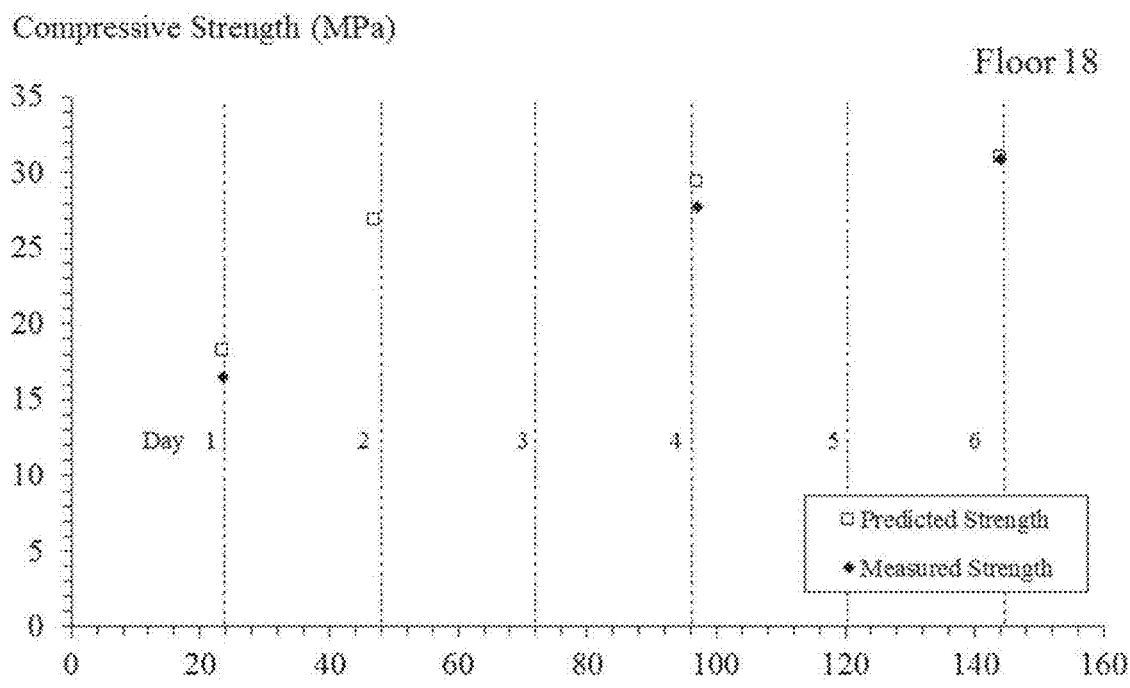
FIG. 13 depicts the estimation of real-time in-situ strength of concrete using electrical resistivity data according to an embodiment of the invention for floor 17 of a building.

Referring to FIGS. 12 and 13 there are depicted graphs for the 17th and 18th floors of a construction projected wherein the predicted compressive strength of concrete as derived by the inventors using electrical resistance measurements is plotted as a function of time. Accordingly, based upon a minimum target compressive strength of 25 MPa, for example, it is evident that this is reached from electrical measurement based analysis after 2 days allowing removal of framework at that time as only slight increase is noted from measurements over the following 5 days. Accordingly, electrical measurements allow for rapid, onsite measurements to be performed without requiring poured concrete to be sampled and characterised at a laboratory.

Figure 14:
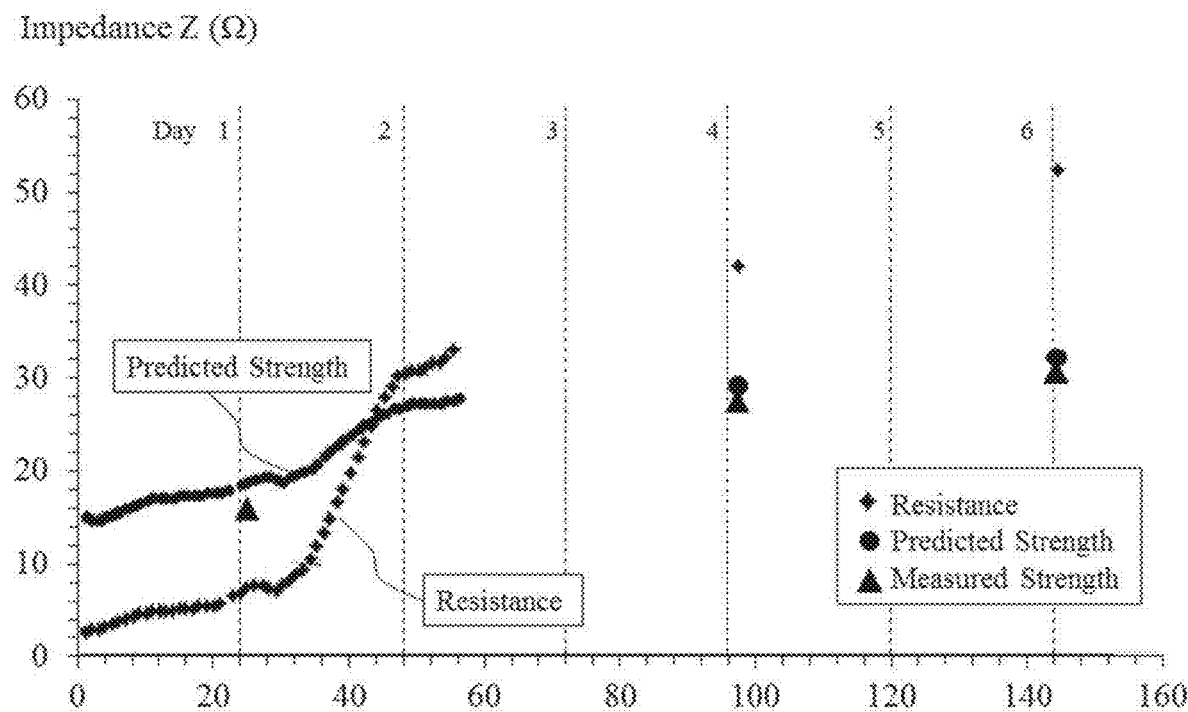
FIG. 14 depicts the extrapolation of concrete electrical resistivity for prediction of long-term compressive strength estimation according to an embodiment of the invention.

Prediction of 7-day, 28-day and 56-day Compressive Strength of Concrete (ASTM C39): The inventors have established that the electrical impedance of concrete measured at a certain frequency range can also be used to predict the long term strength of concrete such as those required at 7-day, 28-day and 56-day. The long-term compressive strength of concrete is an important design parameter that needs to be met during the construction but as with short-term compressive strength the complexity/cost/delay of physical sampling and laboratory testing can be removed through onsite testing with handheld meters providing electrical impedance measurements or temporarily installed electrical impedance data loggers that can be removed, relocated, reused etc. Referring to FIG. 14 there is depicted a plot of predicted and measured strength as a function of time together with electrical impedance measurements of the concrete.

Figure 15:
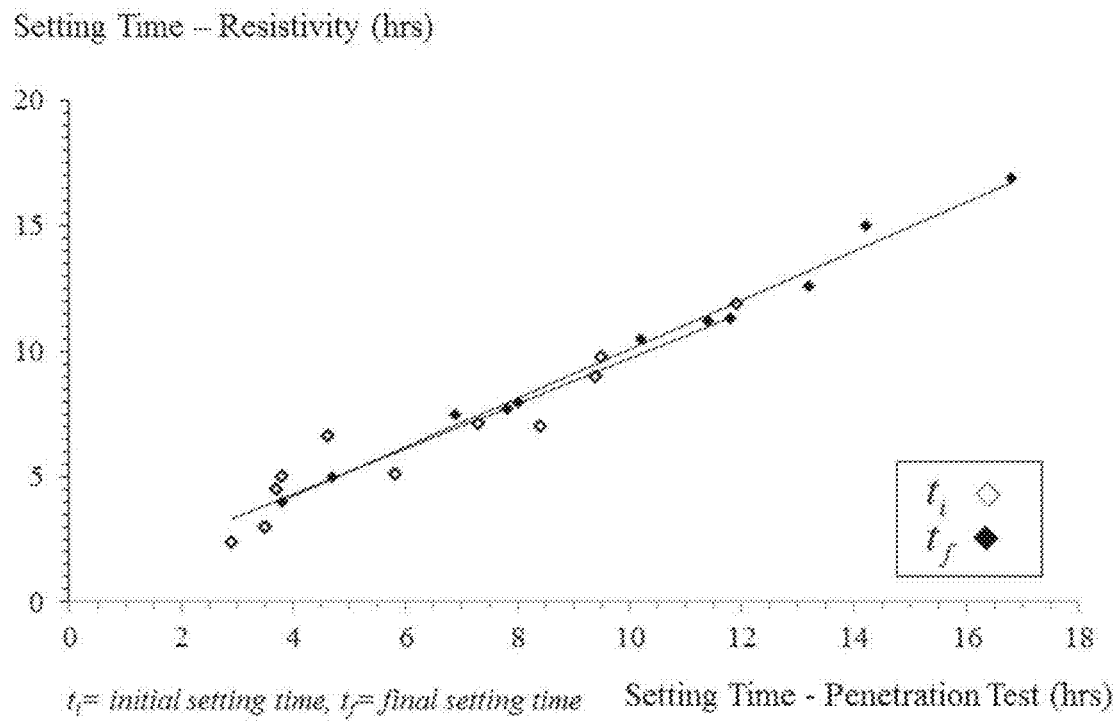
FIG. 15 depicts the comparison between setting times established by the ASTM 803 standard versus predictions from electrical resistivity measurements according to an embodiment of the invention.

Detection of Initial and Final Setting of Concrete (ASTM C403): The determination of initial and final setting of concrete is also important in deciding when to start the process of finishing the surface of concrete and also for sequential construction systems in which the concrete pouring is performed sequentially such as those in dams, silos and towers. As noted supra the prior art technique is based upon periodic physical testing of concrete samples taken from the pour. In contrast the inventors have established the determination of setting time through electrical impedance measurements as depicted in FIG. 15 where these are compared to the setting times of fresh concrete measured using the current standard, see ASTM C403 "Standard Test Method for Time of Setting of Concrete Mixtures by Penetration Resistance." Accordingly, electrical impedance measurements present a non-invasive, onsite test for setting time wherein data acquisition and determination can be automated and/or simplified allowing the removal for the requirement of trained personal, dedicated laboratory etc.

Figure 16A:
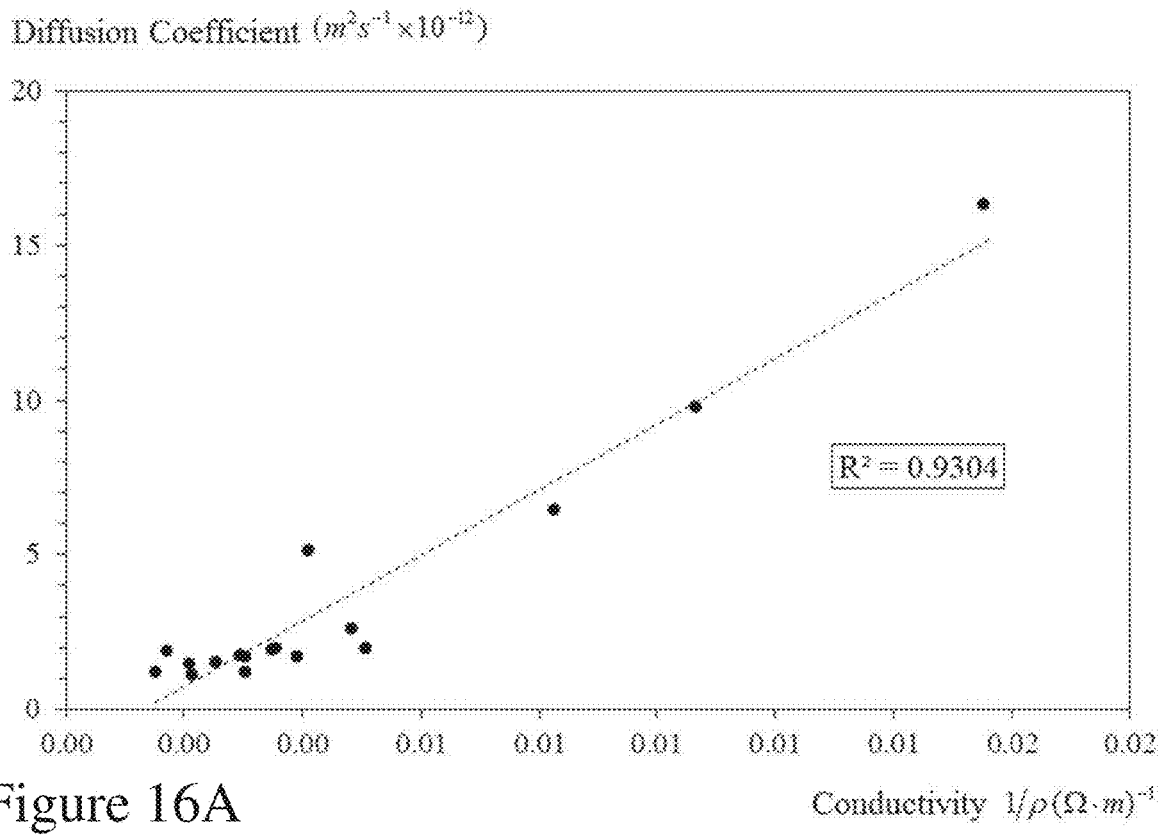
FIG. 16A depicts the relationship between electrical conductivity and chloride diffusion coefficient of concrete for twenty concrete samples as measured according to an embodiment of the invention.

Assessment of Transport Properties of Concrete such as Permeability, Diffusivity and Porosity: Historically, standards such as ASTM C1202 "Standard Test Method for Electrical Indication of Concrete's Ability to Resist Chloride Ion Penetration" and ASTM C1543 "Standard Test Method for Determining the Penetration of Chloride Ion into Concrete by Ponding." Acceptance criteria for this test according to such tests must consider multiple factors, including for example sample age and curing procedure, that affect the results and ensure balanced risk between supplier and purchaser. Accordingly, the inventors have established the electrical impedance of hardened concrete at long term measured at a certain frequency range and defined moisture level correlates with the transport properties of concrete such as diffusivity, permeability and porosity. As depicted in FIG. 16A the chloride diffusion constant is plotted as a function of the electrical conductivity determined from electrical impedance measurements is presented for twenty different proportions.

Figure 16B:
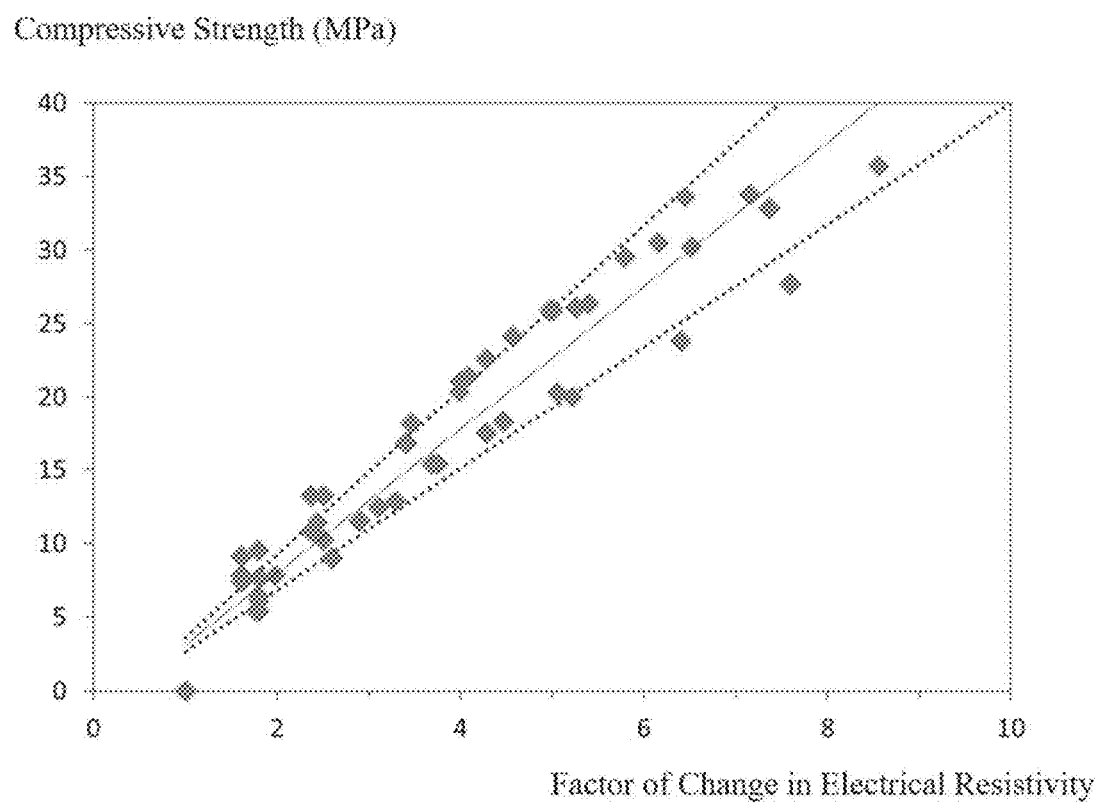
FIG. 16B depicts the relationship between electrical conductivity and compressive strength for concrete for concrete samples as measured according to an embodiment of the invention.

Assessment of Ultimate Compressive Strength of Concrete: Now referring to FIG. 16B there is depicted a graph showing the compressive strength of concrete samples plotted as a function of the electrical resistivity of the concrete samples as measured according to an embodiment of the invention. Accordingly, it is evident that the compressive strength shows a strong essentially linear correlation with electrical resistivity allowing such electrical measurements to be made and provide an indication of mechanical strength without requiring a concrete core sample be taken and measured in a laboratory at a later point in time. As such point of use measurements can provide earlier feedback and decision making for a construction activity involving a concrete pour.

Within other embodiments of the invention the electrical impedance measurements allows for ongoing structural factor determination such as crack detection and changes in pore solution. In the former case the electrical resistivity of concrete can provide an indication of the cracking initiation and the propagation in concrete structures as in general cracking decreases the solid connectivity and the cross section of the concrete element and thus increases the electrical resistivity. In the latter, the ingress of aggressive ions such as chlorides into the pore structure of concrete increases the conductivity of the pore solution and thus decreases the electrical impedance of concrete. Accordingly, electrical impedance can be employed to detect and monitor the penetration of such ions that can lead to the deterioration of concrete.

In addition to the benefits of knowing the water/cement ratio and strength development of concrete as described above other benefits can be derived including, for example, a feedback system to the concrete batching plant such that the amounts of the concrete ingredients can be optimized knowing the variations in the water/cement ratio and strength of the poured concrete and accordingly adjust for the effects of the transportation, delivery and pouring to ensure the poured concrete meets the minimum requirements established and to save on the cost of materials.

Beneficially, electrical impedance analysis in situ allows for curing/acceleration techniques such as the heating of formwork during the first few days after concrete pouring can be also optimized/adjusted to save energy and achieve the desired strength to allow framework removal earlier.

Within the experimental electrical impedance procedures described supra it is known that the electrical impedance of concrete changes with temperature variation such that higher temperature translates into lower electrical impedance. Accordingly, in order to compensate the effect of temperature on the results, a modification factor needs to be applied to offset the effect of temperature using Arrhenius equation as given by Equation (1) below.

$$F = e^{\left(\frac{E_a}{R}\right)\left(\frac{1}{T_0} - \frac{1}{T}\right)} \quad (1)$$

where F is the modification factor, $T_0$ is the reference temperature, $E_a$ is the activation energy, and R is the gas constant. Within the prior art values of this activation energy have been reported. In contrast, the inventors have established that for each application described supra in respect of exploiting electrical impedance measurements that there is a specific value of the activation energy coefficient.

Within the embodiments of the invention described supra the electrical measurement may be made using disposable and/or reusable wireless sensors deployed upon the infrastructure and pulled/pushed via a network and/or PED/FED to an application or applications for storage and analysis. For example, a disposable sensor may exploit Bluetooth connectivity for short range low power communications and ad-hoc network protocols so communicate electrical measurement data to a node or nodes wherein it is pushed to remote servers, what is commonly referred to today as "the cloud", through one or more different network interfaces and/or network protocols. Subsequently, this cloud stored data can be analysed in real time and/or periodically to determine one or more of the measurements described supra. At that point the derived performance data may be pushed to one or more entities including, for example, the concrete supplier, builder, owner of the structure, regulatory authorities etc. Alternatively, wired sensors or sensor nets may be deployed.

Figure 17A:
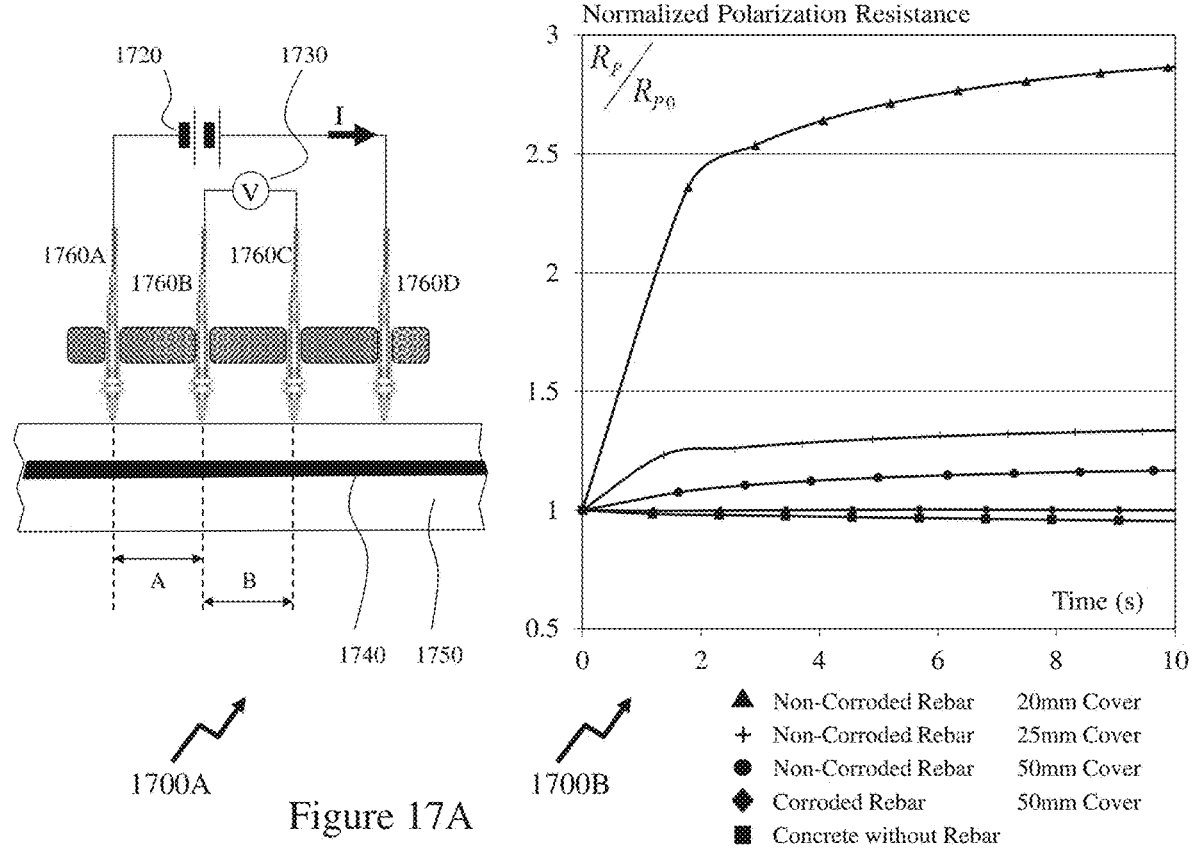
FIG. 17A depicts non-contact electrical characterization of corrosion and rebar presence within concrete according to an embodiment of the invention.

Hand-Held Non-Contact Corrosion and Rebar Detection Technology: Referring to FIG. 17A there are depicted first and second images 1700A and 1700B respectively with respect to a non-contact electrical characterization of corrosion and rebar presence within concrete according to an embodiment of the invention. Accordingly, as depicted in first image 1700A of FIG. 17A the electrical response of rebar inside the concrete is determined from the surface of the concrete with four probes without an electrical connection to the rebar within the concrete. Accordingly, there are depicted four probes 1760A to 1760D in an electrical configuration similar to that of a prior art 4-point Wenner probe in that the outer pair of probes 1760A and 1760D respectively apply a signal and the inner pair of probes 1760B and 1760C measure the resulting potential difference between them via voltmeter 1730. However, in contrast to the prior art wherein the signal applied across the outer pair of probes 1760A to 1760D is an AC signal, typically at 40 Hz, the inventors have replaced this with a DC current source 1720.

Within the prior art a 4-point Wenner probe, wherein all probes are equally spaced, or a 4-point Schlumberger probe, wherein the spacing of the outer probes from the inner probes is equal but different to the separation of the inner probes, is employed to measure the electrical resistivity of concrete. However, rebar(s) within the concrete can disturb the electrical resistivity measurements and accordingly the recommended measurement orientation of the 4-point Wenner/Schlumberger probes is determined by the spacing of the rebars as ideally the orientation is diagonal to the square matrix of rebars but if this not possible then the orientation should be perpendicular to the rebar. However, in the majority of structures these orientations and spacings are at best approximate and generally assumed relative to the portion of the concrete structure being measured.

However, using the DC current source 1720 according to embodiments of the invention the inventors have established the ability to determine the presence of a rebar and/or its corrosion state based upon the temporal evolution of polarization resistance determined from the measured signals as indicated in second image 1700B in FIG. 17A. Referring to second image 1700B it can be seen that for non-corroded rebar the evolution of the normalized polarization resistance is positive and the ratio after even only a couple of seconds is greater for rebars that are closer to the surface of the concrete. In contrast, the slope for a corroded rebar is close to zero for the same depth of rebar and also reduced in percentage deviation. A reference measurement of polarization resistance ratio in the absence of rebar within concrete is also depicted with a small negative slope.

The polarization resistance of rebar in concrete from the surface can be determined using Equation (2) wherein $R_p(t)$ is the polarization resistance of the rebar and concrete system, $V(t)$ is the potential measured at the two inner electrodes and $(t)$ is the current applied at the two outer electrodes. $R_{P0}$ is the polarization resistance of the system at time zero.

$$R_P(t) = \frac{V(t)}{I(t)} \quad (2)$$

As noted supra the relative polarization resistance of the reinforced concrete system, $R_P(t)/R_{P0}$, measured from the surface of concrete changes with time and depends upon the location and diameter of the rebar in the concrete as well as its corrosion condition, i.e. presence, severity and rate of corrosion. By decreasing the cover thickness of the concrete over the rebar then the increase in $R_P(t)/R_{P0}$ increases for non-corroding rebar. However, for a corroded rebar $R_P(t)/R_{P0}$ does not change significantly, and in fact is almost constant with no significant change.

This behavior is related to the polarization resistance of the passive film wherein the polarization resistance of rebar in concrete in the passive state (none-corroding condition) is much higher than that of the corroding rebar. As a result, for a corroding rebar, a portion of the current paths are through the rebar reinforcement as there is a little resistance on the surface of rebar against current flow. However, in the case of passive, non-corroded, rebar because of the high polarization resistance of the passive layer on the surface of the rebar the current passage through the rebar would be very limited, and therefore, increases over time as a result of polarization, i.e. charge of double layers of capacitors. Accordingly, the DC 4-probe measurement concept established by the inventors can be used to detect rebar corrosion from the surface of concrete without requiring any electrical connection to the rebar unlike other corrosion detection techniques in the prior art.

This method according to embodiments of the invention is also applicable to various types of rebar including, but not limited to, epoxy-coated rebar, stainless steel rebar, and galvanized steel rebar. Unlike other corrosion measurement techniques such as half-cell corrosion potential, linear polarization and galvanostatic pulse technique, this method is sensitive to the direction of rebars crossing each other. By changing the direction of the probe with respect to the reinforcement mesh then the measurement can detect the condition of only the rebar parallel to the direction of the measurement. Accordingly, the DC 4-probe technique can be used initially to verify that the thickness of concrete over the rebar within a new concrete structure meets the design requirements as the magnitude of $R_P(t)/R_{P0}$ for uncorroded rebar increases with decreasing rebar depth. At the same time, it can also verify that the condition of initial rebars is acceptable post concrete pour and subsequently be used to monitor the status of rebars within concrete structures directly and isolate the condition of the rebars in each direction discretely.

Figure 17B:
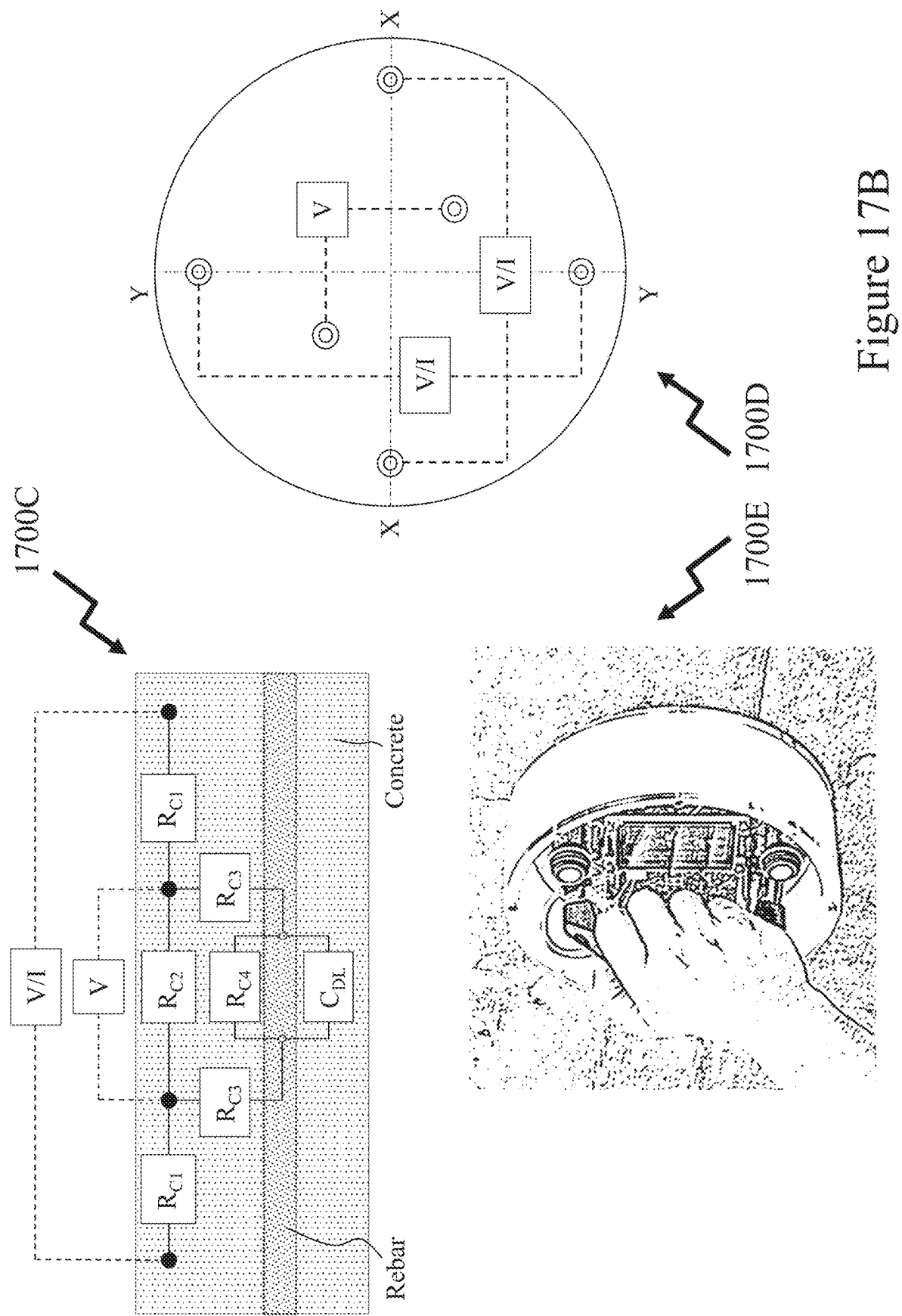
FIG. 17B depicts equivalent electrical circuit and hand-held test instrument for extracting characteristics of a reinforced concrete system.

It would also be evident to one skilled in the art that such a DC 4-probe measurement technique may form part of an embedded sensor for corrosion monitoring as well as for periodic manual based monitoring. Referring to FIG. 17B there is depicted in first to third images 1700C to 1700D respectively a handheld non-contact corrosion detector instrument according to an embodiment of the invention. As depicted in first image 1700C different electrical characteristics of the reinforced concrete system can be extracted using a 6-point probe established by the inventors. As depicted in second image 1700D a pair of measurement contacts allow measurement of a voltage, V, to the concrete surface wherein the measurements are made by a first pair of excitation contacts aligned at 45° to the inner contacts and a second pair of excitation contacts aligned at −45° to the inner contacts such that the first and second pairs of excitation contacts are orthogonal to each other and offset at 45° relative to the inner contacts. A prototype instrument of such configuration is depicted in third image 1700E.

Then as evident from the equivalent electrical circuit in first image 1700C the following can be determined:

Polarization resistance of rebar (charge transfer resistance) ($R_P$): This parameter is related to the corrosion rate of rebar in concrete allowing the corrosion rate to be calculated from $R_P$ using $i_{COR}=B/(A \cdot R_P)$.

Double layer capacitance ($C_{DL}$): The extent or severity of corrosion can be calculated from this parameter.

Electrical resistance of concrete ($R_{C1}$, $R_{C2}$): The intrinsic electrical resistivity of concrete can be calculated from these two parameters. The effect of the rebar would be excluded in the measurement using this approach according to embodiments of the invention which cannot be done with prior art AC measurement techniques.

Electrical resistance of concrete cover ($R_{C3}$): The relative value of this parameter with respect to $R_{C1}$ and $R_{C2}$ may be used to estimate the cover thickness of concrete.

Accordingly, using the novel configuration depicted in second image 1700D the inventors have established an instrument that allows the corrosion measurements on rebars along the X and Y directions to be performed separately. Also, in this design, we use only two inner probes for the voltage measurement in both directions. Using this arrangement, only the direction of applied current or voltage on the external electrodes will be switched between the X and Y directions. In the other words, the same inner probes are used for the voltage measurement for both directions modified based on the 4-probe method.

In-Situ Concrete Testing: As discussed and described supra in respect of embodiments of the invention electrical measurements in-situ on concrete can provide information relating to cured concrete performance when made upon "wet" concrete and lifetime performance when made periodically subsequently. Accordingly, it would be beneficial to provide construction companies, builders, etc. with a test configuration that allowed for both of these to be performed without significant additional effort, expenditure or disruption. Now referring to FIG. 18 there is depicted a concrete assessment assembly (CONCAA) 1800A there is depicted an embodiment of such a test configuration. As depicted the CONCAA 1800A comprises a tube 1840 having internal diameter of 150 mm (6"), for example, and depth of 300 mm (12"). This tube 1840 is disposed within a structure prior to pouring with rods 1830 mounted within holder 1820 that fits onto the upper surface of the tube 1840. As such during the pour the concrete wells up within the tube 1840 surrounding the rods 1830.

Figure 18:
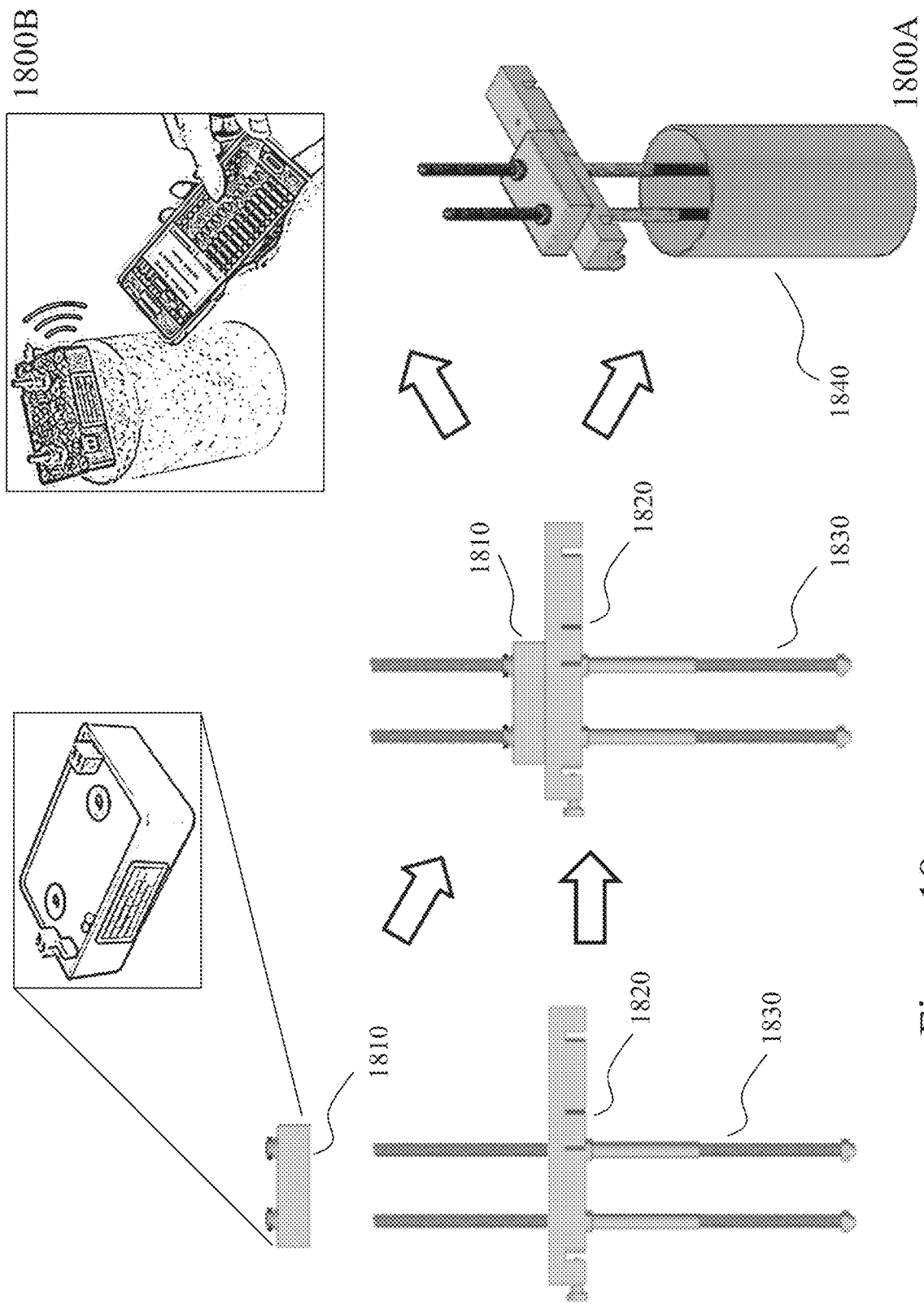
FIG. 18 depicts modular test assembly according to an embodiment of the invention for measuring concrete during its initial curing and subsequent lifetime of the concrete structure.

During the initial post-pour stage, a tester 1810 is fitted to the upper exposed portions of the rods 1830 and retained in position with nuts on the threaded rods 1830. The tester 1810 then monitors the electrical parameters of the circuit formed between itself, the pair of rods 1830 and the concrete which is now curing. Subsequently, the recorded data from the tester 1810 can be retrieved, for example, wirelessly via a PED such as depicted in image 1800B. At some predetermined point later, the tester 1810 can be removed and a protective cap applied to the CONCAA 1800A. This may be determined from a protocol established in dependence upon the electrical characteristic evolution such as described and depicted supra in respect of FIGS. 4 to 9B respectively. The testers 1810 can then be applied to a subsequent pour and/or be re-positioned periodically to perform ongoing concrete assessment. In the latter scenario the test engineer visits the site, for example, places the testers 1810 onto the CONCAA 1800A for a predetermined period of time before the measurements are retrieved from the testers 1810 and employed to define the properties of the concrete. This as depicted in FIG. 18 be via a wireless interrogation of the tester 1810 but it may alternatively be via a wired connection such that the reader, e.g. a smartphone or tablet, is connected to the CONCAA 1800A via a cable and connector or optical communications link.

Smart Rocks and Smart Concrete

It would be evident to one skilled in the art that the techniques, methodologies, etc. described supra in respect of FIGS. 11 to 16B, 17A, 17B, and 18 are directed to lifetime characterization of concrete either from the viewpoint of the characterization of fresh concrete properties through to lifetime monitoring. Even assemblies such as CONCAA 1800A require that the construction team are provided with a detailed plan denoting where and when they are to be employed within the construction project. However, even these measurements whilst advancing the data and information available to the construction team, architect, quality management, surveyor, regulatory authority etc. have limitations with respect to the number that can be used, their locations, etc. and the fact that the measurements taken may require detailed data such as a maturity calibration curve from the concrete producer. Further, an essential portion of the "chain" is still not captured and accordingly pre-acceptance testing of the concrete may still be necessary prior to its being poured at the site.

Figure 20:
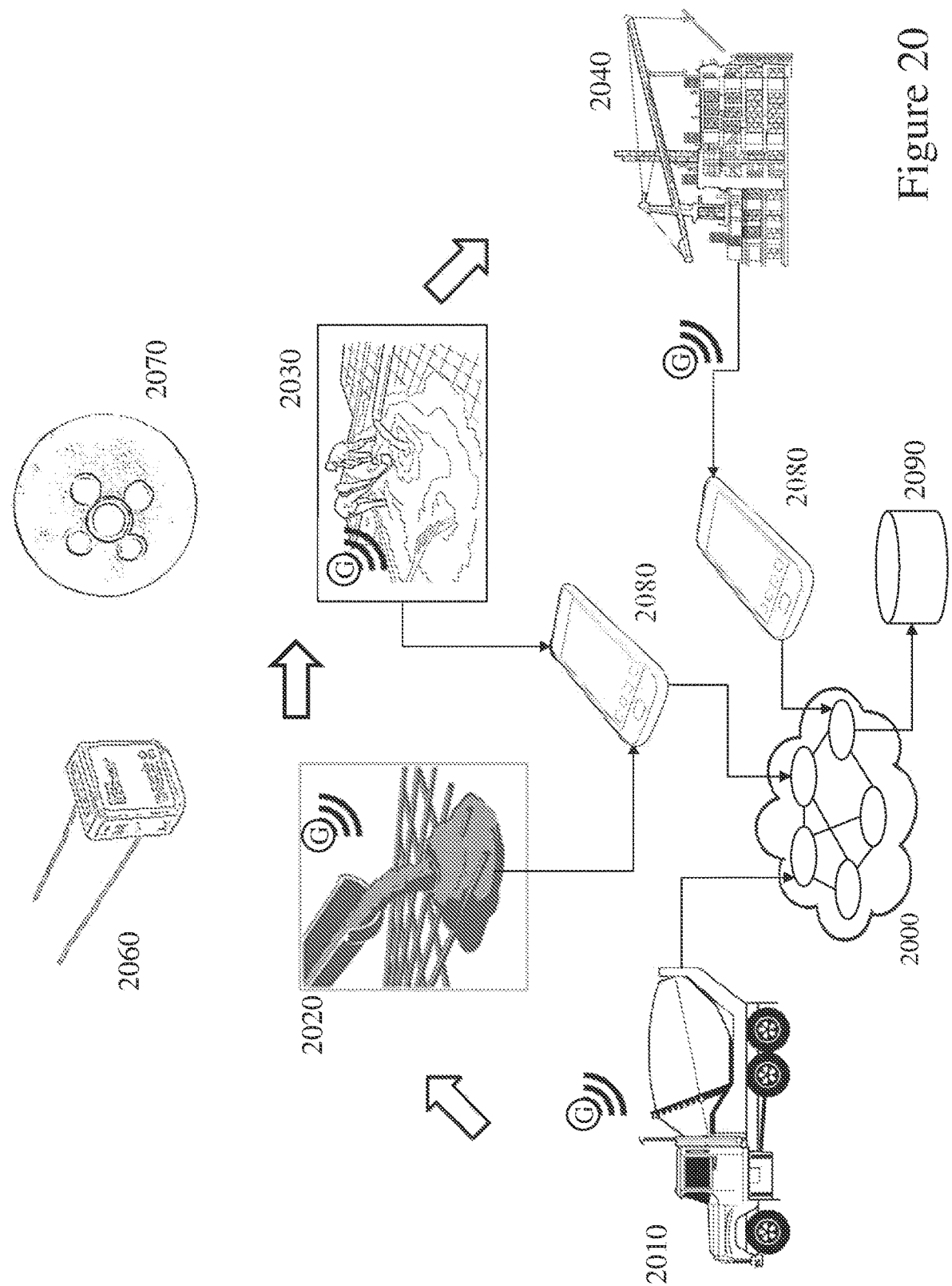
FIG. 20 depicts an embedded sensor methodology for data logging concrete properties from initial mix through pouring, curing, and subsequently according to an embodiment of the invention.

In order to address the issues identified within the background supra the inventors have established a methodology exploiting "embedded sensors" or what the inventors refer to as "SMArt rocKs" (SMAKs, namely sensors) and "Smart Concrete" which refers to concrete with one or more SMAK (s) within or in contact with the concrete. As such these embedded sensors, such as depicted in prototype 2060 and production concept form 2070 in FIG. 20, are added to the concrete batch loaded onto the concrete truck at the batching plant. It is therefore possible to "tag", i.e. load into, the embedded sensor information relevant to the mix as well as delivery data etc. This information as well as other measurements made by the embedded sensors during the transportation, pouring, and placement can be accessed by wireless interface by the end user once the concrete is delivered to the construction site, as it is poured, and during its curing, maturation processes.

Figure 19:
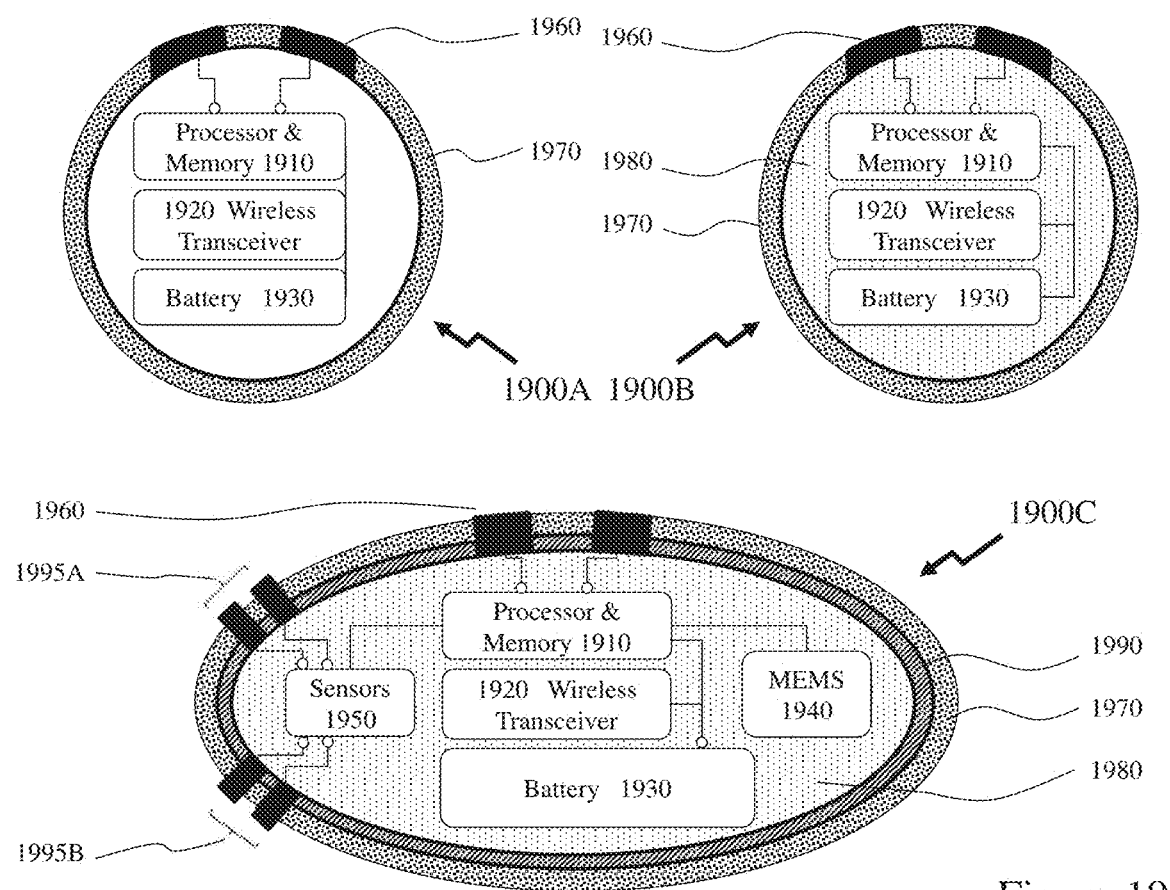
FIG. 19 depicts examples of embedded sensors for data logging concrete properties from initial mix through pouring, curing, and subsequently according to an embodiment of the invention.

Referring to FIG. 19 there are depicted first to third SMAKs 1900A to 1900C according to embodiments of the invention. Referring to first SMAK 1900A contacts 1960 are formed within outer shell 1970 defining an interior within which are disposed a processor with associated memory 1910 (hereinafter, processor). The processor 1910 being coupled to a wireless transceiver 1920 and a battery 1930. Accordingly, electrical conductivity (for example) between the contacts 1960 may be monitored (e.g. arising from water within a concrete mix), processed with the processor 1910, stored and then subsequently transmitted via wireless transceiver 1920 when a link is established to a portable electronic device (PED) such as smartphone, tablet PC, or dedicated device. The shell 1970 may be formed from a variety of materials, including but not limited to, metals (from which the contacts are isolated by insulating rings etc.), ceramics (e.g. alumina, zirconia, etc.), composites (e.g. fiber reinforced polymer, ceramic matrix composites, concrete, glass-reinforced plastic) and plastics (e.g. short-fiber thermoplastics, long-fiber thermoplastics, thermosetting plastics, filled plastics, synthetic rubber, elastomer, etc.).

Second SMAK 1900B depicts essentially the same construction as SMAK 1900A except that the interior of the shell is now filled with a filler 1980. Second filler material 1980 may be a resilient filler 1980 surrounded by a soft shell 1970 such as synthetic rubber or elastomer, for example, or alternatively the filler 1980 may be semi-resilient in combination with a resilient shell 1970. Such semi-resilient fillers 1980 may include thermosetting resins, catalyzed resins, cured silicone gels, etc. used in conjunction with a shell 1970 formed from a plastic or rubber, for example.

Third SMAK 1900C exploits the same filler 1980 with shell 1970 but now an intermediate casing 1990 is disposed between the outer shell 1970 and the inner filler 1980. For example, casing 1990 may be an impermeable membrane, e.g. Gore-Tex™, that limits moisture ingress to the SMAK 1900C but allows air or gas permeability. Further, SMAK 1900C now comprises in addition to the processor 1910, wireless transceiver 1920, and battery 1930 additional sensors 1960 which are coupled to first and second SENsor INTerfaces (SENINTs) 1990A and 1990B which together with contacts 1960 provide external sensing data to the processor 1910. Further a microelectromechanical system (MEMS) 1940 within the SMAK 1900C provides data to the processor 1910 wherein the MEMS 1940 may comprise, for example, an accelerometer such as a one-dimensional (1D), two-dimensional (2D) or three-dimensional (3D) accelerometer providing data relating to motion, shock, etc. Within different embodiments of the invention some SENSINTs may have direct exposure to the external environment whereas others may be indirect or via a barrier material etc. or have a characteristic that varies in response to an external environmental aspect. Sensors may include, but are not limited to, temperature, electrical resistance, pressure, light, acceleration (e.g. MEMS accelerometer), vibration (e.g. MEMS sensor), humidity (e.g. capacitive sensor barriered with a vapour barrier to prevent direct fluid contact), pH (e.g. ion sensitive field effect transistor—ISFET pH sensor), ion content (to detect externally penetrating chemicals or materials), chloride content, microphone or acoustic sensor (to detect crack propagation), gas sensor (e.g. nitrogen, oxygen to detect air within cracks propagating to the surface of the concrete), corrosion detectors, visible optical sensors, ultraviolet optical sensors, and infrared optical sensors. More advanced sensors may provide dedicated hardware, functionality, and software to enable more advanced techniques such as nuclear magnetic resonance, electrochemical, X-ray diffraction, optical spectrometry, thermogravimetric analysis, a half cell, etc. as well as corrosion resistance etc.

As such SMAKs, such as first to third SMAKs 1900A to 1900C, depicted in prototype 2060 and production concept form 2070 in FIG. 20, may be added to a concrete batch loaded onto a concrete truck at the batching plant, within an embodiment of the invention. It is therefore possible to "tag", i.e. load into, the SMAK information relevant to the mix as well as delivery data etc. This information as well as other measurements made by the SMAKs during the transportation, pouring, and placement can be accessed by wireless interface by the end user once the concrete is delivered to the construction site, as it is poured, and during its curing, maturation processes.

As such the tagging of the SMAKs may include, but not be limited to, information such as batch identity, truck identity, date, time, location, batch mix parameters, etc. but also importantly information such as the maturity calibration curves for the mix established by the manufacturer. Accordingly, depending upon the degree of complexity embedded into the SMAK such data may be either retrieved for remote storage and subsequent use or it may be part of the SMAKs processing of electrical measurement data such that calibration data of the concrete mix is already factored into the data provided by the SMAKs. Accordingly, the SMAKs, such as prototype 2060 and production concept form 2070 may be added to the concrete at the batching point 2010 either tagged already or tagged during loading. Subsequently upon delivery and pouring 2020 the SMAKs may be read for information regarding the delivery process etc.

Once poured the SMAKs may be read for curing information 2030 and then subsequently, depending upon the battery—power consumption etc., periodically read for lifetime data 2040 of the concrete. In each instance the acquired data may be acquired wirelessly and stored on a user's PED or it may then be pushed to a network 2000 and therein to one or more servers 2090. For devices wireless interrogating the SMAKs these may be executing a software application which presents to the user concrete parameter data either as provided from the SMAK(s) directly using the calibration curves stored within or upon the device using calibration curve data stored within the SMAK but not processed by it, stored within the device or retrieved from the data stored upon the remote server 2090. As depicted the SMAKs may be interrogated with a PED 2080 or alternatively the data stored upon the remote server 2090 may be interrogated and accessed by a PED 2080.

As depicted prototype sensor 2060 is enabled when an electrical circuit is completed via the flying leads. In production concept form 2070 the sensor may be enabled through a wireless signal, a vibration exceeding a threshold, via an electrical circuit being completed, increase in humidity beyond a threshold, decrease in light, etc. Accordingly, the embodiments of the invention support tagging the sensors and embedding the maturity calibration curves in the sensor. These curves are mix-specific and depending on the temperature history of the concrete can be used to estimate the strength of concrete. By embedded them within the sensors and the sensors employing this data the concrete manufacturer does not need to release commercially sensitive information such as their proprietary mix and calibration curves.

Based upon the combination of SMAKs within the concrete mix and their wireless interrogation and mobile/cloud based software applications other technical enhancements may be implemented, including for example:

Weather forecast API, such that the ambient temperature prediction in conjunction with current concrete data can be used to predict/project the strength identifying quality problems earlier;

Automatic detection of concrete pouring time, e.g. from electrical connection once the concrete is poured or change in the pressure, humidity, light etc.;

Tagging the sensor using NFC with smartphone;

Data integrity and management on remote servers;

Data analytics and/or artificial intelligence on data analysis as the SMAK manufacturer may acquire data from a large number of job sites allowing additional analytics, reporting, alarms etc.;

A SMAK manufacturer may establish so-called "big data" on concrete properties and concrete curing cycles/processes across a large number of job sites, geographic regions, time frames etc. allowing them to provide feedback from their server based processes to the end user;

Push notifications, such as for example the formwork company is notified when is the time to remove the formwork based upon actual concrete curing data; and Heat optimization wherein for example closed loop feedback of the temperature history and strength development can be employed to optimize heating employed in cold climates to ensure the concrete slabs gain sufficient strength within a specific period.

Considering heat optimization then this may also be used in establishing closed-loop feedback to optimize cooling of "mass concrete". "Mass concrete" is defined by the American Concrete Institute as "any volume of concrete with dimensions large enough to require that measures be taken to cope with the generation of heat from hydration of cement and attendant volume change to minimize cracking." Accordingly, cooling water is typically passed through pipes embedded in the mass concrete in order to keep the temperature gradient between the surface and the core of concrete below a threshold. Accordingly, SMAK sensors distributed within the mass concrete would allow for this process to be controlled, adjusted, measured, verified and optimized.

In addition to measuring, for example, temperature, DC electrical conductivity, and AC electrical conductivity it would be evident that additional parameters as discussed and described supra in respect of embodiments of the invention may be measured and monitored, including, but not limited to, concrete moisture content, concrete internal relative humidity, concrete pH, concrete mixture consistency, concrete workability (slump), concrete air content, hydraulic pressure, segregation, cracking, penetration of external ions into concrete, dispersion of fibers, and dispersion of chemical additives and supplementary cementitious materials.

Figure 21:
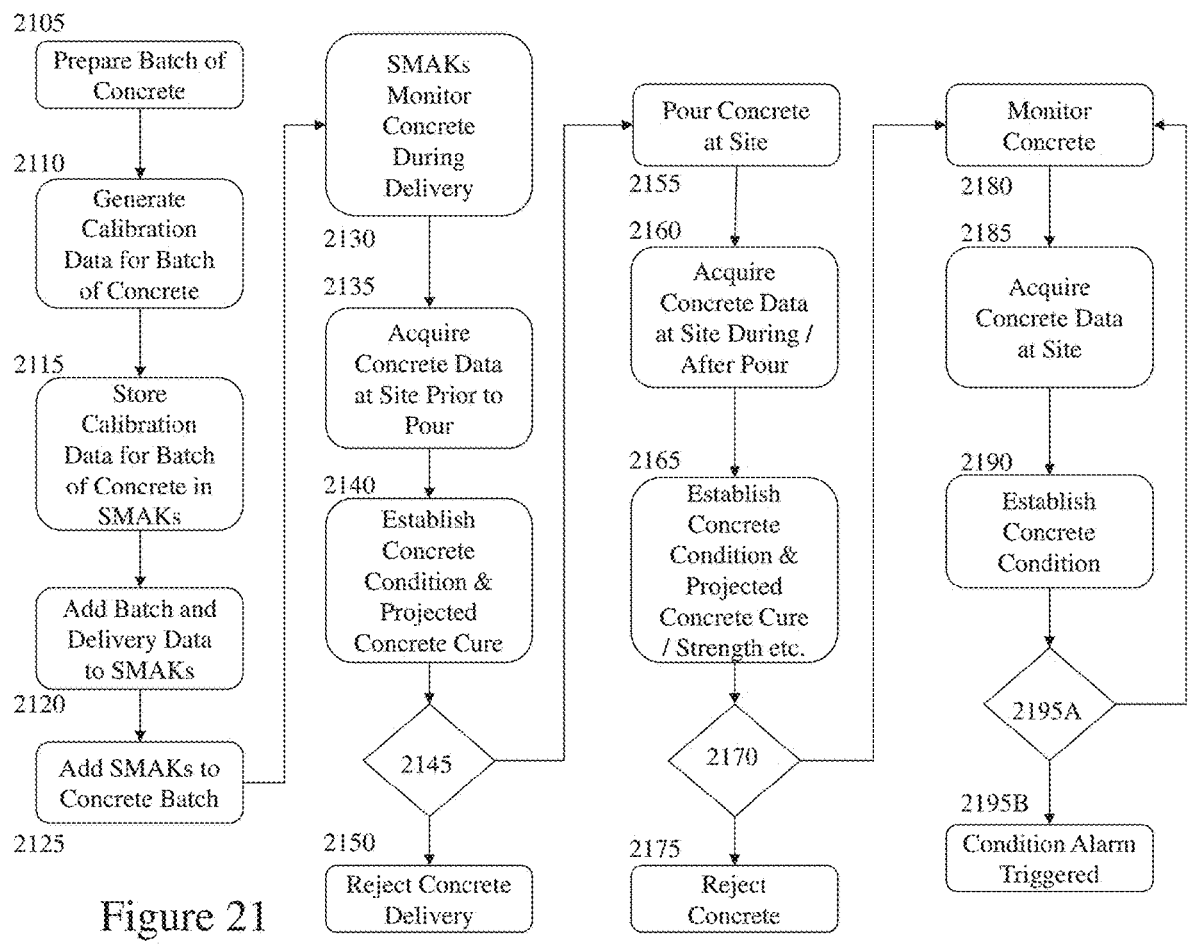
FIG. 21 depicts an exemplary process flow for an embedded sensor methodology for data logging concrete properties from initial mix through pouring, curing, and subsequently according to an embodiment of the invention.

Now referring to FIG. 21 there is depicted an exemplary flow for SMAK methodology for data logging concrete properties from initial mix through pouring, curing, and subsequently according to an embodiment of the invention. Accordingly, the process begins with step 2105 wherein a batch of concrete is prepared wherein in step 2110 the calibration data, for example the maturity calibration curves, is generated for that batch. Next in step 2115 this calibration data is stored within a batch of sensors which will be embedded with the concrete mix. Subsequently, in step 2120 additional data such as date, time, location, delivery identity, order data, manufacturer identity, etc. Once the sensors have been embedded with the data then they are mixed/embedded into the concrete for delivery.

Accordingly, the now SMAKs monitor the concrete during the delivery—transportation sequence in step 2130 wherein at the site the current data is retrieved from the SMAKs in step 2135 wherein this is employed to establish current concrete condition and projected cure in step 2140 wherein a delivery accept/reject decision is made in step 2145 wherein a rejection leads to step 2150 otherwise the process proceeds to step 2155 wherein the concrete is poured on site and the SMAKs continue monitoring. Next in step 2160 the data from the sensors is retrieved either in a single retrieval event or multiple events such that in step 2165 the concrete condition, projected cure, projected strength, etc. are established. Next in step 2170 a decision on the concrete pour is made as to whether it will be allowed to continue curing or whether there is a problem and remedial work/tear-down etc. are required at which the process proceeds to step 2175 and terminates or proceeds to step 2180.

In step 2180 the SMAKs continue monitoring the concrete but now for longer term characteristics as the cure has been passed at step 2170. Subsequently the SMAK data is acquired in step 2185 and used in step 2190 to establish the concrete's condition. If everything is within defined boundaries, then the process proceeds from a decision step 2195A to loop otherwise it proceeds to step 2195B and an alarm is triggered with respect to the condition of the concrete. In this manner the life cycle of the concrete can be tracked with the SMAKs.

Optionally, rather than pouring the SMAKs with the concrete or pre-installing them on the rebar or within the formwork they may be installed post-pour by pushing them into the concrete once it has been poured. Within other embodiments of the invention the SMAKs may be deployed through a hose and pneumatically projected at high velocity onto a surface, so-called shotcrete.

Optionally, to provide extended lifetime of the SMAKs their initial sampling rate during activation, transport, pour and curing may be amended to an increased period between sampling points wherein, for example, after a first predetermined period (e.g. 1 week) the sampling drops to a lower rate, then again at predetermined points either time based or concrete cure derived such that, for example, sampling drops to hourly, daily etc. to provide extended battery life. Alternatively, the SMAKs may be designed for specific short life cycle for the initial portion of the concrete life cycle after which the SMAK may be read periodically, where near the surface of the structure, such as through wireless power activation as employed in Radio Frequency IDentification devices (RFID) or another wireless power transfer methodology such as HIghly RESonant WIreless POwer (HIRES-WIPO) transfer, for example, that may increase the depth at which SMAKs may be wirelessly activated.

Accordingly, data regarding the curing of a concrete structure throughout its structure may be derived rather than from a limited number of sampling points or concrete tests on delivered concrete. For example, the number of SMAKs may be established as 1 per cubic meter, 1 per 2 cubic meters, 1 per 8 cubic meters, 4 per truck irrespective of load, etc. The number may be varied in accordance with concrete mix, architect schedule so that sensitive load bearing structures are more accurately plotted than others.

Figure 22:
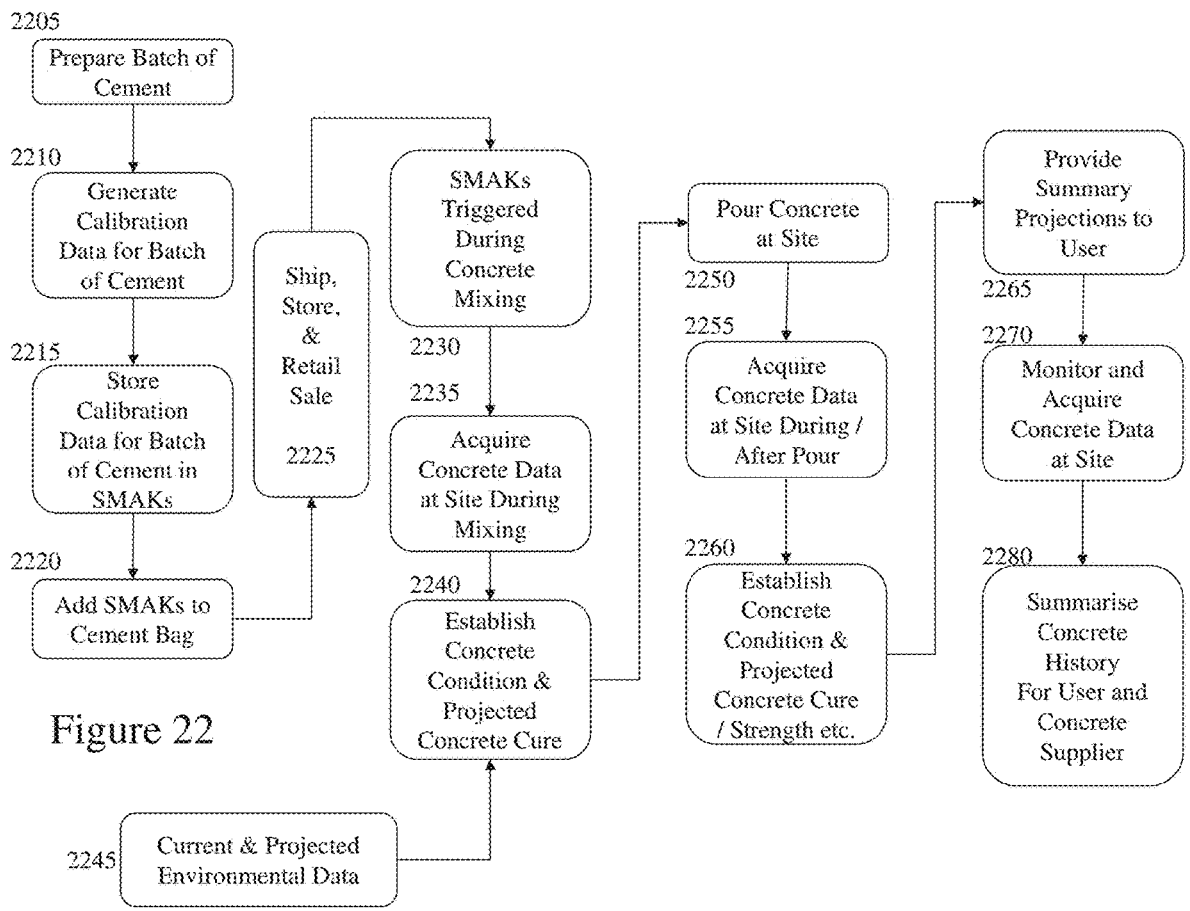
FIG. 22 depicts an exemplary process flow for an embedded sensor methodology for data logging concrete properties for concrete mixed at a worksite from "bagged" cement from initial mix through pouring, curing, and subsequently according to an embodiment of the invention.

Now referring to FIG. 22 there is depicted an exemplary flow for SMAK methodology for data logging concrete properties from initial mix through pouring, curing, and subsequently according to an embodiment of the invention wherein the SMAK is deployed in conjunction with a bag of cement (e.g. Portland cement) which is subsequently used to make a batch of concrete. Whilst the following description relates to a bag of cement it would be evident that the methodology described may be similarly employed with a pre-packaged concrete mix comprising cement, sand, and ballast to which only water is required to be added. Alternatively, it may be a mix of dry ingredients such as aggregate, an admixture, a supplementary cementitious material. Optionally, the SMAK may be part of a fiber bag filled with pre-package concrete mix designed to be laid down and absorb water through natural processes such as rain water, flood water etc. or by being watered from a spout, hose, water tanker etc. Optionally, the SMAKs may be sold discretely from the mix for the user to add when mixing the concrete, for example, within a small mixer or on the ground rather than a large commercial mixing truck.

Accordingly, the process begins with step 2205 wherein a batch of cement is prepared wherein in step 2210 the calibration data, for example the maturity calibration curves, is generated for that batch. Next in step 2215 this calibration data is stored within a batch of sensors which will be embedded with the cement. Optionally, in an addition step which is not depicted, additional data such as date, time, location, order data, manufacturer identity, etc. may be added to the SMAKs. Once the sensors have been embedded with the data then they are mixed/embedded into the concrete for delivery. Subsequently, in step 2220 the SMAK or SMAKs are added to the cement bag. This may for example, be via placement of the SMAK(s) within a container (e.g. plastic pouch), attached to the cement bag, typically internally, such that they can be subsequently retrieved and deployed. For example, a bag of cement may include 1, 2, 3, or more SMAKs with instructions that a particular number of SMAKs are added to a concrete mix made with, for example, quarter of a bag of cement, half a bag of cement or a full bag of cement, for example. At this point the bag of cement or concrete mix is stored, shipped to a retail store, stored and subsequently purchased and used.

Accordingly, the SMAKs may monitor the cement storage, shipment, storage and deployment process based upon data logging performed continuously or temporarily upon detection of an event such as movement of the bag. Alternatively, the SMAKs may be passive until activated at mixing such as closure of an electrical contact through the water employed within the mixing process, for example. Accordingly, the triggered active SMAKs in step 2230 acquire data during the concrete mixing in step 2235 which is processed to establish concrete condition and projected concrete cure based upon the SMAK data in step 2240 which is either processed by the SMAK and communicated to a PED executing an application to accept data from the SMAKs or data is transferred to the PED and then used by an application in execution upon the PED. Wherein processing of the data is performed on a PED at the worksite then the application may extract current and projected environmental data 2245 from a service, e.g. a web based weather network.

Subsequently, in step 2250 the concrete is poured at the worksite and the SMAKs continue monitoring in step 2255. Next the data from the sensors is retrieved either in a single retrieval event or multiple events such that in step 2260 the concrete condition, projected cure, projected strength, etc. are established. Next in step 2265 summary projections are provided to the PED or another PED wherein a decision on the concrete may be made as to whether it will be allowed to continue curing or whether there is a problem and remedial work/tear-down etc. are required at which the process proceeds to step 2270 wherein the SMAK(s) continue to acquire data for a long as their internal battery allows or subsequently where remote powering through RFID and/or HIRES-WIPO provides power to perform a data acquisition and wireless transmission.

Figure 23:
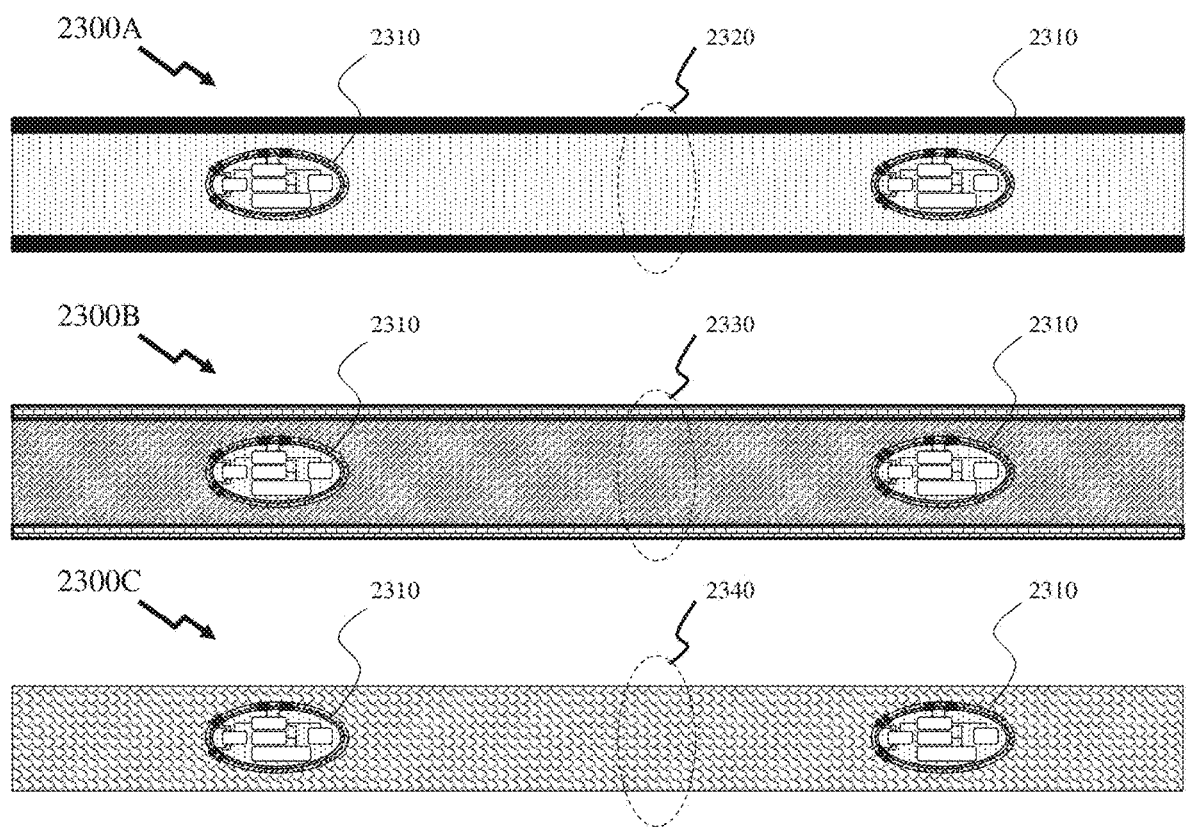
FIG. 23 depicts examples of embodied sensors employed within other manufacturing materials for logging manufacturing and/or se parameters according to embodiments of the invention.

Whilst the SMAKs have been described with respect to their use within concrete it would be apparent that variants may be employed within other materials in order to monitor, log, track, and verify aspects of their transport, delivery, and use. For example, SMAKs 2310 may be employed as depicted in FIG. 23 within gypsum board 2320 in first image 2300A, particle board 2330 in second image 2300B, and a fiber board 2340 (e.g. medium density fiberboard—MDF) in third image 2300C. Within gypsum board 2320 the SMAKs may be mixed within the gypsum slurry as it is applied or placed within the gypsum slurry just as the upper sheet is applied, for example. Similarly, within particle board 2330 and fiber board 2340 the SMAKs 2310 may be mixed with the wood particles/fibers respectively as rolled out. Accordingly, SMAKs can provide data relating to the storage and deployment of the material they are embedded within. In such instances the parameters measured may vary with the product being manufactured. Similarly, the data stored within the SMAKs during the manufacturing of the product may be varied.

SMAKs according to embodiments of the invention may be formed from a variety of materials include, but not limited, to metals, ceramics, plastics, resins, and rubbers according to the requirements for compatibility with the concrete, lifetime, crush resistance etc. Optionally, the SMAKs may be hollow or solid with cavities for electronics/battery etc. Optionally, the SMAK may comprise a plurality of metallic elements isolated with respect to each other to form electrical connections between the electronics within the SMAK and the concrete.

It would be evident that the use of products with embedded SMAKs such as bag cement, for example, may be regulated for instances where the bag cement is employed in a structural element of a construction activity, e.g. making steps, floors, supporting beams, etc. but be optional or unnecessary in other applications, e.g. making a path. Optionally, the data acquired from one or more SMAKs with a PED executing an application communicating to and/or retrieving data from the SMAKs may push the data to one or more cloud storage locations for subsequent retrieval by one or more parties including, but not limited to, product manufacturer, retailer, contractor, and regulatory authority.

Figure 25:
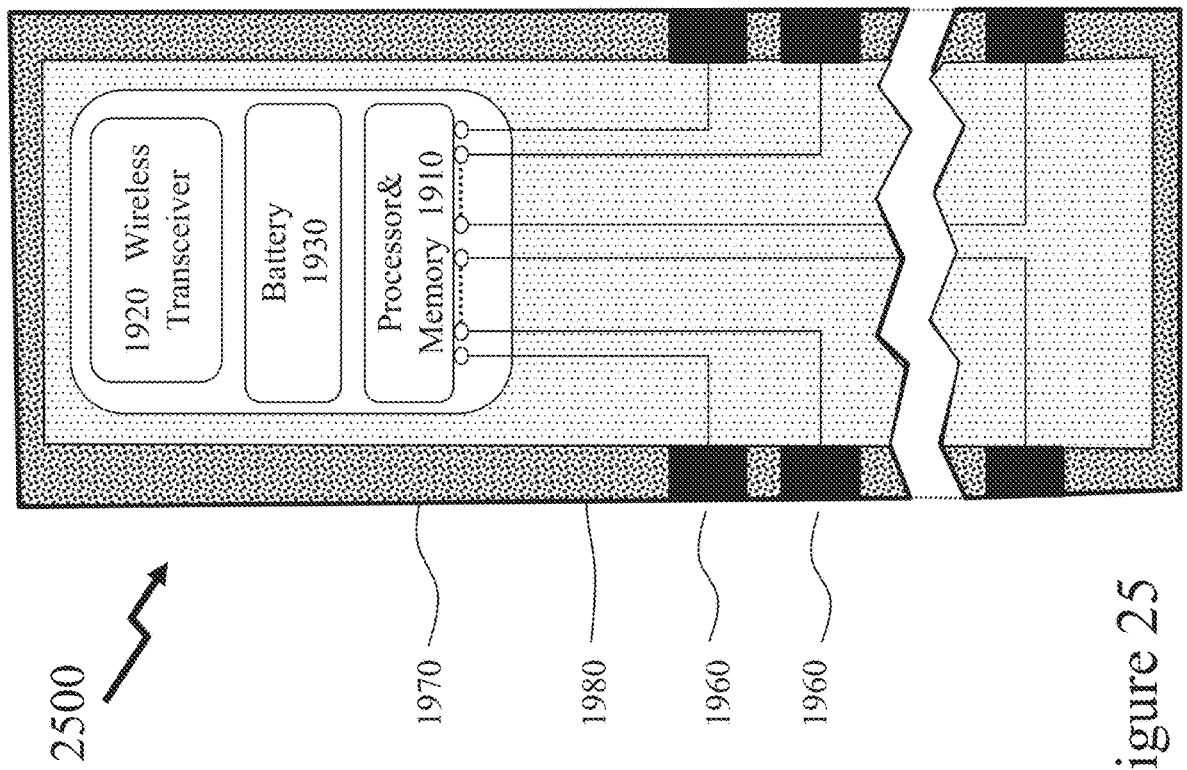
FIG. 25 depicts an embedded sensor according to an embodiment of the invention with multiple sensors distributed along the length of the sensor allowing for the measurement of gradients during concrete curing, for example.
Figure 24:
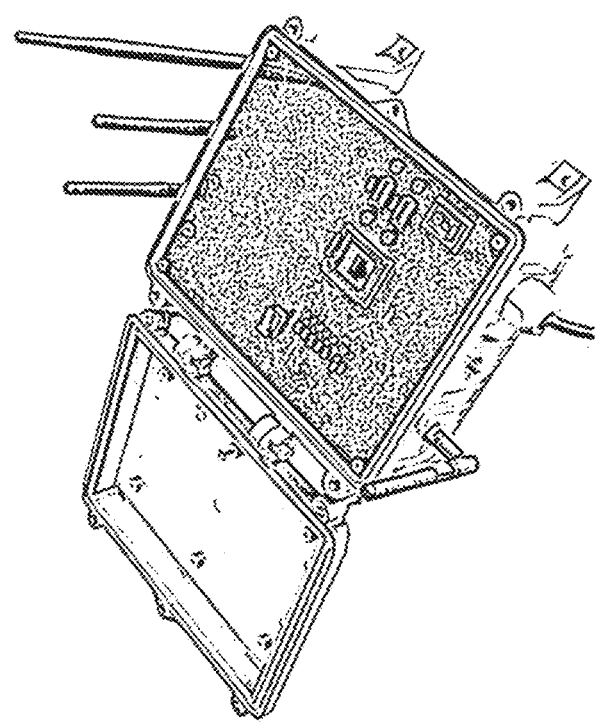
FIG. 24 depicts a ruggedized hub according to an embodiment of the invention for work site deployment and communications to embedded sensors and local wireless network for remote server access etc.

Within the embodiments of the invention presented supra in respect of FIGS. 19 to 23 and below in respect of FIGS. 24 to 26 particular emphasis has or may have been placed upon the SMAK as a discrete device communicating to a remote terminal, PDA, hub, PED, FED etc. However, it would be evident that multiple SMAKs may communicate to a single remote terminal, PDA, hub, PED, FED etc. and that the multiple SMAKs may communicate with each other and form an ad-hoc network or multiple ad-hoc networks with communication to the remote terminal, PDA, hub, PED, FED etc. undertaken via a master node within an ad-hoc comprising master é slave nodes or any nodes able to access the remote terminal, PDA, hub, PED, FED etc. Referring to FIG. 24 there is depicted a ruggedized hub according to an embodiment of the invention established by the inventors. The hub can communicate with SMAKs and other environmental and/or monitoring sensors as well as coupling to one or more local wireless networks in order to access remote storage, e.g. cloud-based storage on remote servers.

Within the embodiments of the invention presented supra in respect of FIGS. 19 to 24 and below in respect of FIGS. 25 and 26 particular emphasis has or may have been placed upon the SMAK as a discrete device with single sensor or multiple sensors operating at a single location within a formwork of poured concrete. However, referring to FIG. 25 there is depicted a SMAK according to an embodiment of the invention. As depicted the SMAK 2500 comprises processor 1910, wireless transceiver 1920, and battery 1930 together with multiple sensors 1960 with a shell 1970 and filler 1980. With multiple sensors 1960 distributed along the SMAK 2500 measurements may be made of temperature gradient(s) and/or humidity gradient(s) through the user of multiple temperature sensors and/or multiple humidity sensors. The measurement of gradients is critical in concrete industry as it is important to ensure the temperature gradient is not too high, for example below 20° C. to prevent cracking. With respect to humidity it is important to measure the evaporation rate or drying/wetting rate. It would be evident that the concrete surface dries faster but a SMAK embedded within the cross section of the concrete can be very useful in monitoring the humidity changes and gradients.

It would evident that the SMAK may include a single or multiple pressure sensors allowing the depth at which the SMAK sensor is embedded within the concrete to be calculated based on the hydraulic pressure of the fresh wet concrete. This information can be used for adjusting the curing temperature or applying the floor covering when it reaches a certain humidity level.

Figure 26:
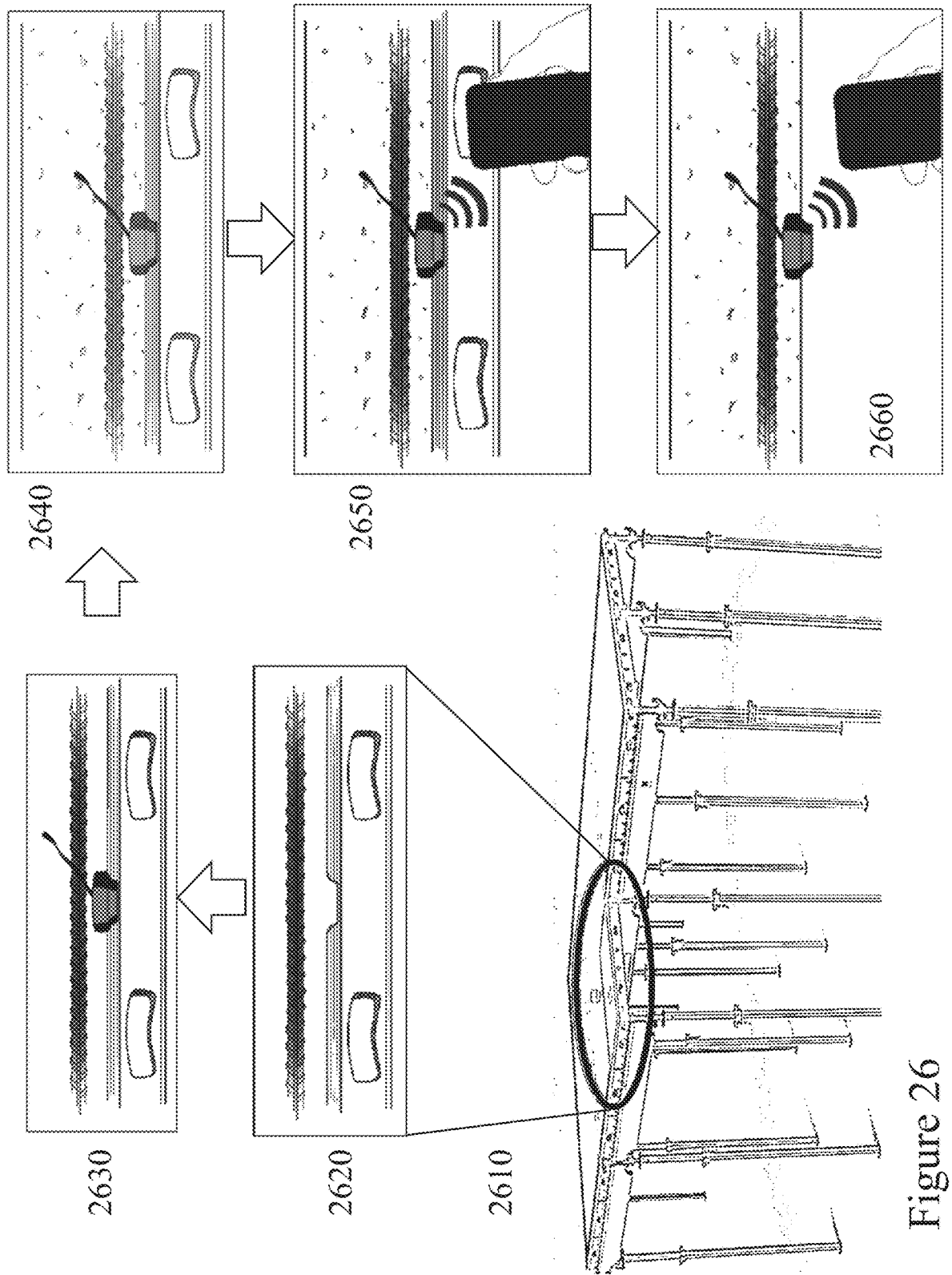
FIG. 26 depicts a schematic deployment method for embedded sensors according to embodiments of the invention in conjunction with formwork.

Now referring to FIG. 26 there is depicted an alternate methodology according to an embodiment of the invention wherein SMAK(s) are embedded in or mounted onto formwork panels. Accordingly, referring to FIG. 26 a formwork is depicted in first image 2610 comprising a series of panels which in this instance are upon posts for the formation of a concrete ceiling/roof. Accordingly, as depicted in second image 2620 the panel(s) have mounting points for the SMAK(s) such that as depicted in third schematic 2630 the SMAK is added to the formwork which may already have rebar formed across. Subsequently, as depicted in fourth image 2640 the concrete is poured onto the formwork such that the end user can monitor in fifth image 2650 the concrete curing/setting. Subsequently, with the removal of the framing of the formwork the end user may continue to monitor the subsequent cure and performance of the concrete. In this manner the formwork company may sell smart panels with the relevant information in the sensor. The sensors could have multiple leads for monitoring the temperature of concrete as well as the ambient temperature for curing optimization. It can also have a LED light to go green when the strength reaches a certain level and the formwork is ready to strip or vibrate/buzz etc.

Within the embodiments of the invention presented supra in respect of FIGS. 19 to 26 particular emphasis has or may have been placed upon the storing of data relating to the material(s) being monitored within the SMAK(s). However, within an alternate embodiment of the invention the SMAK performs only measurements with or without calibration according to the design/configuration of the SMAK. The acquired sensor data is then transmitted to a local or remote host such as a remote terminal, PDA, hub, PED, FED etc. Considering, a user employing a smartphone then their smartphone has installed upon it an application associated with the material and/or a material producer depending upon the willingness of the material producer to have their calibration information within a multi-producer application or solely an application linked to them. Accordingly, a material producer, for example a concrete producer may upsell their concrete to an end user as "smart concrete." Within this embodiment of the invention the SMAKs may be within the concrete as delivered by the producer's but within other embodiments of the invention the producers may deliver the concrete without SMAKs. The end user may purchase these from the concrete producer and install them in their job site. The end user will then download or access the concrete producer's application, assign the corresponding mix name to the SMAK(s) deployed and obtain data relating to their concrete pour such as strength values and other parameters.

Figure 27:
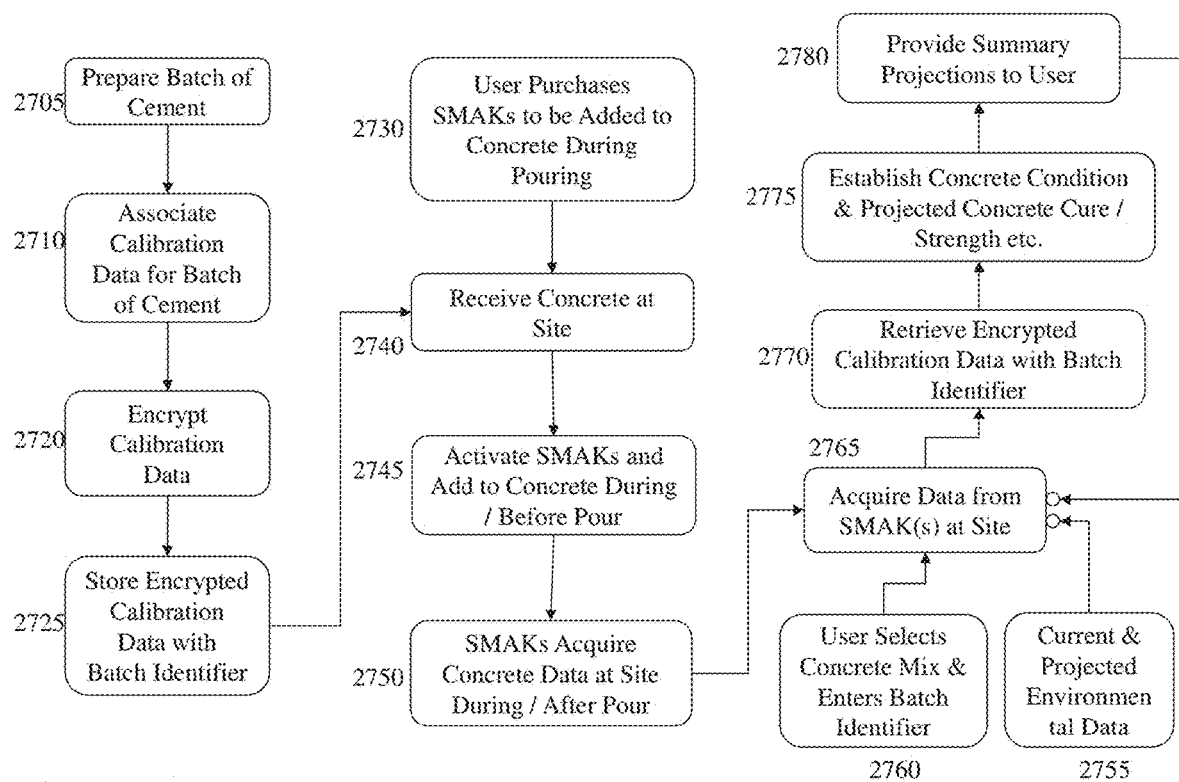
FIG. 27 depicts an exemplary process flow for an embedded sensor methodology for data logging concrete properties for concrete delivered to a worksite wherein the characteristics of the concrete are stored within a PED/cloud datafile accessible to a software application downloaded to a user's PED where the user merely selects the mix procured.

Now referring to FIG. 27 there is depicted an exemplary flow for SMAK methodology for data logging concrete properties from pouring, curing, and subsequently according to an embodiment of the invention wherein the SMAK is deployed in conjunction with poured cement. Whilst the following description relates to delivery of pre-mixed concrete it would be evident that the methodology described may be similarly employed with on-site concrete preparation a pre-packaged concrete mix comprising cement, sand, and ballast to which only water is required to be added. Accordingly, the process begins with step 2705 wherein a batch of cement is prepared wherein in step 2710 the calibration data, for example the maturity calibration curves, are associated with that batch. Next in step 2720 this calibration data is encrypted and then in step 2725 this encrypted calibration data is stored within cloud storage together with the batch identifier for subsequent retrieval and use by a software application in execution upon a PED and/or FED. The mixed concrete is delivered to the worksite in step 2740. At a preceding point in time the user purchases one or more SMAKs which they intend to add to the concrete pour(s) at the worksite. Accordingly, in step 2745 the SMAKs are activated (if necessary) and added to the concrete during the pour or as discussed supra in respect of FIG. 8 these SMAKs may be pre-located within the formwork of the worksite prior to the concrete pour.

Accordingly, in step 2750 the SMAK(s) acquire data from activation onwards which is subsequently acquired in step 2765 from the SMAK(s) through a device such as PED executing a SMAK software application (SSA) which can communicate with the SMAK(s) directly, through a hub such as depicted in FIG. 24, or accesses a hub which consolidates data from a plurality of hub(s). The SSA in step 2765 also accumulates current and/or projected environmental data from local sensors, PED sensors, online resources, etc. which was acquired in step 2755 and the concrete mix/batch information in step 2760. The SSA then retrieves the encrypted calibration data of the concrete mix wherein the decryption key is unique to the batch identifier and provided to the user with the batch delivery. Accordingly, using the retrieved calibration data in combination with the acquired SMAK(s) data the SSA establishes in step 2775 the concrete condition as well as projected cure/strength information are established and then provided to the user in step 2780. These process steps 2765 to 2780 may be repeated periodically by the user.

Optionally, the SSA may simply push data to a remote cloud server for processing in combination with the decrypted concrete calibration data etc. such that whilst the results are provided back to the user's PED/SSA they are also archived upon the remote server. Optionally, the SSA and/or remote application may store raw SMAK data as well as the processed data from the SMAK(s). Optionally, a tagged SMAK may be deployed with the concrete which has been added by the concrete producer so that the specific mix is identified from the tagged SMAK rather than mix selected by the user from a drop-down menu.

Within embodiments of the invention the SSA may be generic such that any manufacturer/provider of concrete may exploit the SSA/SMAKs provided that their calibration data is formatted according to the SSA file format. A manufacturer may elect to store their calibration data within the SSA/remote database in encrypted or non-encrypted form. Within other embodiments of the invention the SSA may be specific to a manufacturer/producer wherein the SSA may upon selection of a mix of that manufacturer/producer extract data from specific web locations exploiting coded HTML addresses against that specific mixture.

Within other embodiments of the invention this concept may be extended to bagged concrete, for example. Instead of putting the sensor in the bag, the sensor will be offered/purchased separately by the end user. The end user then gets the mix assigned to the sensor through scanning, for example, a QR code, bar code, or entering a product identifier to the mobile application or web based application depending on what they use. Within these embodiments of the invention the concrete producers do not release proprietary mix calibration information. Rather this is stored upon a remote server executing an application to which the web based application and/or mobile application communicate. Alternatively, the information may be downloaded to a PED executing a mobile application in an encrypted form and a subscription/registration etc. may be required in order for the user's PED to acquire the decryption key.

Within the embodiments of the invention presented supra in respect of FIGS. 19 to 27 particular emphasis has or may have been placed upon electrical measurements as the basis of a sensor with respect to determining a property of the medium within which the sensor is disposed. However, it would be evident to one of skill in the art that in addition to DC resistance(s), DC potential(s), AC resistance(s), AC potential(s), conductivity etc. that sensors may be configured with a SMAK or within different SMAKs for a range of parameters including, but not limited to, temperature, pressure, light, acceleration, humidity, vibration, pH, and chloride content. More advanced SMAK(s) may provide dedicated hardware, functionality, and software to enable more advanced techniques such as nuclear magnetic resonance, electrochemical, X-ray diffraction, optical spectrometry, thermogravimetric analysis, a half cell, etc. as well as corrosion resistance etc.

Within the embodiments of the invention presented supra in respect of FIGS. 19 to 27 particular emphasis has or may have been placed upon inclusion of a battery within the SMAK(s). Such a battery may be charged and connected permanently to the internal circuitry of the SMAK or connected based upon an event/trigger. In some embodiments of the invention the SMAK may be in a low power sleep mode until awoken by wireless command. Alternatively, detection of conduction between pins via the wet concrete, vibration, impact, pressure etc. may form events/triggers in isolation or combination. In other instances, the SMAK is only charged at the time it is going to be deployed such as through a wireless charging interface. Within other embodiments of the invention electrical power may be generated by the SMAK such as through piezoelectric charging, electrochemical charging from electrodes in the alkaline pore solution in concrete etc. Piezoelectric charging may be via vibration, strain, compression, etc.

Within the embodiments of the invention presented supra in respect of FIGS. 19 to 26 particular emphasis has or may have been placed upon the storing of parameters relating to cement and/or concrete upon a SMAK. However, it would be evident that in other embodiments of the invention the parameters may relate to mortar or an admixture for addition to concrete. Further, in other embodiments of the invention the parameters may relate to one or more components of the material being monitored, such as a glue within chipboard/fiberboard manufacture (e.g. MDF), a resin and é or fiber within fiber reinforced composites/fiberglass etc.

Optionally, the SMAK may be associated with a product, e.g. a bag of cement without any data for the properties etc. being stored within it. Accordingly, the requisite data may be attached to the product at a subsequent point in time through the use of a barcode, RFID tag, tag etc. and subsequently read by a PED for entry into an application in execution upon the PED wherein the SMAK is subsequently "programmed" based upon data being communicated to it from the PED. Optionally, the SMAK may be a smart tag attached to the packaging which is interrogated during the storage, shipment, retail stages of the product life cycle such that the SMAK is updated at each stage as a result of the interrogation with data relating to that interrogation etc.

Within another embodiment of the invention a SMAK may include one or more vibratory elements such that the SMAK may vibrate and adjust its depth within the freshly poured concrete based upon pressure measurements to determine when the SMAK is at the right depth. The SMAK may move towards the concrete surface or move to the bottom based upon depending upon the density of SMAK. In other embodiments of the invention the SMAK may position itself such that wireless reception is achieved.

Advanced Maturity Method

Early, rapid and accurate in-situ estimation of the compressive strength of concrete is one of the major challenges for the concrete industry. An accurate and reasonable in-situ estimation of the compressive strength provides the opportunity to optimize the concrete mix design as well as optimizing the formwork removal time. The optimization of mix design affects the consumption of raw materials (e.g. cement and aggregates) and alternative materials (e.g. natural pozzolans and supplementary cementitious materials like fly-ash and silica-fume). Considering the high volume global consumption of concrete, this could, in turn, effectively optimize the consumption of resources and reduce a great extent of $CO_2$ and toxic materials (emitted during the cement production) into the atmosphere.

The maturity method is a convenient approach to predict the early age strength gain of concrete, using the principle that the concrete strength is directly related to the hydration temperature history of cementitious paste. The maturity concept for estimating the strength gain of concrete is described in American Society for Testing and Materials (ASTM) standard C1074, "Standard Practice for Estimating Concrete Strength by the Maturity Method". This method can potentially address many immediate challenges facing the concrete industry such as predicting appropriate time for formwork stripping and post-tensioning, especially at low temperatures while the strength development of concrete is hindered; and optimizing concrete mix design and concrete curing conditions (e.g. concrete heating at low temperatures or surface protection in hot-dry weathers). Lack of an accurate estimation of strength at early ages of construction is twofold: contractors either wait too long for next action (e.g. stripping formwork) which is costly due to delays in completing the project, or they act prematurely which could cause the concrete structure to crack—that would lead to future durability and performance issues—or even structural collapse.

In most construction sites, field-cured concrete samples are tested to strength at various ages during the first week since concrete is poured, in order to make a decision on formwork removal. For example, ASTM C873 offers a test method for cast-in-place cylindrical specimens. These specimens can be removed later for measuring the compressive strength of concrete in the lab. Usually, if the concrete reaches 75% of its designed strength, the structural engineers allow for the striping of forms. The problem, however, is that only one specimen is crushed for strength estimation. This is not necessarily accurate. This method is limited to use in horizontal and thick concrete elements like slabs. In addition, the construction crew is usually on the job site while they are waiting to hear about the compressive strength result from the laboratory. This adds to the cost of construction and its uncertainty decreases the efficiency of the construction. Although alternative methods such as concrete maturity exist, there is a traditional resistance to utilizing them for most concrete projects. Such approaches to compressive strength evaluation may cause concrete contractors to make conservative decisions, face more complicated technical problem (e.g. delay in formwork stripping, and unnecessary long-term curing and surface protection), and spend more financial resources.

Maturity Method

As a non-destructive testing, the maturity method may be a reasonable candidate to fill this gap. In comparison to most on-site non-destructive technologies (e.g. Schmidt Hammer or Ultrasonic Pulse Velocity), the privilege that the maturity method stands on is that, the procedure for estimating the compressive strength would be objective and qualitative once the maturity curve is developed and adopted.

The maturity method is a relatively simple approach for estimating the in-place compressive strength of concrete, specifically at early ages less than 14 days. Once the maturity curve is developed in the laboratory for a specific project, it can be used for on-site estimation of compressive strength of concrete in real-time. The maturity method is governed by the fundamental assumption that a given concrete mix design poured during course of a specific project has the same compressive strength when it has the same "maturity index". This means that a given concrete mix design, for example, may reach the same compressive strength after 7 days of curing at 10° C. when it is cured at 25° C. for 3 days.

The maturity method based on the ASTM C1074 is the most commonly used method to estimate the in-situ strength of concrete today within the industry. ASTM C1074 provides two maturity functions: 1) Nurse-Saul function; and 2) Arrhenius function. Based on the Nurse-Saul method, there is a linear relationship between the maturity and the temperature in real time. The underlying assumption is that the strength development in concrete is a linear function of hydration temperature. Equation (3) shows the relationship between maturity and hydration temperature history where M(t) is the maturity index at time t, $T_{AVG}$ is the average temperature during the time interval $\Delta t$, and $T_0$ is a datum temperature.

$$M(t)=\Sigma[T_{AVG}-T_0)\cdot \Delta t] \quad (3)$$

ASTM C1074 provides a standard procedure to find the datum temperature for a specific mix design. However, most of previous studies suggest a practical estimation of the datum temperature between $-10° C. \leq T_0 \leq 0° C.$ Indeed, this is the temperature at which the hydration of cementitious paste stops; hence the strength development of concrete ceases. The inventors have established that this datum temperature lies between $-5° C. \leq T_0 \leq 0° C.$ dependent on the concrete mix design.

The second approach is the Arrhenius function that assumes there is an exponential relationship between the compressive strength and hydration temperature. The maturity index is defined in form of an equivalent age at a reference temperature. It means the actual age should be normalized to the reference temperature in order to estimate the compressive strength. This function needs a value of activation energy that can be determined as the procedure detailed in ASTM C1074. Despite the fact that the Arrhenius function is scientifically more accurate, the Nurse-Saul function is more commonly used by concrete industry for the following reasons:

accuracy of the Nurse-Saul function is adequate for most field applications;

the Nurse-Saul function is relatively simpler compared with the Arrhenius function.

There is another method proposed by Papadakis and Bresson for the calculation of Maturity index called weighted maturity. In this method the weighted maturity is expressed by Equation (4) where M(t) is the weighted maturity (° C.h), $t_K$ is the hardening time of concrete corresponding to $(T_i-T_j)/2$, $T_K$ the hardening temperature interval $(T_i-T_j)$ in ° C., C is an experimental coefficient which depends on the cement type and $n_K$ is the temperature-dependent parameter for $T_K$. This maturity method is adopted by Dutch standard NEN 5970, entitled 5970 "Determination of Strength of Fresh Concrete with the Method of Weighted Maturity", and is currently being used in some European countries, including the Netherlands.

$$M(t)=\Sigma[t_K,T_K,C^{n_K}] \quad (4)$$

ASTM C1074 provides a step-by-step guide for developing the maturity curve, and for estimating the compressive strength. These steps include the following as the maturity-strength curve represents the relationship between maturity index and compressive strength for a specific concrete mix design, adopted in the laboratory. To do so, adequate concrete cylindrical specimens should be casted, and then stored in the semi-adiabatic condition for curing. Certain number of concrete cylinders (i.e., at least two concrete specimens) should be equipped by embedded temperature sensors for recording the hydration temperature history. The compressive strength of concrete is measured at ages of 1, 3, 7, 14 and 28 days. This being depicted schematically in FIG. 28.

The maturity index is calculated at strength testing times using Equation (1) and then the best curve will be fitted for the strength data versus maturity index data to obtain the maturity—strength curve as given by Equation (5) where M is the Maturity index, S is the in-situ compressive strength of concrete, and a and b are the experimental coefficients.

$$S = a + b \cdot \log(M) \tag{5}$$

This is depicted schematically in FIG. 29. It should be noted that it is important to test the concrete mix design that will be the same as that used in the construction project. Any deviations from the original mix design (such as water to cement ratio, cement content, etc.) will reduce the accuracy of the maturity method to estimate the compressive strength.

Once the maturity—strength curve is developed, it can be used to estimate the in-place concrete strength using the hydration temperature history. To do so, the temperature history of the concrete elements should be recorded after pouring using embedded sensors at the locations that are generally critical in term of exposure conditions, curing and structural requirement. Routine quality control tests should be performed to ensure the accuracy of the maturity—strength curve. These controls minimize any error in the estimation of in-place strength due to inherent limitations of the maturity method.

Some of important limitations of this method are listed as follows:
- In-place concrete is not representative of the concrete used to develop the calibration in the lab. This can be because of changes in materials, water to cement ration, air content, batching method, etc.;
- In-place concrete is not properly placed, consolidated, cured, etc.;
- Very high early-age temperatures can lead to inaccurate estimation of strength at later ages;
- Using a datum temperature (for the Nurse-Saul function) that is not representative of the concrete mixture can result in incorrect estimation of strength.

Figure 30A:
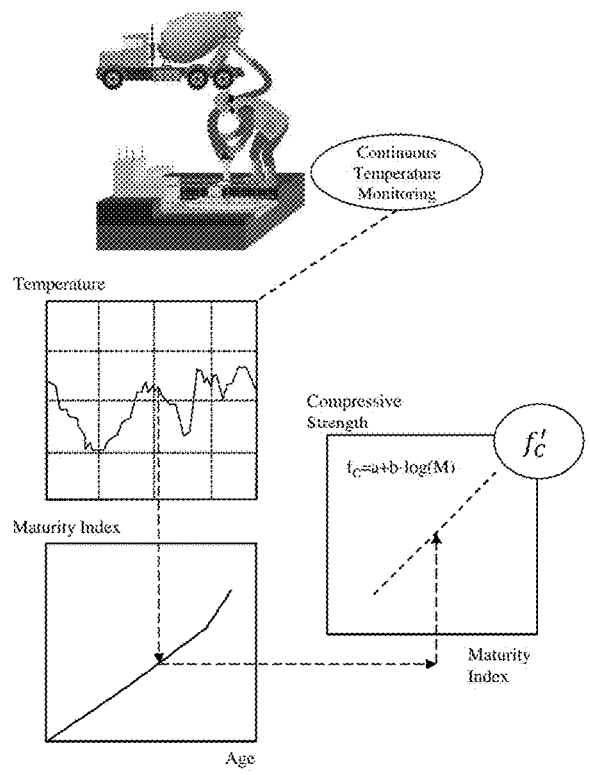
FIG. 30A schematically depicts how exploiting prior art test instruments employing ASTM C1074 estimate concrete strength from the maturity curve.
Figure 30B:
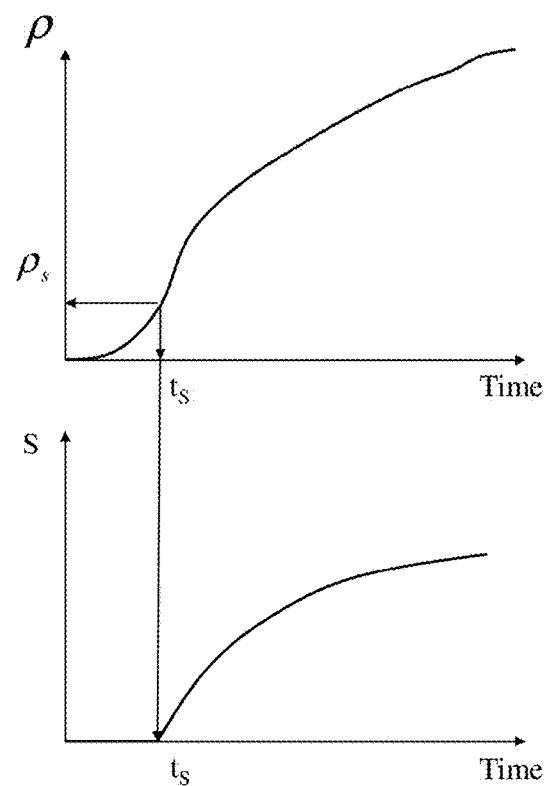
FIG. 30B depicts the electrical resistivity versus time curve of concrete whereby the resistivity value at which the concrete starts gaining strength can be identified from the inflection point in the curve.

Within the prior art several maturity devices have been established that can measure the hydration temperature of concrete in real time. Most of these devices can calculate the maturity index and predict the compressive strength if the maturity—strength curve, datum temperature and any required information are developed. Most of these devices include a temperature sensor embedded into the concrete elements that is plugged in the data logger via an electrical cable. Alternatively, a simple thermocouple could be embedded in concrete for temperature monitoring using a connected data logger. The data should then be extracted and used to calculate the maturity index and use it to estimate the concrete strength from the maturity curve. This is depicted schematically in FIG. 30A.

Advanced Maturity Concept

Except for specific and critical projects, the concrete industry shows interest in the commonly used compressive strength test. This is mainly due to the upfront cost of concrete mixture calibration for maturity curves, and lack of expertise for the installation of concrete temperature sensors, data collection and analysis. However, the inventors have established an advanced calibration technique to develop Maturity-Strength curves without the need to test the compressive strength of concrete in the laboratory at all five ages (i.e., breaking 15 concrete specimens at ages of 1, 3, 7, 14 and 28 days). Within the embodiment of the invention according to the method established by the inventor's data from the electrical resistivity and concrete temperature is combined to derive the coefficients in the concrete maturity-strength relationship (i.e., a and b) without the need to conduct extensive compressive strength measurements.

An example of such combined calculations is described as follows. In this example, only one compressive strength test will be required at a standard age such as 7 or 28 days for example. The details of the technique are described below. The data established by the inventors shows that the compressive strength of concrete is the logarithmic function of the electrical resistivity of concrete in the saturated concrete condition as given by Equation (4) where $\rho$ is the electrical resistivity of concrete in saturated condition, S is the in-situ compressive strength of concrete, and c and d are the experimental coefficients, which are mix dependent.

$$S = c + d \cdot \log(\rho) \tag{6}$$

From Equations (5) and (6) the inventors derive the relationship between $\rho$ and M as given by Equation (7). Then by curve fitting of the experimental data, i.e. $\log(M)$ and $\log(\rho)$ in Equation (7) the relationships given by Equations (8) and (9) are derived where $X_1$ and $X_2$ are the intercept and slope coefficients obtained from the regression analysis (curve fitting).

$$\log(\rho) = \frac{(a-c)}{d} + \frac{b}{d} \cdot \log(M) \tag{7}$$

$$\frac{(a-c)}{d} = X_1 \tag{8}$$

$$\frac{b}{d} = X_2 \tag{9}$$

Figure 31:
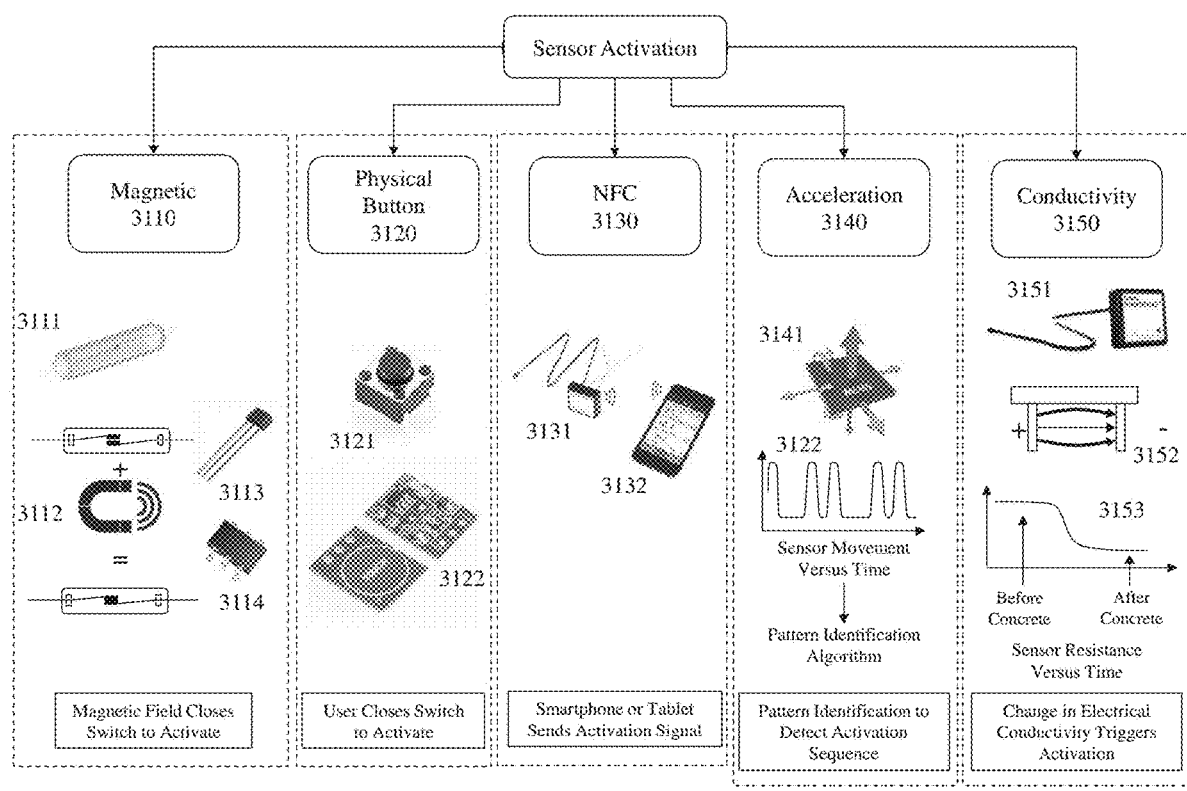
FIG. 31 depicts schematically examples of activation mechanisms for embedded sensors according to embodiments of the invention.

From the electrical resistivity—time curve, one can identify the resistivity value at which the concrete starts gaining the strength (i.e., the time at which "final setting" occurs in fresh concrete) which corresponds to the time when electrical resistivity increases rapidly (e.g. the inflection point on the curve shown) as depicted in FIG. 31. Therefore, by substituting in Equation (4) we obtain the relationship in Equation (8) where $\rho_S$ is the electrical resistivity of concrete at the time of strength gain initiation point (i.e. strength is zero at this point). Knowing the strength of concrete at any age such as 7 days or 28 days ($S_t$), we can also derive the relationship of Equation (9) from Equation (4) where $S_t$ is the compressive strength of concrete at time t and $\rho_t$ is the electrical resistivity of concrete at time t. By solving Equations (10) and (11) the unknown variables c and d are obtained. Substituting the values of these two variables into Equations (8) and (9) then the maturity coefficients a and b are determined which can then be used in Equation (5) for the strength prediction using the maturity concept.

$$\frac{c}{d} = -\log(\rho_s) \tag{10}$$

$$S_t = c + d \cdot \log(\rho_t) \tag{11}$$

Electrical Resistivity Determination in Concrete

Within embodiments of the invention described supra and depicted in respect of FIGS. 19 to 30 the "SMArt rocKs"

(SMAKs) and the Advanced Maturity Method the electrical resistivity is measured as part of the measurements. It is noted that there is a temperature dependence of this measurement and that there is an associated activation energy. However, the electrical resistivity measured is also impacted by the presence of humidity and the water content of the concrete. If we were to consider calculating concrete resistivity then we would need to consider the water-cement (w/c) ratio, the temperature, relative humidity, hydration time and the cover thickness of concrete.

For a given hydration time and w/c ratio the concrete pore saturation with relative humidity may be established from adsorption isotherms or alternatively estimated from measurements made by SMAKs deployed within the concrete. Considering the w/c ratio and the degree of saturation of the concrete then a correction factor may be established to the measured electrical resistivity made with the SMAKs deployed within the concrete. For example, scaling factors for measured electrical resistivity may be scaled based upon the variation of resistivity with saturation ($S_r$) and w/c ratio according to Equations (12) and (13) respectively below for different saturation ranges and w/c ratios wherein the coefficients are themselves functions of the saturation, i.e. $A_X=A_X(S_r)$ and $B_Y=B_Y(S_r)$.

$$\rho=+A_1(w/c)^3+A_2(w/c)^2+A_3(w/c)+A_4 \quad 0.4 \le (w/c) \le 0.48 \quad (12)$$

$$\rho=+B_1(w/c)^2+B_2(w/c)+B_3 \quad 0.48 \le (w/c) \le 0.7 \quad (13)$$

It would be evident that based upon these functions or other functional descriptions for resistivity versus one or more parameters such as saturation, relative humidity, w/c, etc. that scaling factors may be established and stored within the SMAK or an application accessing the SMAK data to provide a correction of the electrical resistivity before, during, or after any other scaling applied, such as for the temperature dependent activation of electrical resistivity for example. Specific details are given in the above description to provide a thorough understanding of the embodiments. However, it is understood that the embodiments may be practiced without these specific details. For example, circuits may be shown in block diagrams in order not to obscure the embodiments in unnecessary detail. In other instances, well-known circuits, processes, algorithms, structures, and techniques may be shown without unnecessary detail in order to avoid obscuring the embodiments.

Options and Refinements

Sensor Activation: In order to maximise sensor lifetime maintaining the battery life required for the sensing application is important. Accordingly, keeping the sensors inactive during their shelf life or transportation prior to use is beneficial. Accordingly, there is a requirement to activate the sensors when they are at the job site and prior to their installation so that they could be detected and connected to by the scanning devices. Alternatively, the sensors may be activated prior to deployment within the construction material at the point of manufacture or transportation to the job site. The hibernating (inactive) sensors will become temporarily/permanently active once triggered through one or more activation methods.

Within an embodiment of the invention the temporarily activated sensors could then be connected to via a scanning device and become permanently active and start their main function (for example datalogging). It would be beneficial that activating the sensors requires little to no additional equipment and must be as simple as possible to facilitate on site activation by unskilled individuals. Within embodiments of the invention the temporarily activated sensors could then be connected to via a scanning device and become inactive after a predetermined period of time or establish an operating mode with a generally low power state (sleep mode) with periodic activation to perform a measurement or transmit their data to a scanning device. Optionally, the devices within the generally low power state perform these periodic measurements according to a predetermined schedule and maintain this cycle unless an activation is received from a scanning device. As noted above these periodic measurements may be at a higher frequency during initial deployment and then at increasing lower frequencies established either based upon elapsed time or one or more determined characteristics of the material being monitored.

Activation of the SMAKs within embodiments of the invention may exploit one or more methods as depicted in FIG. 31. However, it would be evident that other sensor activation techniques may also be employed or that a combination of activation mechanisms may be required to activate a SMAK to avoid incorrect activation. As depicted in FIG. 31 the techniques include, but not limited to:

Magnetic: A magnetic field sensor within the SMAK may be employed to detect a request by the user to activate the sensor. Accordingly, as depicted in FIG. 31 within first block 3110 a reed switch 3111 is depicted wherein bringing a magnet 3112 into proximity of a SMAK comprising the reed switch at a certain predefined location closes the switch thereby activating the sensor. Alternately, solid state magnetically activated switches may be employed such as a Hall sensor 3113 and a magnetoresistive circuit 3114.

Button: As depicted in second block 3120 a physical switch may be employed as part of the SMAK such as, for example, a push button 3121 covered within a waterproof elastic membrane may be employed to allow a user to activate the sensor. Alternatively, a touch sensitive "button" 3122 may be provided.

Near Field Communication (NFC): A variety of electronic devices such as smartphones, tablets, dataloggers etc. are capable of communicating wireless through one or more NFC protocols. The NFC signal as depicted within third block 3130 exploits a wireless signal from a scanning device 3132 which can be received and translated into a request to activate the sensor 3131. This will then activate the main wireless communication process enabling the sensor to start logging and connecting with the scanning devices. Optionally, within an embodiment of the invention the initial NFC communication may be sufficient to power a predetermined portion of the SMAK thereby initiating an initial connection of the battery to the electronics within the SMAK such that the device is then self-powered from that point on. Accordingly, unlike magnetic and button based activations this as well as acceleration and conductivity described below require part of the sensor be active all the time to monitor for the activation signal.

Acceleration (Shaking, Impact etc.): Where the SMAK incorporates a sensor capable of detecting vibration and/or acceleration and is in a low power mode then a predetermined pattern of impact/acceleration may trigger the SMAK into an active mode where the predetermined pattern allows for the trigger pattern to be distinguished from an unintentional initiation. This being depicted in fourth block 3140 wherein a microelectromechanical system (MEMS) accelerometer 3141 generates an output signal 3142 in dependence upon motion and this is monitored for a match to the predetermined pattern. The predetermined pattern may for example be an intentional human generated acceleration via shaking the sensor or predetermined periodic motion such as where the sensor is within the rotating drum of a concrete truck etc. Such predetermined patterns allowing distinguishing of the intentional activation versus unintentional machine/setup generated vibrations etc.

Conductivity: Activation may also be triggered through the completion of an electrical circuit between a pair of electrical contacts upon the outer surface of the SMAK as depicted in fifth block 3150. This may, for example, be the same pair of electrical contacts which subsequently measure the conductivity of a material the SMAK is embedded within. Accordingly, as depicted the sensor 3151 applies a voltage to a first electrode and measures the resistance to a second electrode wherein the change in conductivity is detected as a drop in resistance or current flow through completion of the electrical circuit from the first electrode to the second electrode by the conductive material surrounding the sensor, e.g. wet concrete. The resulting change in the monitored characteristic triggers the sensor to move from a low power mode to one where measurements are logged etc. Alternatively, the contacts may be a different pair of contacts as the contacts for the measurement apply a voltage or current. Accordingly, the triggering may be via a user's finger touching the SMAK or the SMAK being deployed within an electrically conductive medium, such as wet concrete.

Embedded pH Sensor: The determination of concrete pH is of importance to the concrete industry since it provides an indication of the state of the steel reinforcement with respect to corrosion. Changes of in-situ pH can also be used to determine the rate at which other concrete degradation mechanisms are occurring. pH is a measurement of the concentration of hydrogen ions in a certain solution/medium. This can be determined through measuring the electrode potential of a pH electrode such as an ion-selective electrode made of a doped glass membrane that is sensitive to hydrogen (or other specific ions), a solid-state pH electrode, or an Ion Sensitive Field Effect Transistor (ISFET) for example. Such pH sensors may form part of one or more SMAK configurations according to embodiments of the invention.

Concrete Pore Solution Conductivity Measurement from pH: As concrete is a porous material, the conductivity of solution available in pores within the concrete is of interest in specific applications. Since pH is a measure of the concentration of hydrogen ions in the solution, such a measurement can be employed to determine the concentration of hydroxyl ions or alkali concentration in solution. The alkali concentration can therefore indicate the resistivity of the pore solution which is beneficial for determining several properties of the concrete. For instance, if the conductivity of the pore solution is determined along with the overall conductivity of concrete then a parameter called the Formation Factor can be calculated which provides information regarding the total porosity, tortuosity and pore connectivity of the concrete.

Water/Cement Content from Overall Concrete Resistivity and Pore Solution Resistivity: The electrical conductivity of water is orders of magnitude higher than that of other components of plastic concrete, i.e. concrete that has not yet set, such as aggregates or cement particles. Therefore, a measurement of the electrical resistivity of concrete can determine, indirectly, the amount of water in a specific volume of concrete. However, the conductivity of mixing water changes throughout mixing due to an ongoing chemical interaction with cement and chemical admixtures. Therefore, a measurement of the conductivity of the water is an important element, in addition to the conductivity of the whole concrete mixture, in the process of determining the water-to-cementitious-materials (W/CM) ratio. Accordingly, a SMAK capable of determining the resistivity of the overall concrete as well as the conductivity of the pore solution (determined either indirectly, through measuring the medium's pH, or directly, through the changes of conductivity of an embedded porous material), can establish the W/CM ratio of the concrete it is embedded within. Accordingly, the W/CM ratio may be established in-situ during casting with one or more SMAKs comprising sensors for pore solution conductivity and overall electrical resistivity or alternatively during transportation using one or more SMAKs or one or more dual sensor-based devices either mounted to a concrete truck or forming part of a mixer drum, a mixer blade upon the inner surface of the mixer drum or a mixer blade within the mixer drum.

Figure 32A:
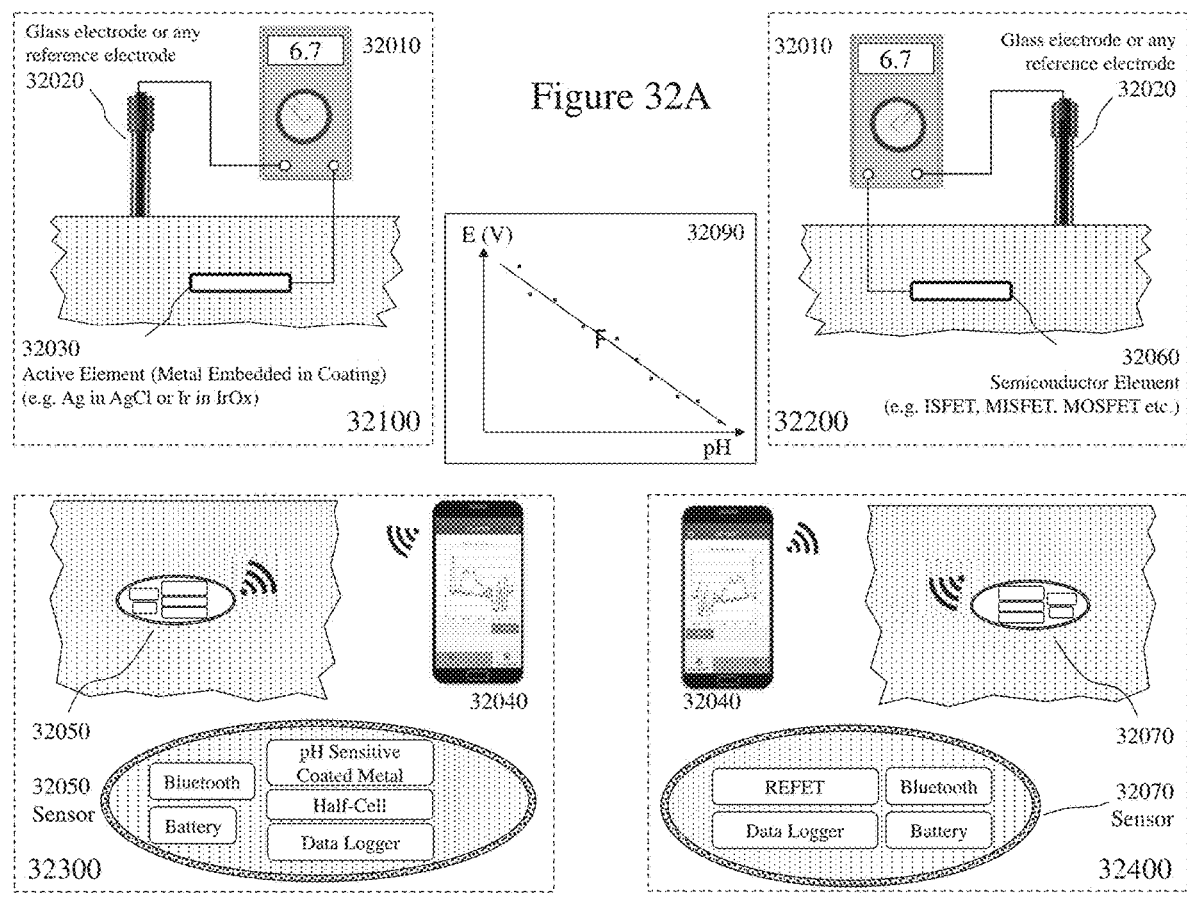
FIG. 32A depicts exemplary embedded and partially embedded sensor configurations for establishing pH according to embodiments of the invention.

Referring to FIG. 32A there are exemplary embedded and partially embedded sensor configurations for establishing pH according to embodiments of the invention within first to fourth images 32100 to 32400 respectively. Within first image 32100 a partially embedded sensor configuration is depicted wherein a measurement device 32010 is connected to a reference electrode 32020, e.g. a glass electrode as known in the art, connected to the surface of the concrete as described above in respect of FIG. 4B or via a conductive pad such as described in respect of FIG. 3. The device 32010 is also connected to an active element 32030 embedded within the concrete such as a metal element embedded within a coating such as Ag in AgCl or Ir in IrOx. Within second image 32200 the device 32010 and reference electrode 32020 are the same but the active element is now a semiconductor element 32060 such as an ISFET, MISFET, MOSFET etc.

Within third image 32300 an embedded sensor 32050 exploiting the concept depicted in first image 32100 is depicted which performs the measurements of measurement device 32010, reference electrode 32020, and active element 32030 but within a self-contained sensor, the embedded sensor 32050. As depicted the embedded sensor 32050 contains a data logger, a half-cell for the reference electrode, a pH sensitive coated metal, a battery, and a Bluetooth transceiver which allows data to be transferred from the embedded sensor 32050 to a device 32040. Other elements, not depicted in third image 32300, may form part of the embedded sensor 32050.

Within fourth image 32400 an embedded sensor 32070 exploiting the concept depicted in second image 32200 is depicted which performs the measurements of measurement device 32010, reference electrode 32020, and semiconductor element 32060 but within a self-contained sensor, the embedded sensor 32070. As depicted the embedded sensor 32070 comprises a REFET, datalogger, battery and a Bluetooth transceiver which allows data to be transferred from the embedded sensor 32070 to a device 32040. Other elements, not depicted in fourth image 32400, may form part of the embedded sensor 32050.

Figure 32B:
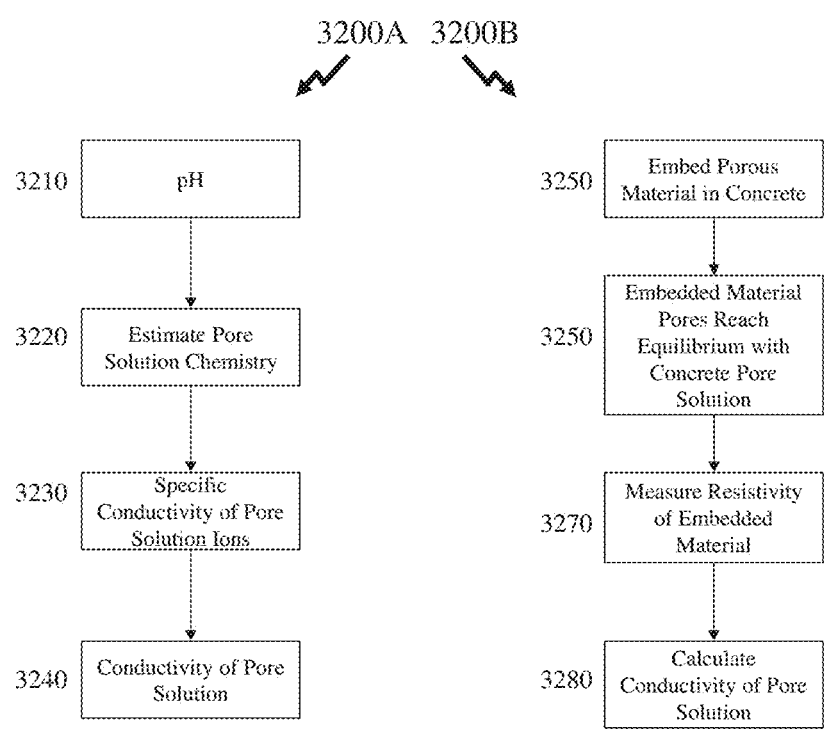
FIG. 32B depicts process flows for establishing pore solution conductivity via embedded porous elements forming part of the sensors in contrast to a pH based methodology.

Equally many construction materials, such as concrete for example, are porous materials when "cured" or "set" and as a result, either from initially being in liquid or slurry form, retaining water when cured or subsequently absorbing moisture, the conductivity of the solution available in pores within the construction material is of interest in defining specific aspects of the construction material in different deployment applications of the construction material. Referring to FIG. 32B there are depicted exemplary process flows for determining the conductivity of this solution exploiting embodiments of the invention through either pH measurements or embedding a porous material forming part of a sensor within the construction material. Considering the pH based route then this is depicted in first process flow 400A comprising first to fourth steps 3210 to 3240 respectively, these being:

First step 3210 wherein the SMAK acquires a pH measurement using a pH sensor such as an ISFET for example;

Second step 3220 wherein the pore solution chemistry is estimated for the construction material either generally or in dependence upon the pH measured;

Third step 3230 wherein for the pore solution chemistry established; and

Fourth step 3240 wherein the pore solution conductivity is established.

It would be evident that steps 3220 and 3330 may have been performed previously and that step 3310 therefore in the measurement of the pH leads to establishing the pore solution conductivity in step 3340 from a lookup table, application of one or more algorithms previously established etc. As with the consideration of maturity curves etc. discussed above such lookup table(s), algorithms etc. may be stored within the SMAK allowing direct establishment of the pore solution conductivity by the SMAK which is communicated to any scanning device and therein to the cloud-based storage etc. or the raw pH value is acquired by the scanning device and the calculations performed upon it or remotely within the cloud-based application(s) associated with the acquisition, processing, and storage of data relating to SMAKs within construction materials. Alternatively, as described the pore solution chemistry and pore solution ion conductivities are established real time either generally or specifically in dependence upon the pH.

It may be noted that dielectric constant of the construction material as described and discussed with respect to embodiments of the invention is dependent upon the water content as water has a high dielectric constant of 81 versus the other components of construction materials such as concrete, gypsum etc. The dielectric content for dry concrete is approximately 2-4 when measured using microwave/RF propagation. Accordingly, this allows for measurement data relating to the pore solution conductivity and moisture/water content to be obtained where measurements are performed below approximately 10 GHz versus those performed above this frequency. Below this frequency the loss factor of the construction material can be significantly impacted by the increase of pore solution conductivity arising from ions such as chloride for example. Whilst the ionic content of the pores does not significantly affect dielectric constant, although there is some dependence, the loss factor which causes attenuation can be changed due to the increase in ohmic conductivity. In cement mortar, both conductivity and dielectric constant increase with larger amounts of sodium and chloride ions. This affect can also change with the water/cement (w/c) ratio as the impact on pore structure from chloride ions, within materials such as Portland cement based mortar, varies with w/c ratio. Accordingly, additional data relating to pore solution conductivity, moisture/water content and pore size can be determined from the loss measured in conjunction with a microwave/RF based dielectric constant measurement.

Referring to second process flow 3200B a methodology based upon measuring the conductivity of the solution within the construction material is presented comprising first to fourth steps 3250 to 3280 respectively. These comprising:

First step 3250 wherein the SMAK is embedded within the construction material, e.g. concrete, as described in respect of SMAKs previously but the SMAK now includes a porous material in direct contact with the construction material;

Second step 3260 wherein the embedded porous material reaches chemical equilibrium with the pores within the construction material;

Third step 3270 wherein for the resistivity of the embedded material is measured; and Fourth step 3280 wherein the pore solution conductivity is determined in dependence upon the change of resistivity of the embedded material.

Accordingly, if the pore solution changes then the equilibrium state with the embedded porous material will subsequently adjust such that the ongoing resistivity allows for ongoing determination in respect of changes in the pore solution of the construction material.

Figure 33:
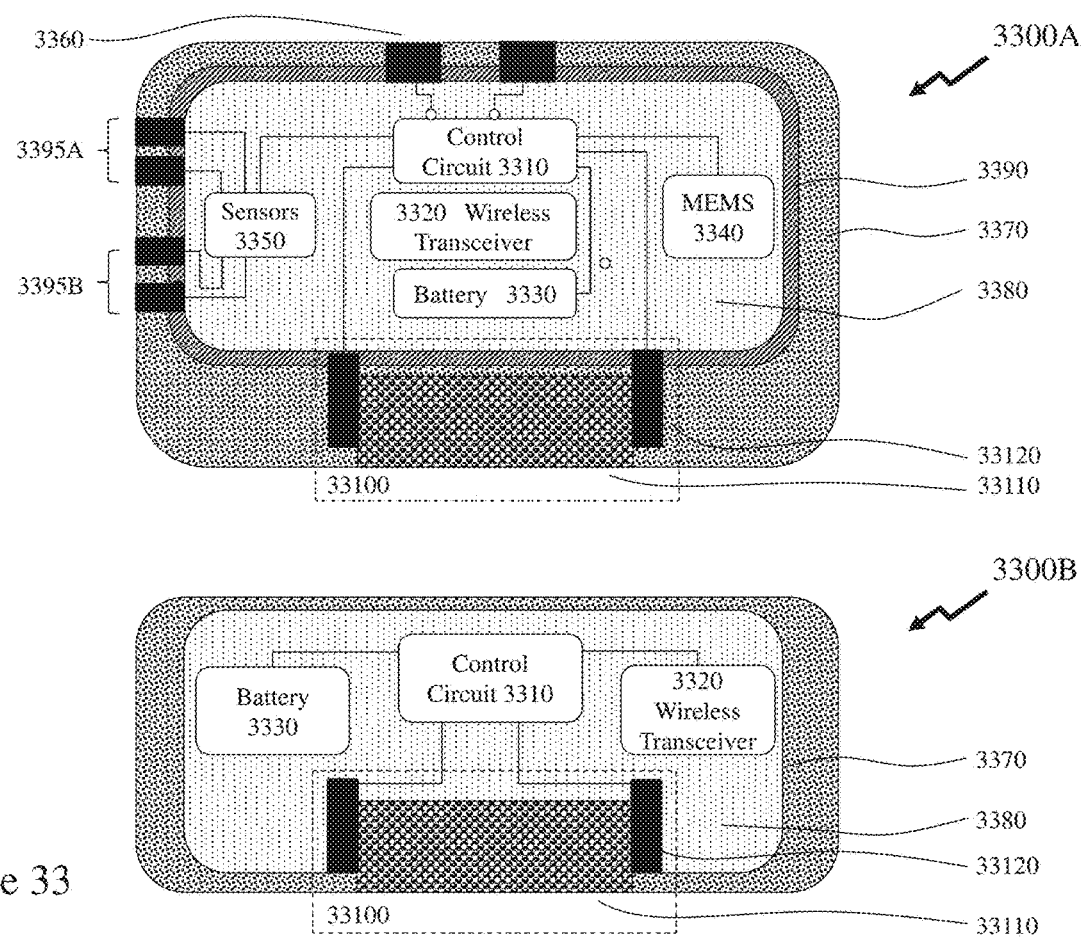
FIG. 33 depicts exemplary embedded sensor concepts for establishing pore solution conductivity via embedded porous elements forming part of the sensors.

Referring to FIG. 33 there are depicted exemplary SMAK designs 3300A and 3300B according to embodiments of the invention. In first SMAK design 3300A the SMAK comprises the control circuit 3310, wireless transceiver 3320, battery 3330, MEMS 3340, and sensors 3350 which are coupled to first and second SENsor INTerfaces (SENINTs) 3395A and 3395B. The control circuit 3310 is also coupled to contacts 3360 and a resistivity sensor 33100 comprising a porous material 33110 and contacts resistivity 33120. The porous material 33110 is exposed to the external environment such that when embedded within the construction material the porous material 33110 can reach equilibrium with the solution portion of the construction material. Accordingly, the control circuit 3310 can establish resistivity measurements for the resistivity sensor 33100. As depicted the SMAK comprises an intermediate casing 3390 which encapsulates the sensor filler 3380, e.g. a foam, air, etc. and is surrounded by an outer shell 3370. As depicted the porous material 33110 is entirely external to the intermediate casing 3390 and only resistivity contacts 33120 extend through it for the resistivity sensor 33100 although other contacts 3360 and first and second SENINTs 3395A and 3395B also do.

In second SMAK design 3300B the SMAK is reduced in complexity to the control circuit 3310, wireless transceiver 3320, and battery 3330 together with the resistivity sensor 33100 comprising porous material 33110 and resistivity contacts 33120. In this embodiment the porous material 33110 is not outside an intermediate casing and is depicted as being within both the outer shell 3370 and filler 3380 although it would be evident that according to the filler 3380 that the outer shell 3370 may be omitted.

Optionally, a SMAK comprising a porous sensor 33100 may be stored such that the porous material is sealed prior to use such as by the use of a peel-off cover or sealing the SMAK within a bag discretely or in combination with a material such as a desiccant or solution of predetermined and known composition. Optionally, a solution may be added to the porous material 33110 prior to deployment, e.g. deionized water.

In-Situ Workability/Slump Measurements: As noted above in respect of FIG. 3 the slump of concrete is evaluated at present using a slump test 330 wherein a cone is filled with the concrete and subsequently after removal of the cone the resulting slump of the concrete is measured. However, this measurement must be made at the work site either before, during or after a pour wherever the operator can do so on the work site. Accordingly, it would be beneficial to provide an automated measurement of workability/slump within the truck transporting the concrete to the work site. The drum of a concrete truck rotates with a blade or blades, typically a spiral blade, that continues to mix the concrete during transportation. Optionally, one or more additions may be made to the concrete during transportation such as water or an admixture wherein the rotation and blade ensure thorough mixing.

As the drum rotates the displacement of the plastic concrete within the mixer varies according to its characteristics which correlate to its viscosity, consistency and yield stress. Accordingly, the displacement of the plastic concrete within the mixer can be determined through resistivity meters fixed at the mixer wall such that the measurement system continuously collects resistivity data which can be correlated to the duration of contact between the concrete mixture and the plurality of sensors for each rotation. Knowing this duration at each rotation cycle, the extent of displacement of concrete within the mixer can be determined and correlated to the slump/workability of the concrete mixture. The rotation rate of the mixer drum may be derived from the resistivity data, from a different sensor, or from the controller of the motor driving the drum for example.

Figure 34:
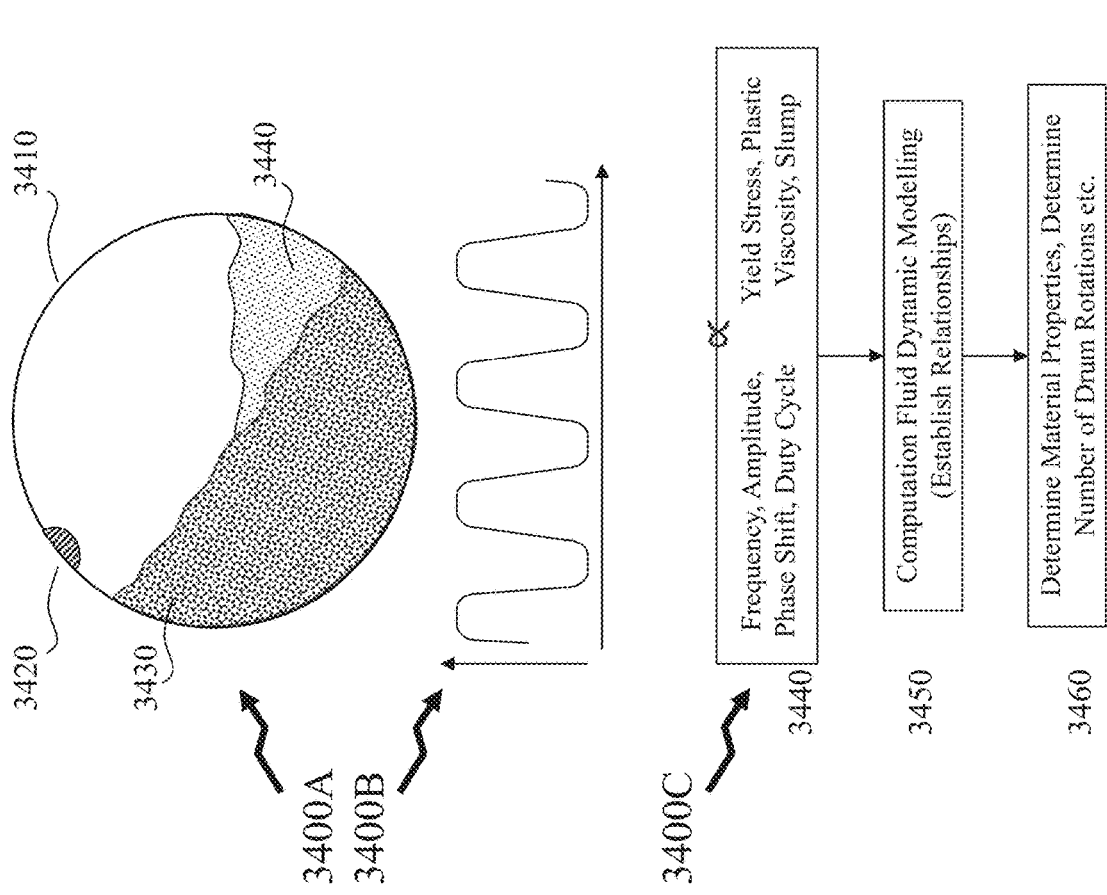
FIG. 34 depicts schematically determination of workability (slump) during transportation of concrete according to an embodiment of the invention.

This is depicted within FIG. 34 wherein first image 3400A depicts schematically the drum 3410 with an electrical resistivity sensor 3420 deployed upon the drum 3410. At rest the concrete mixture fills the bottom of the drum as first material 3440 but as the drum 3410 rotates the concrete mixture is rotated around the drum 3410 according to the properties of the concrete mixture, this being depicted as second material 3430. Accordingly, the electrical resistivity monitored by the sensor 3420 exhibits a time dependent response as indicated in second image 3400B wherein the electrical resistivity is high when the sensor 3420 is in the air and low when the sensor 3420 is within the concrete material. Accordingly, referring to third image 3400C a schematic flow diagram of analysis is presented wherein in first block 3440 the frequency, amplitude, phase shift (between the resistivity fluctuation cycles and the drum revolution cycles), and duty cycle of the electrical resistivity measurement are proportional to the yield stress, plastic viscosity and slump. In second block 3450 computational fluid dynamic (CFD) modelling is employed to establish the relationships between these parameters allowing in third block 3460 for the material properties from the measured response of the sensor 3420 during rotation of the drum 3410. Additionally, the measured response of the sensor 3420 during rotation of the drum 3410 allows for determination of frequency of rotation, number of rotations of drum completed during transportation of the concrete etc.

Figure 35:
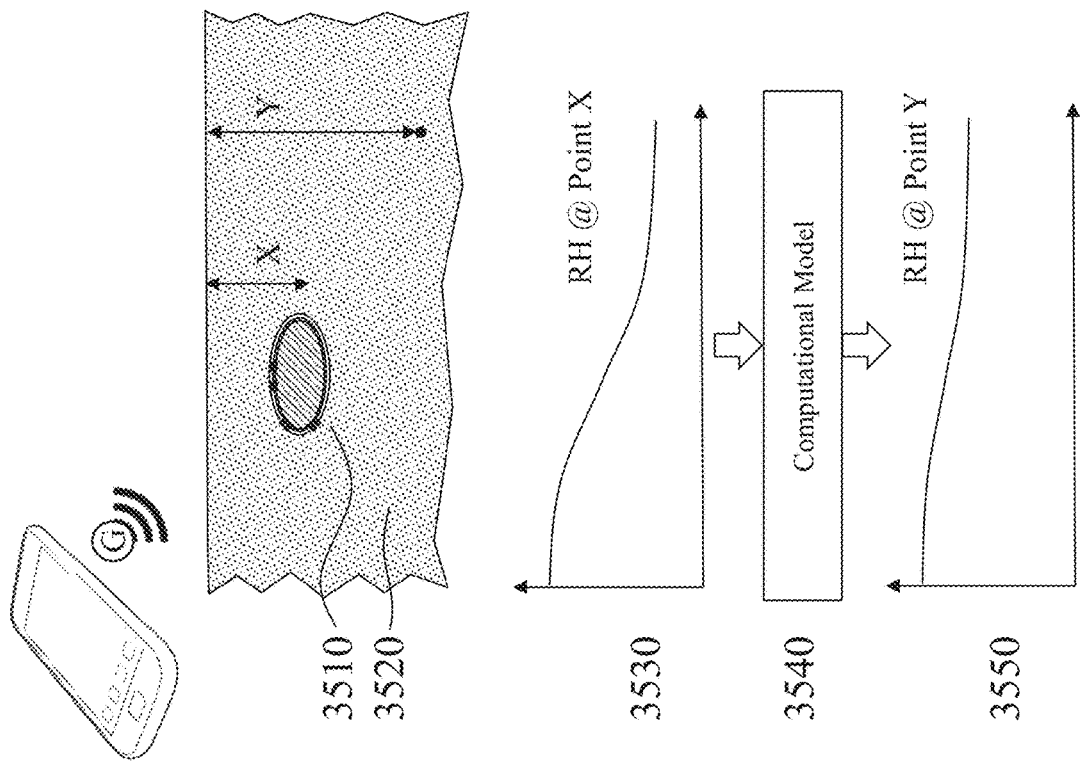
FIG. 35 depicts schematically the determination of relative humidity at a point within a structure based upon characterization at a different point within the structure.

Prediction of Relative Humidity: The deployment of a SMAK within a structure allows for the measurement of one or more material parameters and the determination from these of one or more other parameters relating to the material. Additionally, these measurements also allow for the determination from these of one or more other parameters relating to the material at a different position within the structure. For example, referring to FIG. 35 the measurement of relative humidity (RH) at a first depth X is employed in the projection of relative humidity at a different depth Y. Accordingly, a sensor (SMAK) 3510 is embedded within the material 3520, e.g. concrete, at a depth X. Extracted data from the sensor 3510 yields a first RH curve 3530 with time. Typically, this is a series of discrete measurements over time rather than a continuous measurement, but it may be. These results are fed into a computational model 3540 which establishes a second RH curve 3550 at a second depth Y. Accordingly, based upon this analysis not only can the current RH be projected at the depth Y but also a forward projecting analysis undertaken to establish a predicted RH at different points forward in time. For example, a maximum RH may be established at the depth Y during the curing stage of the material 3520 in order to assess the extent and duration of curing. Longer term the RH projections may be employed to assess water penetration into the structure and accordingly when would moisture reach metal reinforcing structures for example. Similar measurements and predictions can be made for other aspects of the material such as chloride penetration and similarly projected forward. Optionally, computational algorithms may also be employed to determine the equilibrium relative humidity after covering the concrete with flooring materials, membranes, etc.

Embedded Chloride and Corrosion Potential Sensors: Chloride-sensitive/selective electrodes in which a metal (or a metal wire) is surrounded by a solution, a coating or deposits of its oxide or its chloride solution (such as Ag/AgCl electrodes or Ir/IrO electrodes) display an electrical potential that is dependent on the surrounding environment. The dependence of the potential of this electrode on the chloride content is well-established and follows Nernst Law. Therefore, the electrical potential of this electrode, measured by means of another half-cell, can indicate the concentration of chlorides in the surrounding medium. This is possible through pre-determined calibration formulae in which the relationship between the electrode potential and the chloride concentration is determined. Such a chloride-sensitive/selective electrode may form part of a SMAK according to an embodiment of the invention.

Figure 36:
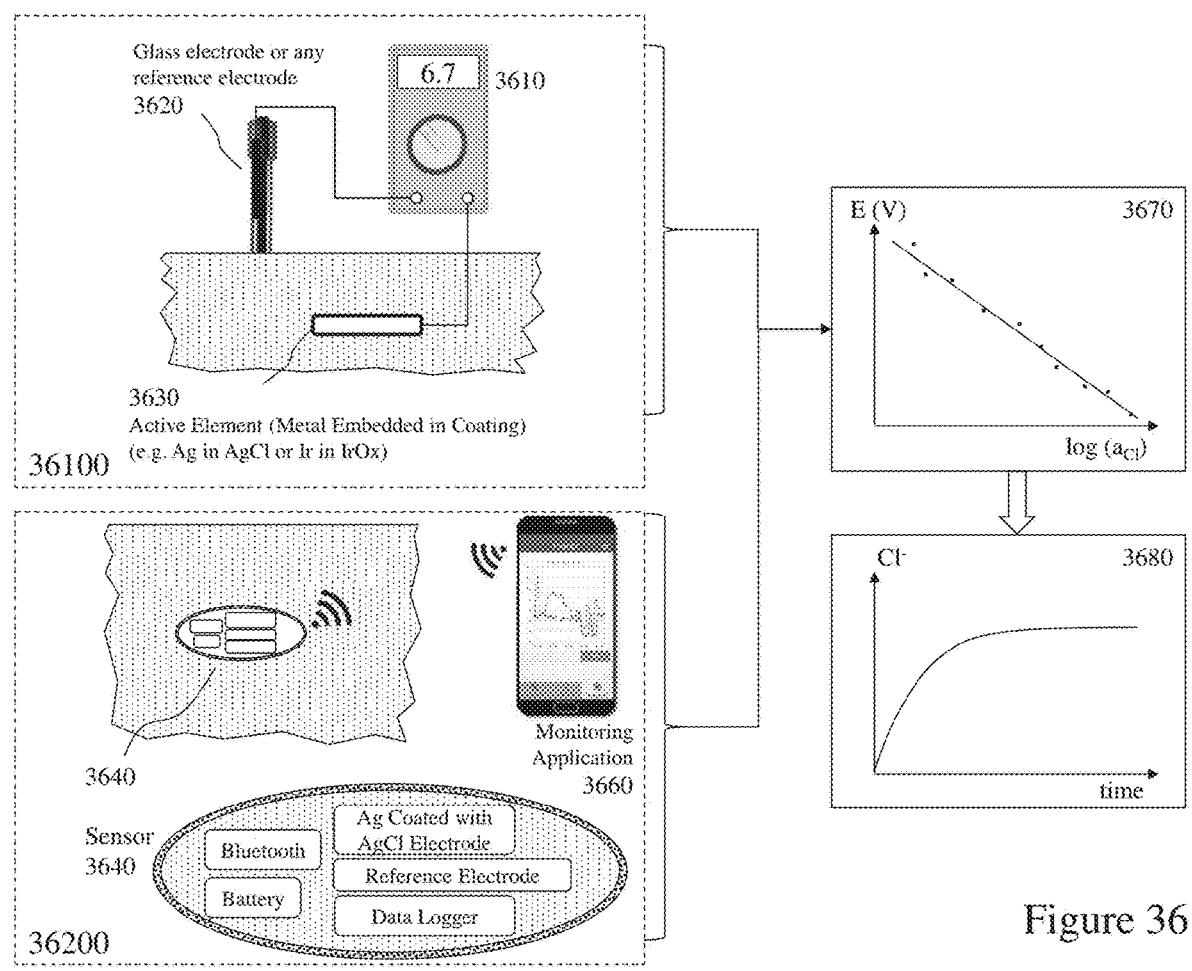
FIG. 36 depicts exemplary embedded and partially embedded sensor configurations for establishing chloride ion levels according to embodiments of the invention.

FIG. 36 depicts exemplary embedded and partially embedded sensor configurations for establishing chloride ion levels according to embodiments of the invention within first and second images 36100 and 36200 respectively. Within first image 36100 a partially embedded sensor configuration is depicted wherein a measurement device 3610 is connected to a reference electrode 3620, e.g. a glass electrode as known in the art, connected to the surface of the concrete as described above in respect of FIG. 4B or via a conductive pad such as described in respect of FIG. 3. The device 3610 is also connected to an active element 3630 embedded within the concrete such as a metal element embedded within a coating such as Ag in AgCl or Ir in IrOx.

Within second image 36200 an embedded sensor 3640 exploiting the concept depicted in first image 36100 is depicted which performs the measurements of measurement device 3610, reference electrode 3620, and active element 3630 but within a self-contained sensor, the embedded sensor 3640. As depicted the embedded sensor 3640 contains a data logger, a reference electrode, a pH sensitive coated metal (e.g. Ag with AgCl coating), a battery, and a Bluetooth transceiver which allows data to be transferred from the embedded sensor 3640 to a device 3660. Other elements, not depicted in third image 36200, may form part of the embedded sensor 3660.

Geotagging of Concrete RFID/NFC: Within the description above one or more SMAKs are embedded within concrete or another construction material which is subsequently deployed at a work site. For example, SMAKs added to concrete prior to transportation, during pouring etc. end up within the concrete without control of its position. Likewise, SMAKs embedded within other materials at manufacture such as plasterboard, fiberboard, etc. are deployed at a worksite without specific knowledge of the SMAKs location. Accordingly, these scenarios result in the challenge of properly identifying the location of the SMAK. If the sensor is attached, for example to a rebar, then the sensor location can be defined through manual techniques such as giving it a proper name, taking pictures, adding comments or manually identifying the location on blueprint. However, even in these instances as well as those where the location of the SMAK(s) is uncontrolled then it would be beneficial to provide a means of automatically identifying and locating the SMAK(s) and embedded sensor(s) within a project or a structure. One such methodology is geographical identification (geotagging) such as described above in respect of FIGS. 4A to 4C wherein a sensor(s) location can be defined through the use of a combination of techniques including, but not limited to, radio-frequency identification (RFID), near field communications (NFC), and beacons.

Accordingly, the location of a sensor or sensors can be automatically established and subsequently visualized through a two-dimensional (2D) or three-dimensional (3D) model. For example, a SMAK may exploit beacons to establish its location relative to the beacons which are then referenced to a global position through one or more global navigation system devices associated with the one or more beacons. Accordingly, the SMAK may establish its location which is subsequently stored and transmitted to a scanning device when interrogated by the scanning device. Accordingly, these beacons may be deployed during the initial pour of the concrete or deployment of the construction material and then subsequently removed as the construction moves to another location.

Integration of Sensor Data in Building Information Modelling: The automated acquisition and establishment of location of SMAKs as described above allows for the integration of this location data and the subsequent characteristics of the construction material(s) within a building information model (BIM) which can be used to facilitate the integration between different parties (e.g. owner, architect and engineer among others) and to facilitate the design, construction planning and management of the infrastructure. Adding to the technology integration services, the collection of live data of fresh, hardening and cured concrete using SMAKs allows for the live visualization of data within the BIM through PEDs and/or FEDs both at the work site and remotely. During the construction phase, the aim is to unify the information on fresh concrete properties, continuous in-place strength, temperature, relative humidity, moisture content and occurrence of defects within a structural element which will facilitate the management of the infrastructure during completion of the structure. The BIM may also integrate additional data such as actual strength versus target (design) strength, weather data, etc. Accordingly, user benefits would be seen in the optimization of scheduling, better quality control during the completion phase, easier communication between parties, quick assessment of critical situations as well as easy data-management. Accordingly, mapped SMAK data relative to different structures may be established yielding mapping similar to that depicted by first and second contour maps 510 and 520 in FIG. 5. However, rather than an operator establishing a plurality of measurements across a concrete surface with a physical test system that automatically determines it location relative to a set of beacons and a GPS location the SMAKs have automatically acquired or continue to automatically acquire their location and transmit this together with the measurement data either once at initial reading or with every reading. In this manner, a user need only exploit a scanning device to acquire the SMAK data wherein it is automatically uploaded to the remote storage, processed within a BIM tool, and then available to parties associated with the project to access and review. Where the location data is acquired on initial read this may be in association with a unique identifier of the SMAK such that this data is stored within the remote databases and subsequent reads of the SMAKs establish data and unique identity so that the association of SMAK to location is established through the initial stored data.

Figure 37:
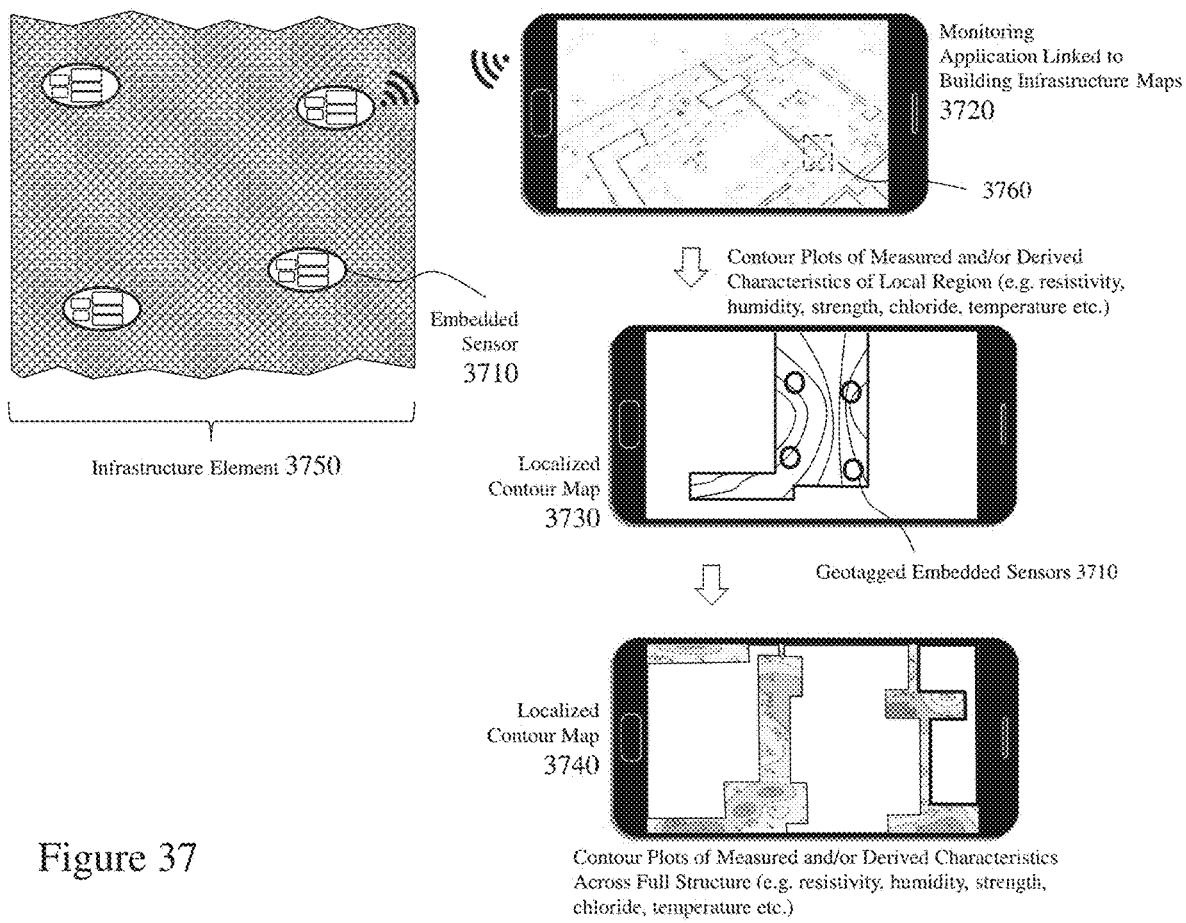
FIG. 37 depicts an exemplary schematic wherein embedded sensor data is integrated within a building information management (BIM) system according to an embodiment of the invention.

Such an exemplary process is depicted schematically in FIG. 37 wherein an infrastructure element 3750 is depicted wherein a plurality of embedded sensors 3710 are deployed within it as discussed above. Further, as discussed above the information acquired, stored, and/or generated by the embedded sensors 3710 is transferred to a scanning device and therein can be processed upon the scanning device and/or uploaded to a remote server wherein it may be processed and then downloaded to the scanning device. Accordingly, referring to second image 3720 an application associated with the embedded sensors 3750 may be linked to a BIM such that a region 3760 within the BIM may be selected and its data presented such as depicted in third image 3730 wherein a contour plot of the region 3760 is depicted together with the locations of the embedded sensors 3710 which are obtained through geotagging/geolocation such as described supra. Accordingly, as depicted in fourth image 3740 the user can adjust the portion of the infrastructure depicted, such as full structure, as well as the format of the depicted data. Accordingly, the user may elect to depict contour plots of measured and/or derived characteristics including, but not limited to, resistivity, humidity, predicted strength, chloride ion concentration, temperature etc.

Figure 38:
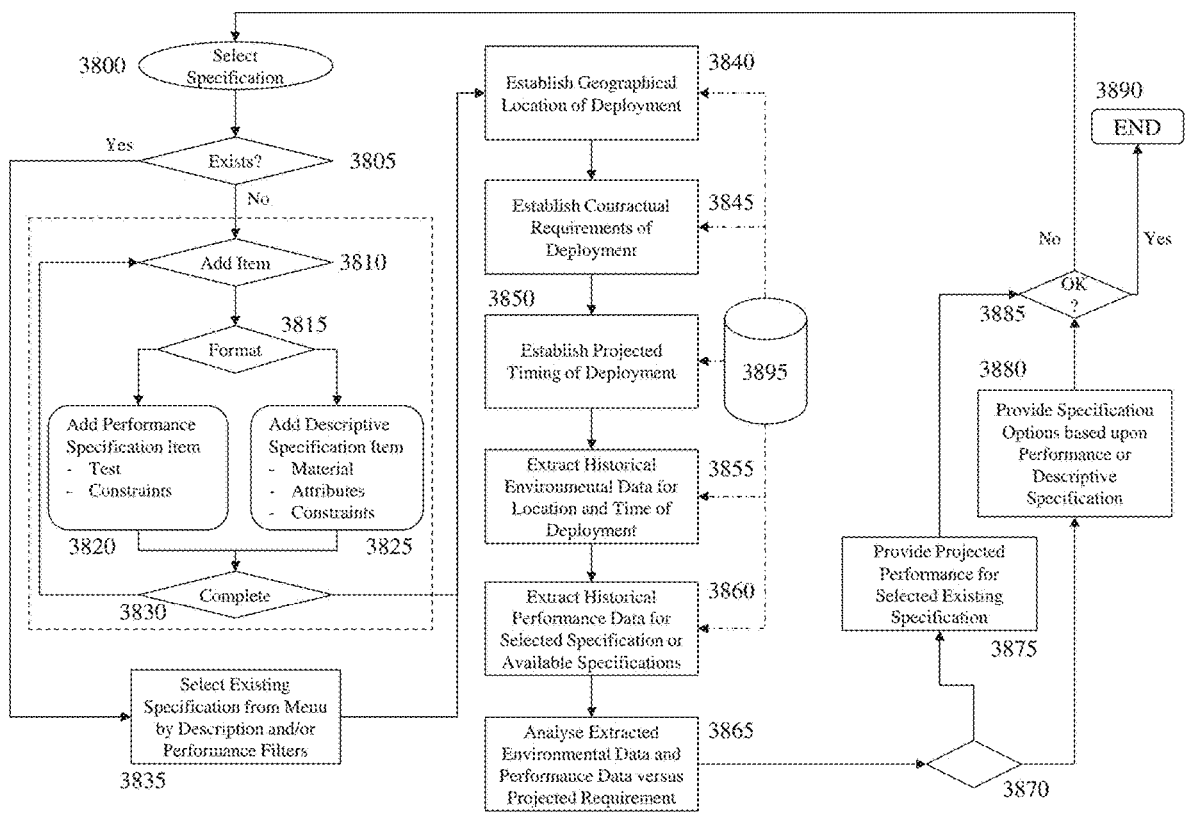
FIG. 38 depicts an exemplary process flow for the verification and/or specification of a construction material manufacturing composition based upon acquired material performance data from previous deployments acquired using sensors according to embodiments of the invention.

Performance Based Construction Material Selection: Referring to FIG. 38 there is depicted an exemplary process flow for the establishment of a manufacturing specification in respect of a construction material, such as concrete for example, exploiting acquired performance data from SMAKs and/or other performance monitoring sensors. Accordingly, the process as depicted comprises steps 3800 to 3890 in conjunction with a database 3895.

Step 3800 wherein the user initiates the process for selecting a material specification.

Step 3805 wherein a determination is made as to whether the specification already exists or not, wherein if the specification exists the process proceeds to step 3835 otherwise it proceeds to step 3810.

Steps 3810 to 3830 wherein the process of construction of a particular material specification containing a number of items is presented. Upon addition of an item through steps 3810 to 3825 the process determines in step 3810 whether the specification is complete or not and proceeds to step 3840 upon completion or step 3810 if not. Within some embodiments of the invention the determination of whether the completion has occurred is based upon selecting a number of items until a total number of items desired is achieved. Optionally, the determination is made by the user or through a combination of the process and user. For example, the user may be guided to choose a base material (e.g. type of cement), a number of additives in predetermined classes of additive (e.g. aggregate, admixture, etc.) wherein selection of at least one in each as the process moves sequentially from one to another class would mean completion of the specification. Accordingly, the process will loop until the appropriate number of specification items are defined and/or the user denotes completion.

An initial decision is made in step 3815 as to whether the specification item to be created will be descriptively based or performance based. A descriptive specification item may reference a specific material or materials and the materials attributes and/or constraints while a performance-based specification item would be established through the physical and/or chemical characteristics of the construction material either after completion of production or upon installation and thereafter. Accordingly, these are performed in steps 3820 and 3825. In this manner the construction material may be specified in terms of final target performance rather than by specific brand, identity and/or composition. Within this series of steps 3810 to 3830 the user may also establish one or more quantifiable properties and/or standard tests and may include predetermined dependent variables and/or constraints of which the construction material must satisfy. These would typically be provided to the user from a database such as database 3895. Where the specification items are listed descriptively then the item may include the material and its material quantifiable property or properties such as water/cement ratio, a set of material attributes, and/or constraints which the materials should fall within.

Once defined, either descriptively or by performance, the specification item is preferably complete and added to the concrete specification being built. The list of completed specification items may be compared to the total number of items that are to be defined for the current specification and if all of the items have not been completed, the next specification item should be defined. Each additional item can be either descriptive or performance-based again and a concrete specification may therefore contain a mix of both descriptive and performance-based specification items. Once all of the items for a particular concrete specification have been properly defined and constrained the specification is stored.

Step 3835 wherein if the decision in step 3805 was to select an existing specification then the user proceeds to make the selection from a menu using description and/or performance filters, for example.

Step 3840 wherein upon selection of the established specification or completion of the new specification the process establishes the geographical location for the deployment of the construction material. This may, for example, be by user entry or alternatively through association of the construction material specification to a project wherein the data for the project includes this and other information as required including, but not limited to, that in steps 3845 to 3860.

Step 3845 wherein the contractual requirements associated with the deployment are established. These may, for example, be a restriction on how long formwork can be left up after construction material is poured, how much material is required, time limits for delivery and pouring as the location may be within a busy downtown core, an issue from another aspect of the project etc.

Step 3850 wherein projected timing of the project is established such as when formwork will be established, when pouring should be started, when pouring should be complete, etc. are extracted from the database 3895

Step 3855 wherein historical data relating to the location and the projected time of deployment are extracted from the database 3895.

Step 3860 wherein historical performance data for the selected specification or available specifications based upon the performance and/or descriptive specification items is extracted from the database 3895.

Step 3865 wherein the extracted historical data relating to location, time, historical environmental data, historical performance data etc. are processed to establish a projected set of construction material characteristics at one or more predetermined points in time.

Step 3870 wherein the process determines whether the user selected an existing specification and proceeds to step 3875 or provided specification options and proceeds to step 3880.

Step 3875 wherein the user is provided with projected performance of the selected existing specification based upon the location, time, historical environmental data, historical performance data etc.

Step 3880 wherein the user is provided with specification options based upon the target characteristics defined by the performance and/or specification items selected by the user being matched against the available construction material specifications based upon the location, time, historical environmental data, historical performance data etc.

Step 3885 wherein the user determines whether to stop the process wherein the process proceeds to step 3890 or to iterate and the process returns to step 3800. Optionally, in the subsequent iterations the user may be provided with options to adjust the project related data such as whether a deployment is undertaken earlier or later, whether an additive should be employed, etc.

Optionally, the process automatically performs the determination in step 3885 based upon the projected performance meeting the required performance requirements. Optionally, the process may extract the target performance specification items from the database 3895 based upon selection of the project by the user within another process step and therein perform a construction material selection automatically.

Figure 39:
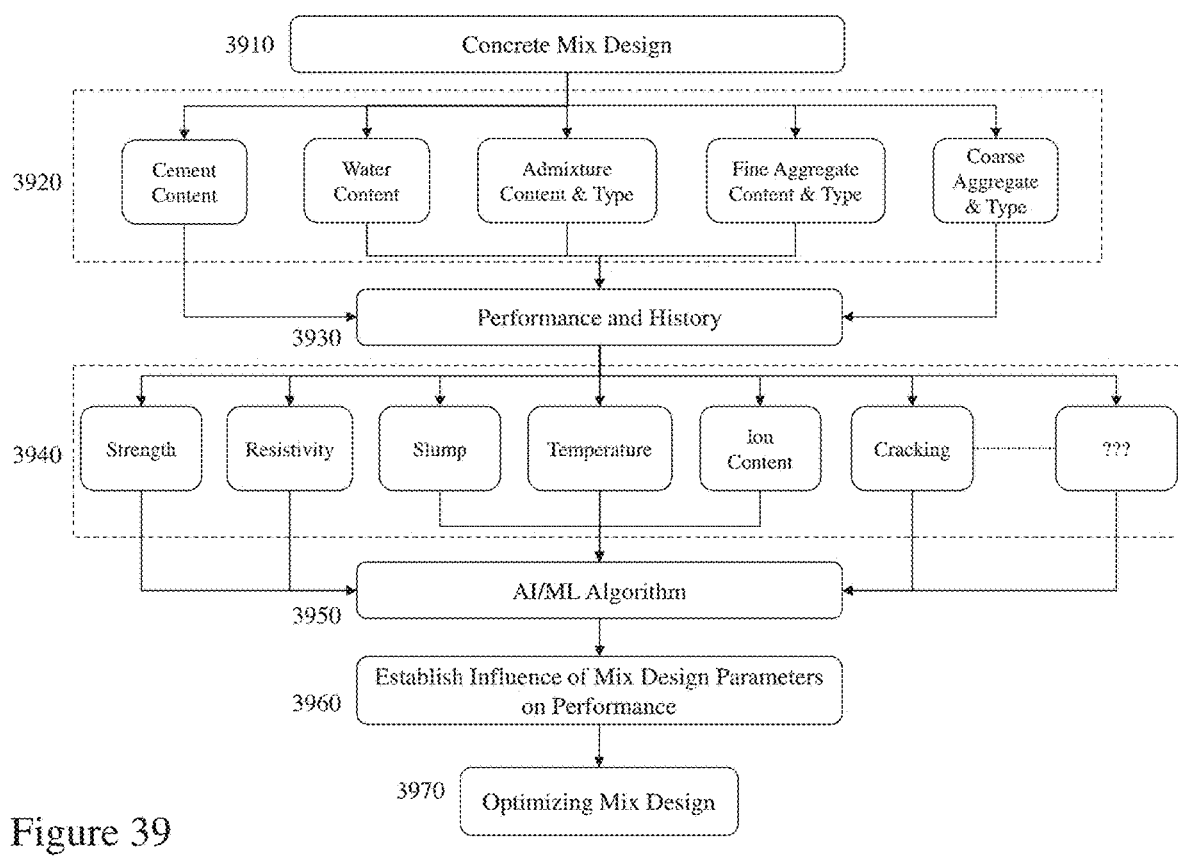
FIG. 39 depicts an exemplary process flow for optimizing a manufacturing specification for a construction material according to an embodiment of the invention exploiting machine learning and artificial intelligence.

It would also be evident that the acquisition of data relating to multiple construction material, e.g. a concrete mix, also allows for optimization of a concrete mix as a discrete process for a manufacturer as opposed to the determination of a mix design for a specific project as described and depicted in FIG. 38. Such an exemplary process flow is depicted in FIG. 39 for optimizing a manufacturing specification for a construction material according to an embodiment of the invention exploiting machine learning and artificial intelligence comprising first to seventh blocks 3910 to 3970 respectively, these being:

First block 3910 wherein a user can select a concrete mix design;

Second block 3920 wherein the concrete mix elements are established such as cement content, water content, admixture content and type, fine aggregate content and type, and coarse aggregate content and type;

Third block 3930; wherein the performance data and history for the selected mix are extracted from the stored data within the remote servers which can comprise the data acquired from embedded sensors, partially embedded sensors, third party sources such as environmental data etc., as well as data established at the time of concrete mix production and transportation;

Fourth block 3940 wherein the extracted performance data and history are analysed to extract different properties of the concrete such as strength, resistivity, slump, temperature, ion content, cracking etc.

Fifth block 3950 wherein artificial intelligence (AI)/machine learning (ML) algorithms and/or processes are employed to process the extracted data;

Sixth block 3960 wherein the analysis is performed by the AI/ML, algorithms to establish the influence of mix design parameters on the performance of the concrete mix such as variations in mix preparation, mix transportation, deployment, life cycle etc.; and Seventh block 3970 wherein amendments to the concrete mix can be determined to optimize the mix such as for improved long term strength, reduced chloride ions, reduced time before formwork removal, reduced impact of ambient environment etc.

The process described and depicted in respect of FIG. 39 may be fully automated or it may require user input such as identification of which aspects of performance of the mix are to be assessed/optimized. Further, the analysis may be filtered such as for geographic location, season, type of infrastructure element, etc.

Figure 40:
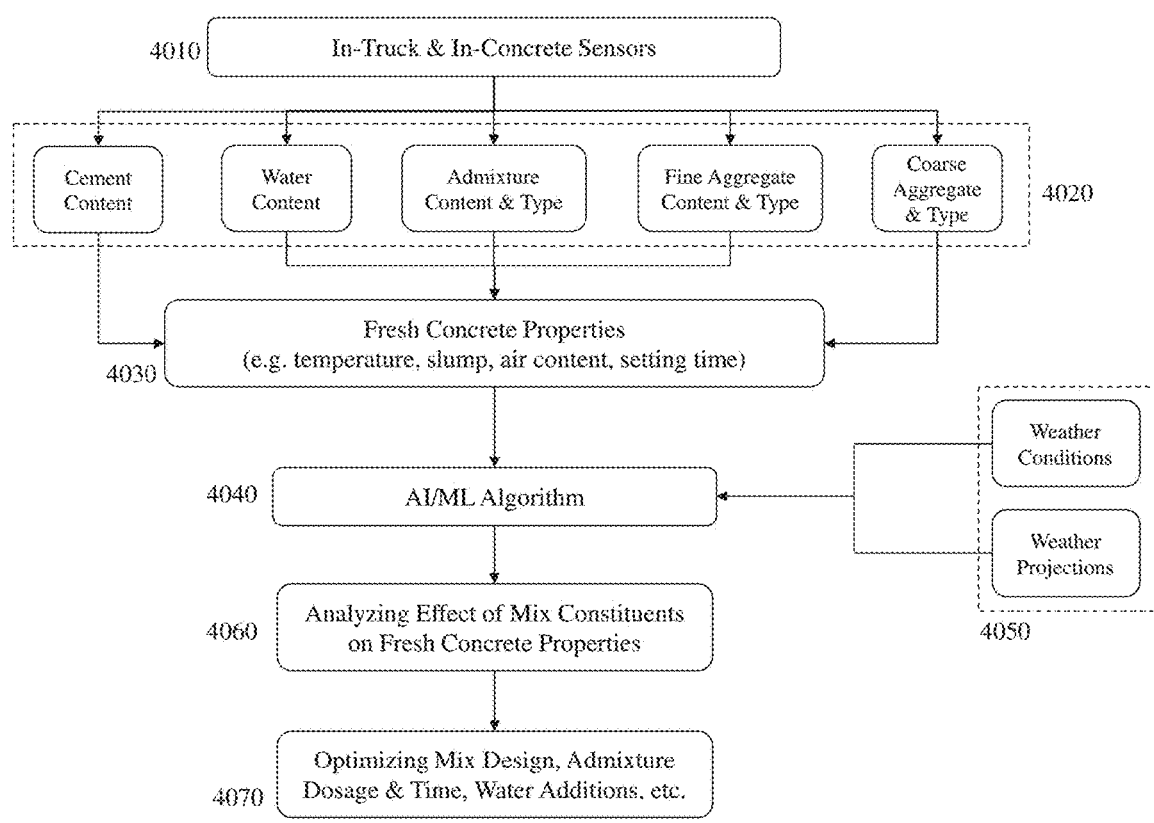
FIG. 40 depicts an exemplary process flow for optimizing a construction material during transportation according to an embodiment of the invention exploiting machine learning and artificial intelligence.

Optionally, a variant process may be implemented such as depicted in FIG. 40 wherein analysis is performed in respect of transportation of the construction material, e.g. concrete mix. In many concrete mix designs and deployments one or more admixtures are added to the concrete. These may be added at various points including, but not limited to, concrete batching, in truck, during deployment, and after deployment. Accordingly, FIG. 40 depicts an exemplary process for assessing admixtures, water etc. both in terms of which to add to the construction material based upon acquired historical data relating to their addition, delivery, performance etc. also determine when to add a particular admixture to a construction material batch and the quantity to add. For example, the analysis may determine that an admixture improving the low temperature pouring characteristics and initial curing of concrete is best added thirty minutes prior to pouring. Further, as this may be problematic for some or all deliveries the admixture(s) may be preloaded into one or more dispensers which are automatically triggered based upon downloading of a program to the concrete truck from the database for a specific delivery batch. In this manner, the admixture(s) are automatically added rather than when the truck driver can stop and add them. Equally, such analysis may determine that a batch having been loaded for two hours reaches a point where subsequent deployment will result in reduced performance or that the current projected environmental conditions will require all loads to be poured within a predetermined period of time if the concrete is required as a single contiguous block rather than multiple layers as a second pour is made upon a curing previous pour etc.

Accordingly, the exemplary process flow comprises first to seventh blocks 4010 to 4070 respectively, these being:

First block 4010 wherein data acquired from in-truck and in-concrete sensors such as described above is collected and stored within the one or more remote servers storing information relating to the sensors as well as that established from concrete batch manufacturing plants, sensors embedded within the infrastructure elements, semi-embedded sensors associate with infrastructure elements, etc.;

Second block 4020 wherein data relating to the mix transported for which data exists at the various points such as batching, truck loading, pouring, curing, ongoing life cycle monitoring etc. are retrieved and associated with the in-truck and in-concrete sensor data;

Third block 4030 wherein the fresh concrete properties such as temperature, slump, air content, setting time etc. are retrieved and associated with the data existing at the various points such as batching, truck loading, pouring, curing, ongoing life cycle monitoring etc. are retrieved and associated with the in-truck and in-concrete sensor data;

Fourth block 4040 wherein a plurality of artificial intelligence (AI)/machine learning (ML) algorithms and/or processes are employed upon the data in conjunction with data from other sources such as weather conditions and weather projections extracted from fifth block 4050;

Sixth block 4060 wherein the analysed effects of the mix constituents on the fresh concrete properties are established against the fresh concrete properties; and Seventh block 4070 wherein optimizations of the mix design, admixture dosage and time, water additions etc. are established.

Figure 41:
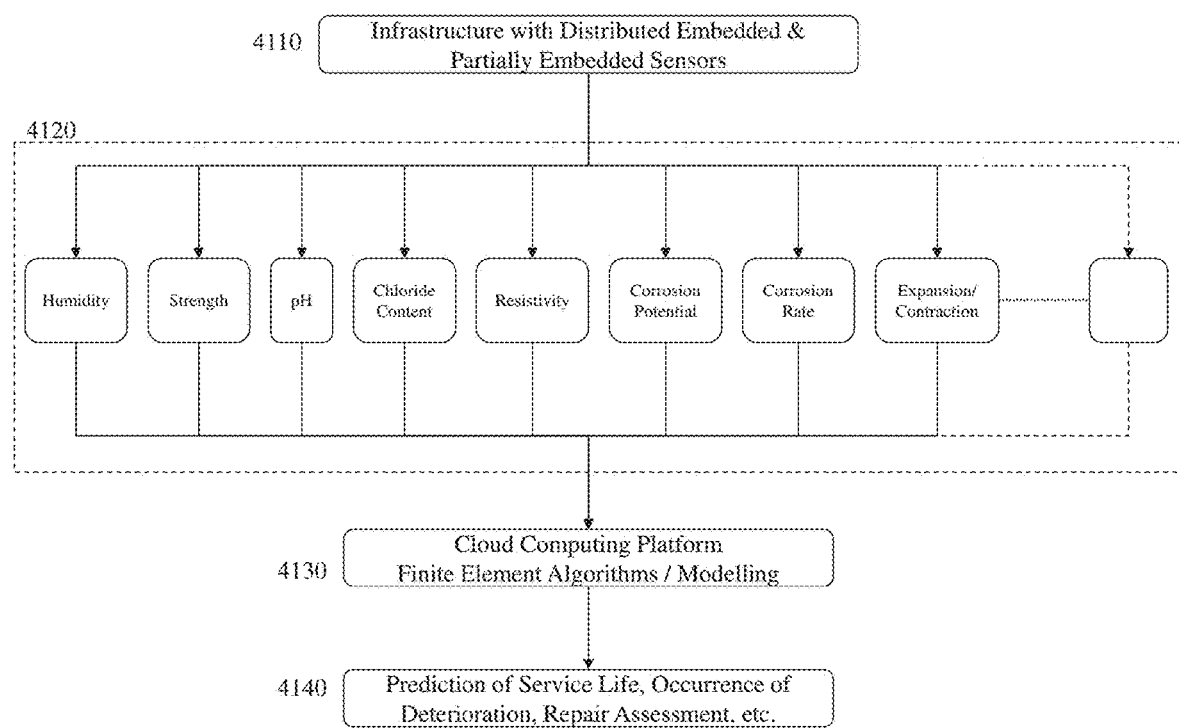
FIG. 41 depicts an exemplary process flow for service life assessment for an infrastructure element exploiting monitored installations of its construction material according to an embodiment of the invention exploiting machine learning and artificial intelligence.

Each of the exemplary processes described and depicted in respect of FIGS. 38 to 40 exploits the acquisition of data from embedded sensors within the infrastructure. As depicted in FIG. 41 an item of infrastructure has a plurality of embedded and non-embedded sensors associated with it as indicated in first block 4110. These measurements as indicated in second block 4120 may include, but are not limited to, humidity, strength, pH, chloride content, resistivity, corrosion potential, corrosion rate, and expansion/contraction. This data is then embedded to a cloud computing platform exploiting finite element algorithms and finite element modelling in third block 4130 wherein in fourth block 4140 the cloud computing platform generates data relating to prediction of service life, occurrence of deterioration, repair assessment etc.

Artificial Intelligence/Machine Learning in Material and/or Plant Performance: It would be evident that a process such as depicted in FIG. 38 may exploit artificial intelligence and/or machine learning in order to establish projected material performance. Optionally, historical performance data of construction material specifications may be employed to assess plant performance in manufacturing the construction material(s). Such analysis may result in adjustments to construction material manufacturing processes and/or compositions (recipes) at one or more plants in dependence upon analysis across all plants. Such a process within FIG. 38 together with variants and/or options described can aid producers, engineers, designers, etc. Ready mixed concrete producers, for example, can have hundreds or thousands of concrete mixes (recipes or designs) which are delivered to different projects with various specifications including target strength, workability, durability, air content etc. These mixes are subjected to quality assurance (QA) and quality control (QC) through which various data on concrete properties which may be collected with SMAKs from initial manufacture to delivery and on into the life of the structure built. Accordingly, the ability to assess historical data helps ready mix producers select the most appropriate mix from their database based on the specifications requested by the customer for the location, time, etc. AI algorithms and processes including machine learning can be utilized to analyze this massive database and help the ready mix producer select the most suitable and/or economical mix that meets the required specifications.

In addition, combining SMAKs with truck-mounted sensors and/or sensors attached to the formwork etc. can be used to collect more data during the delivery process. After delivery, the SMAKs can be used to collect additional data not only during the setting, curing and hardening stages but also during the subsequent life of the structure. Through a global Internet of Things (IoT) platform all this data can be used to extend the capabilities of the Artificial Intelligence algorithms as developed above and add predictive features to the sensors and software applications exploiting these sensors and the data acquired. Such an IoT platform can also help with more accurate and real-time optimization of the concrete mix at the batching plant for an ongoing project as well as delivery etc.

Artificial Intelligence/Machine Learning for Alarms and Alerts on Work Sites: The concepts described above in respect of acquiring ongoing data relating to a construction material such as concrete, for example, both prior to deployment and subsequent to deployment can be exploited in conjunction with one or more software applications in execution upon a remote server, PEDs and/or FEDs to exploit AI/ML algorithms knowing the historical trends and performance for that concrete mix, historical and forecasted ambient conditions, and data on the practice of the construction company for accurate prediction of the concrete properties forward in time. The SMAKs and other sensors associated with the work site together with third party information sources such as weather predictions over next few hours, day, several days etc. can be used to actively monitor and project the material characteristics and provide alerts, alarms, and suggestions during the construction of a structure to improve the final properties of the concrete. The sensors can continue collecting data during the service life of the structure and the AI algorithms can monitor this data to predict the performance of concrete structures and assist with the repair and maintenance schedules.

Artificial Intelligence/Machine Learning for Delivery Vehicles: Next generation of concrete trucks may be equipped with onboard systems to adjust the mixture by adding water and chemical admixtures such as accelerators, air entertainers, plasticizers, etc. that control concrete properties. As discussed above the data collected from the embedded and truck-mounted sensors can be used in conjunction with the variable data from ambient conditions, GPS location of the truck, traffic data, etc. to control and monitor automatically the amount and timing of the addition of water and chemical admixtures to ensure that the final concrete at the delivery time meets the required specifications set by the customer, engineers, designers etc. Further, as noted supra additional material characteristics such as slump can be automatically determined during delivery such that determinations such as whether to reject a load on the basis of slump (workability), air content etc. can not only be made automatically but also earlier so that a replacement load can be established. Further, automatically adding said water and/or admixtures allows for automatic updating of batch related data avoiding issues relating to human error either in which admixture was actually added, the quantity added, when and how much water was added etc.

Real Time Condition Assessment and/or Service Life Prediction: The ongoing determination of pH, chloride content at given depths, reinforcement corrosion potential, reinforcement corrosion rate, occurrence of cracking, among other collected attributes, allows an enhanced prediction of the concrete service-life in a real-time manner. Such data may be collected within a cloud based platform and analyzed using numerical algorithms, machine learning and artificial intelligence in order to predict several service-life attributes using the collected data. For example, a knowledge of the chloride content at several given depths allows for determination of the future point in time at which the chlorides will reach the reinforcement bar (rebar) surface in the concentrations required to initiate corrosion. Such data can also corroborate the existing knowledge base and expand on the current service-life prediction methods.

Continuity of Data: At present only parts of the overall product, transport, deployment and life cycle of a construction material such as concrete are established. The exploitation of SMAKs according to embodiments of the invention allows for enhanced data acquisition and analytics at all points in the cycle from initial concrete batching, transportation, pouring and placing stages. Periodic acquisition of data from the SMAKs during this cycle can be stored within cloud based databases wherein remotely stored or locally stored applications may access and exploit this data in order to provide real time and forward projecting performance analysis. Accordingly, the concrete properties may be monitored within the delivery vehicle, e.g. concrete truck, using truck-mounted sensors/units and this data transferred together with additional data such as GPS location, local temperature, humidity, etc. to the cloud to complete the data history of the embedded sensor within the truck. With appropriate "tagging" of the batch to the SMAKs loaded into the batch to the truck etc. than a full history can be established.

Embedded and Surface Mounted Corrosion/Resistivity Sensor: Within the description above in respect of resistivity measurements and with reference to FIGS. 7, 8, 17A and 17B 4-point/6-point probe devices for handheld use in determining aspect of the concrete characteristics and/or reinforcing element characteristics have been described. However, alternatively, the device may be configured for surface mounting via one or more fittings embedded into the concrete at the time of pouring (such as described and depicted in FIG. 18) or subsequently such that ongoing performance data can be acquired without requiring a user perform the measurements. In this manner, surface mount devices may be attached and employed in locations that subsequently become inaccessible through subsequent aspects of the structures building and completion or remove the requirement for users to return periodically and perform the measurements. Accordingly, the surface-mounted sensor may exploit techniques described within this specification such as to provide, for example, rebar corrosion rate in a connectionless manner via a four-point probe. In this configuration, the potential difference between the two inner probes is monitored following the application of a narrow DC current pulse applied from the outer probes for a short period of time. Analyzing the recorded response yields conclusions regarding the reinforcement corrosion rate as well as the concrete resistivity. In this system, a surface-mounted fixed sensor periodically performs such measurements in order to obtain the corrosion rate and concrete resistivity. The 4-point/6-point probe may alternatively perform the pulse based analysis as depicted in FIG. 7 in combination with a swept frequency characterization as depicted in FIG. 8, a time evolving polarization resistance such as depicted in FIG. 17A, and extraction of data such as polarization resistance of rebar (charge transfer resistance) ($R_P$), double layer capacitance ($C_{DL}$), the electrical resistance of concrete ($R_{C1}$, $R_{C2}$), and electrical resistance of concrete cover ($R_{C3}$).

Within other embodiments of the invention as the surface mounted sensor unit is upon the exterior of the structure a larger battery may be employed together with a wireless interface supporting communication with SMAKs within the vicinity of the surface mount sensor. Accordingly, the surface mount sensor may collate measurements from multiple SMAKs as well as its own sensor for transmittal. The surface mounted sensor may exploit a second wireless interface to transfer data to the remote cloud database which is different to that employed in interfacing to the SMAKs.

Figure 42:
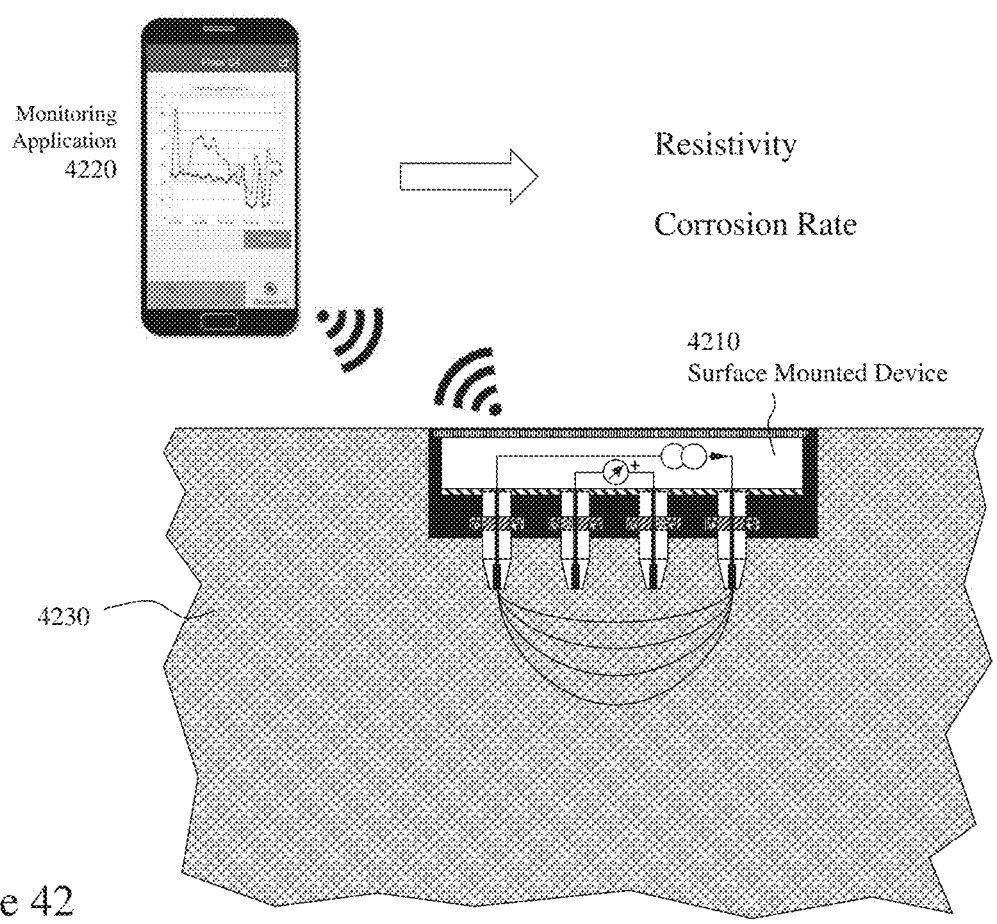
FIG. 42 depicts non-contact electrical characterization of corrosion and rebar presence within concrete according to an embodiment of the invention with a partially embedded sensor.

Alternatively, as depicted in FIG. 42 an embedded four-point/six-point probe (E4P6P) 4210 according to an embodiment of the invention as described in respect of FIGS. 7, 8, 16A and 16B is depicted. The E4P6P 4210 may, for example, be positioned prior to the concrete pour such that after the pour it is in contact with the concrete 4230 and acquires the data relating to reinforcement corrosion rate as well as concrete resistivity or alternatively the E4P6P may perform one or more of a pulse based analysis discretely, a swept frequency characterization, a time evolving polarization resistance, and extraction of data such as polarization resistance of rebar (charge transfer resistance) ($R_P$), double layer capacitance ($C_{DL}$), the electrical resistance of concrete ($R_{C1}$, $R_{C2}$), and electrical resistance of concrete cover ($R_{C3}$).

Specific details are given in the above description to provide a thorough understanding of the embodiments. However, it is understood that the embodiments may be practiced without these specific details. For example, circuits may be shown in block diagrams in order not to obscure the embodiments in unnecessary detail. In other instances, well-known circuits, processes, algorithms, structures, and techniques may be shown without unnecessary detail in order to avoid obscuring the embodiments.

Implementation of the techniques, blocks, steps and means described above may be done in various ways. For example, these techniques, blocks, steps and means may be implemented in hardware, software, or a combination thereof. For a hardware implementation, the processing units may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above and/or a combination thereof.

Also, it is noted that the embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be rearranged. A process is terminated when its operations are completed but could have additional steps not included in the figure. A process may correspond to a method, a function, a procedure, a subroutine, a subprogram, etc. When a process corresponds to a function, its termination corresponds to a return of the function to the calling function or the main function.

Furthermore, embodiments may be implemented by hardware, software, scripting languages, firmware, middleware, microcode, hardware description languages and/or any combination thereof. When implemented in software, firmware, middleware, scripting language and/or microcode, the program code or code segments to perform the necessary tasks may be stored in a machine readable medium, such as a storage medium. A code segment or machine-executable instruction may represent a procedure, a function, a subprogram, a program, a routine, a subroutine, a module, a software package, a script, a class, or any combination of instructions, data structures and/or program statements. A code segment may be coupled to another code segment or a hardware circuit by passing and/or receiving information, data, arguments, parameters and/or memory contents. Information, arguments, parameters, data, etc. may be passed, forwarded, or transmitted via any suitable means including memory sharing, message passing, token passing, network transmission, etc.

For a firmware and/or software implementation, the methodologies may be implemented with modules (e.g., procedures, functions, and so on) that perform the functions described herein. Any machine-readable medium tangibly embodying instructions may be used in implementing the methodologies described herein. For example, software codes may be stored in a memory. Memory may be implemented within the processor or external to the processor and may vary in implementation where the memory is employed in storing software codes for subsequent execution to that when the memory is employed in executing the software codes. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" may represent one or more devices for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes but is not limited to portable or fixed storage devices, optical storage devices, wireless channels and/or various other mediums capable of storing, containing or carrying instruction(s) and/or data.

The methodologies described herein are, in one or more embodiments, performable by a machine which includes one or more processors that accept code segments containing instructions. For any of the methods described herein, when the instructions are executed by the machine, the machine performs the method. Any machine capable of executing a set of instructions (sequential or otherwise) that specify actions to be taken by that machine are included. Thus, a typical machine may be exemplified by a typical processing system that includes one or more processors. Each processor may include one or more of a CPU, a graphics-processing unit, and a programmable DSP unit. The processing system further may include a memory subsystem including main RAM and/or a static RAM, and/or ROM. A bus subsystem may be included for communicating between the components. If the processing system requires a display, such a display may be included, e.g., a liquid crystal display (LCD). If manual data entry is required, the processing system also includes an input device such as one or more of an alpha-numeric input unit such as a keyboard, a pointing control device such as a mouse, and so forth.

The memory includes machine-readable code segments (e.g. software or software code) including instructions for performing, when executed by the processing system, one of more of the methods described herein. The software may reside entirely in the memory, or may also reside, completely or at least partially, within the RAM and/or within the processor during execution thereof by the computer system. Thus, the memory and the processor also constitute a system comprising machine-readable code.

In alternative embodiments, the machine operates as a standalone device or may be connected, e.g., networked to other machines, in a networked deployment, the machine may operate in the capacity of a server or a client machine in server-client network environment, or as a peer machine in a peer-to-peer or distributed network environment. The machine may be, for example, a computer, a server, a cluster of servers, a cluster of computers, a web appliance, a distributed computing environment, a cloud computing environment, or any machine capable of executing a set of instructions (sequential or otherwise) that specify actions to be taken by that machine. The term "machine" may also be taken to include any collection of machines that individually or jointly execute a set (or multiple sets) of instructions to perform any one or more of the methodologies discussed herein.

The foregoing disclosure of the exemplary embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A method comprising:
providing a sensor disposed within or for disposal within a batch of a material comprising:
a shell comprising an outer surface, an interior, and a pair of outer electrical contacts disposed on the outer surface and coupled to a pair of inner electrical contacts on the interior of the shell;
an electrical circuit disposed within the shell and comprising a battery, a wireless transceiver, a memory, and a microprocessor;
a measurement circuit coupled to the microprocessor disposed within the shell coupled to the pair of inner electrical contacts and providing a predetermined electrical measurement of a characteristic of an environment adjacent to the pair of outer electrical contacts; wherein
the microprocessor establishes in dependence upon the predetermined electrical measurement of the characteristic of the environment a current value for the characteristic of the environment and stores the current value within the memory.

2. The method according to claim 1, further comprising storing within the memory first data comprising at least one of:
calibration data relating to the batch of the material; and
batch data relating to the batch of the material;
wherein the first data was received via the wireless transceiver from another wireless transceiver at least one of prior to the sensor being disposed within the batch of material or once the sensor is disposed within the batch of material.

3. The method according to claim 1, further comprising storing within the memory first data comprising maturity data relating to a predetermined material having a composition matching that of the batch the material.

4. The method according to claim 1, further comprising providing an accelerometer within the interior of the sensor where an output of the accelerometer is coupled to the microprocessor; and
activating the sensor from a sleep mode to a measurement mode wherein the measurement circuit performs the predetermined electrical measurement of the characteristic of the environment and the memory stores the current value into memory; wherein
activating the sensor comprises detecting with the microprocessor a predetermined pattern within the output of the accelerometer.

5. The method according to claim 4, wherein the predetermined pattern relates to intentional human generated acceleration of the sensor.

6. The method according to claim 5, wherein
the predetermined pattern relates to a predetermined periodic motion consistent with the sensor and the batch of material it is disposed within being within a rotating drum of a concrete truck.

7. The method according to claim 1, further comprising providing either a magnetic field sensor within the interior of the sensor whose output is coupled to the microprocessor; and
activating the sensor from a sleep mode to a measurement mode wherein the measurement circuit performs the predetermined electrical measurement of the characteristic of the environment and the memory stores the current value into memory; wherein
activating the sensor comprises detecting either a change in the output of the magnetic field sensor indicative of a change in proximity of a magnet with respect to the magnetic field sensor.

8. The method according to claim 1, further comprising providing a magnetically activated switch within an electrical circuit coupled to the microprocessor; and
activating the sensor from a sleep mode to a measurement mode wherein the measurement circuit performs the predetermined electrical measurement of the characteristic of the environment and the memory stores the current value into memory; wherein
activating the sensor comprises establishing a change in the electrical circuit by changing a switch state of the magnetically activated switch through proximity of a magnet with respect to the magnetically activated switch.

9. The method according to claim 1, further comprising providing a reference electrode within the interior of the sensor;
providing a pH sensitive metal coating disposed upon an external surface of the sensor shell or coupled to the sensor via an electrical connection; wherein
the microprocessor establishes in dependence measurements of the reference electrode and the pH sensitive metal coating to establish a current pH value of environment and stores the current value within the memory.

10. The method according to claim 1, further comprising providing a reference field effect transistor (REFET) within the interior of the sensor;
providing a semiconductor element as part of the sensor exposed to the environment where the semiconductor element is an ISFET, MISFET or MOSFET; wherein
the microprocessor establishes in dependence measurements of the REFET and the semiconductor element a current pH value of environment and stores the current value within the memory.

11. The method according to claim 1, further comprising providing at least one beacon of a plurality of beacons, each beacon including a predetermined portion of a transceiver providing pulses of a predetermined format;
providing a global positioning receiver to provide a global position;

determining with the microprocessor at least a relative location of a plurality of relative locations, each relative location being that of the electrical measurement system relative to a predetermined subset of the plurality of beacons; and storing the plurality of relative locations and the global position within the memory.

12. The method according to claim 1, wherein the measurement circuit performs the predetermined electrical measurement of the characteristic of an environment by a process comprising the steps:

generating with the electrical measurement system an electrical pulse which is applied with a first probe;

measuring with the electrical measurement system an output electrical signal with a second probe, the output electrical signal being the result of application of the electrical pulse to the first part of the concrete structure; and applying a predetermined signal processing algorithm to the output electrical signal to generate a low frequency electrical characteristic of the environment.

13. The method according to claim 1, wherein the measurement circuit performs the predetermined electrical measurement of the characteristic of an environment by a process comprising the steps:

applying an electrical signal with a first electrical probe;

measuring an output electrical signal with a second electrical probe where the output electrical signal is generated as a result of application of the generated electrical signal;

applying predetermined signal processing to the output electrical signal to generate a processed output; wherein the electrical signal is a plurality of alternating currents applied in a predetermined sequence, each alternating current at a predetermined frequency;

the output electrical signal is a plurality of measured output voltages, each measured output voltage associated with the application of an alternating current at a predetermined frequency; and the microprocessor establishes the current value for the characteristic of the environment in dependence upon a first derivative of a frequency dependence of a magnitude of the plurality of measured output voltages with applied alternating current frequency.

14. The method according to claim 1, wherein the measurement circuit performs the predetermined electrical measurement of the characteristic of an environment by a process comprising the steps:

generating an electrical pulse with a first electrical probe;

measuring an output electrical signal with a second electrical probe as function of time for a predetermined period of time where the output electrical signal is generated as a result of application of the generated electrical pulse;

applying predetermined signal processing to the output electrical signal to generate a processed output comprising gain and phase versus frequency; and the microprocessor establishes the current value for the characteristic of the environment in dependence upon the gain and phase at low frequency.

15. The method according to claim 1, further comprising providing an outer casing disposed around the shell;

providing a resistivity sensor within the outer casing comprising a porous material exposed to the external environment around the sensor and a pair of electrical contacts disposed within the casing and coupled to another pair of inner electrical contacts on the interior of the shell where a first electrical contact of the pair of electrical contacts is disposed at a first end of the porous material and a second electrical contact of the pair of electrical contacts is disposed at a second distal end of the porous material; and determining with the microprocessor in dependence upon an electrical measurement of the resistance of the porous material established via the pair of electrical contacts; wherein the resistance of the porous material varies in dependence upon a conductivity of a pore solution of the environment around the sensor comprising at least the material.

16. The method according to claim 15, further comprising providing a peel-off cover disposed over the exposed porous material; wherein the peel-off cover is removed prior to the sensor being disposed within the material.

17. The method according to claim 1, further comprising providing a resistivity sensor comprising a porous material exposed to the external environment around the sensor and a pair of electrical contacts on the interior of the shell where a first electrical contact of the pair of electrical contacts is disposed at a first end of the porous material and a second electrical contact of the pair of electrical contacts is disposed at a second distal end of the porous material; and determining with the microprocessor in dependence upon an electrical measurement of the resistance of the porous material established via the pair of electrical contacts; wherein the resistance of the porous material varies in dependence upon a conductivity of a pore solution of the environment around the sensor comprising at least the material.

18. The method according to claim 17, further comprising providing a peel-off cover disposed over the exposed porous material; wherein the peel-off cover is removed prior to the sensor being disposed within the material.

19. The method according to claim 1, further comprising processing with the microprocessor the stored values for the characteristic of the environment to identify a time dependent periodic response within the stored values;

extracting with the microprocessor one or more characteristics for the identified time dependent periodic response; and determining with the microprocessor in dependence upon the one or more characteristics of the identified time dependent periodic response a second characteristic of the environment around the sensor.

20. The method according to claim 1, wherein each characteristic of the one or more characteristics for the identified time dependent periodic response is one of frequency, amplitude, phase shift, and duty cycle; and the second characteristic of the environment is selected from the group comprising yield stress, plastic viscosity and slump.

21. The method according to claim 1, wherein the time dependent periodic response is the result of a drum within which the batch of material and sensor are disposed; and each characteristic of the one or more characteristics for the identified time dependent periodic response is a frequency of rotation of the drum and a number of rotations of the drum.

* * * * *